United States Patent
Pohlki et al.

(10) Patent No.: US 8,877,794 B2
(45) Date of Patent: Nov. 4, 2014

(54) PHENALKYLAMINE DERIVATIVES, PHARMACEUTICAL COMPOSITIONS CONTAINING THEM, AND THEIR USE IN THERAPY

(75) Inventors: Frauke Pohlki, Ludwigshafen (DE); Udo Lange, Ludwigshafen (DE); Wilhelm Amberg, Ludwigshafen (DE); Michael Ochse, Ludwigshafen (DE); Berthold Behl, Ludwigshafen (DE); Charles W. Hutchins, Green Oaks, IL (US); Wilfried Hornberger, Ludwigshafen (DE); Mario Mezler, Ludwigshafen (DE); Sean Turner, Ludwigshafen (DE)

(73) Assignees: Abbott Laboratories, Abbott Park, IL (US); AbbVie Deutschland GmbH & Co. KG, Wiesbaden (DE)

(*) Notice: Subject to any disclaimer, the term of this patent is extended or adjusted under 35 U.S.C. 154(b) by 159 days.

(21) Appl. No.: 13/206,937

(22) Filed: Aug. 10, 2011

(65) Prior Publication Data

US 2012/0077796 A1    Mar. 29, 2012

Related U.S. Application Data

(60) Provisional application No. 61/373,526, filed on Aug. 13, 2010.

(51) Int. Cl.
| | |
|---|---|
| A61K 31/135 | (2006.01) |
| C07C 211/27 | (2006.01) |
| C07C 311/10 | (2006.01) |
| C07D 403/12 | (2006.01) |
| C07D 231/18 | (2006.01) |
| C07D 207/267 | (2006.01) |
| C07D 401/12 | (2006.01) |
| C07C 311/05 | (2006.01) |
| C07D 205/04 | (2006.01) |
| C07D 233/42 | (2006.01) |
| C07C 311/04 | (2006.01) |
| C07D 295/135 | (2006.01) |
| C07D 207/08 | (2006.01) |

(52) U.S. Cl.
CPC ............ C07C 311/10 (2013.01); C07D 403/12 (2013.01); C07C 2101/04 (2013.01); C07D 231/18 (2013.01); C07D 207/267 (2013.01); C07D 401/12 (2013.01); C07C 311/05 (2013.01); C07D 205/04 (2013.01); C07D 233/42 (2013.01); C07C 311/04 (2013.01); C07D 295/135 (2013.01); C07C 2101/02 (2013.01); C07D 207/08 (2013.01)
USPC ....................................... 514/403; 548/356.1

(58) Field of Classification Search
USPC ....................... 548/356.1; 514/403
See application file for complete search history.

(56) References Cited

U.S. PATENT DOCUMENTS

| | | |
|---|---|---|
| 4,927,838 A | 5/1990 | Guthrie et al. |
| 5,506,246 A | 4/1996 | Junge et al. |
| 5,519,034 A | 5/1996 | Kozlik et al. |
| 5,545,755 A | 8/1996 | Lin et al. |
| 6,057,357 A * | 5/2000 | Horwell et al. ............... 514/422 |
| 6,331,636 B1 | 12/2001 | Romero et al. |
| 6,426,364 B1 | 7/2002 | Egle et al. |
| 7,189,850 B2 | 3/2007 | Ceccarelli et al. |
| 7,427,612 B2 | 9/2008 | Alberati-giani et al. |
| 7,462,617 B2 | 12/2008 | Alberati-giani et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 8,420,670 B2 | 4/2013 | Amberg et al. |
| 8,563,617 B2 | 10/2013 | Amberg et al. |

(Continued)

FOREIGN PATENT DOCUMENTS

| | | |
|---|---|---|
| DE | 10315570 | 10/2004 |
| EP | 0091241 | 10/1983 |

(Continued)

OTHER PUBLICATIONS

United States Patent Office Notice of Allowance for U.S. Appl. No. 13/207,160 dated Mar. 17, 2014 (9 pages).

(Continued)

*Primary Examiner* — Kamal Saeed
*Assistant Examiner* — Janet L Coppins
(74) *Attorney, Agent, or Firm* — Lisa V. Mueller; Michael Best & Friedrich LLP

(57) ABSTRACT

The present invention relates to phenalkylamine derivatives of the formula (I)

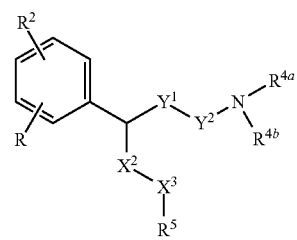

or a physiologically tolerated salt thereof.
The invention relates to pharmaceutical compositions comprising such phenalkylamine derivatives, and the use of such phenalkylamine derivatives for therapeutic purposes. The phenalkylamine derivatives are GlyT1 inhibitors.

18 Claims, No Drawings

(56) References Cited

U.S. PATENT DOCUMENTS

| | | |
|---|---|---|
| 8,642,587 B2 | 2/2014 | Lange et al. |
| 8,653,100 B2 | 2/2014 | Amberg et al. |
| 2002/0169197 A1 | 11/2002 | Egle et al. |
| 2003/0083359 A1 | 5/2003 | Lee et al. |
| 2004/0026364 A1 | 2/2004 | Kihara |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0074105 A1 | 4/2006 | Ware et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0021408 A1 | 1/2007 | Molino et al. |
| 2007/0155753 A1 | 7/2007 | Ye et al. |
| 2007/0214087 A1 | 9/2007 | Kawaguchi et al. |
| 2008/0070941 A1 | 3/2008 | Dargazanli et al. |
| 2008/0119486 A1 | 5/2008 | Jolidon et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2012/0040947 A1 | 2/2012 | Pohlki et al. |
| 2012/0040948 A1 | 2/2012 | Pohlki et al. |
| 2012/0077796 A1 | 3/2012 | Pohlki et al. |
| 2012/0295881 A1 | 11/2012 | Lange et al. |
| 2012/0316153 A1 | 12/2012 | Amberg et al. |
| 2013/0035323 A1 | 2/2013 | Amberg et al. |
| 2013/0131132 A1 | 5/2013 | Amberg et al. |
| 2013/0184238 A1 | 7/2013 | Amberg et al. |
| 2013/0203749 A1 | 8/2013 | Amberg et al. |
| 2013/0210880 A1 | 8/2013 | Amberg et al. |
| 2014/0031331 A1 | 1/2014 | Amberg et al. |

FOREIGN PATENT DOCUMENTS

| | | |
|---|---|---|
| EP | 0258755 | 3/1988 |
| EP | 0303961 | 2/1989 |
| EP | 0420064 | 4/1991 |
| EP | 1199306 | 4/2002 |
| EP | 1254662 | 11/2002 |
| EP | 1284257 | 2/2003 |
| EP | 2246331 | 11/2010 |
| WO | 81/03491 | 12/1981 |
| WO | 90/15047 | 12/1990 |
| WO | 92/06967 | 4/1992 |
| WO | 92/19234 | 11/1992 |
| WO | 92/22533 | 12/1992 |
| WO | 93/13073 | 7/1993 |
| WO | 95/07521 | 3/1995 |
| WO | 97/10223 | 3/1997 |
| WO | 97/45115 | 12/1997 |
| WO | 98/04521 | 2/1998 |
| WO | 98/56757 | 12/1998 |
| WO | 00/07978 | 2/2000 |
| WO | 00/20376 | 4/2000 |
| WO | 01/09120 | 2/2001 |
| WO | 02/076979 | 10/2002 |
| WO | 03/031435 | 4/2003 |
| WO | 03/045924 | 6/2003 |
| WO | 03/053942 | 7/2003 |
| WO | 03/055478 | 7/2003 |
| WO | 03/076420 | 9/2003 |
| WO | 03/087086 | 10/2003 |
| WO | 03/089411 | 10/2003 |
| WO | 03/097586 | 11/2003 |
| WO | 2004/007468 | 1/2004 |
| WO | 2004/013100 | 2/2004 |
| WO | 2004/013101 | 2/2004 |
| WO | 2004/022528 | 3/2004 |
| WO | 2004/071445 | 8/2004 |
| WO | 2004/072034 | 8/2004 |
| WO | 2004/080968 | 9/2004 |
| WO | 2004/096761 | 11/2004 |
| WO | 2004/110149 | 12/2004 |
| WO | 2004/112787 | 12/2004 |
| WO | 2004/113280 | 12/2004 |
| WO | 2004/113301 | 12/2004 |
| WO | 2005/014563 | 2/2005 |
| WO | 2005/023260 | 3/2005 |
| WO | 2005/037781 | 4/2005 |
| WO | 2005/037782 | 4/2005 |
| WO | 2005/037783 | 4/2005 |
| WO | 2005/037785 | 4/2005 |
| WO | 2005/037792 | 4/2005 |
| WO | 2005/023261 | 5/2005 |
| WO | 2005/040166 | 5/2005 |
| WO | 2005/046601 | 5/2005 |
| WO | 2005/049023 | 6/2005 |
| WO | 2005/058317 | 6/2005 |
| WO | 2005/058882 | 6/2005 |
| WO | 2005/058885 | 6/2005 |
| WO | 2005/099353 | 10/2005 |
| WO | 2005/123681 | 12/2005 |
| WO | 2006/008754 | 1/2006 |
| WO | 2006/034235 | 3/2006 |
| WO | 2006/063709 | 6/2006 |
| WO | 2006/082001 | 8/2006 |
| WO | 2006/102760 | 10/2006 |
| WO | 2006/121767 | 11/2006 |
| WO | 2007/143823 | 12/2007 |
| WO | 2008/038053 | 4/2008 |
| WO | 2008/148755 | 12/2008 |
| WO | 2009/024611 | 2/2009 |
| WO | 2009/121872 | 10/2009 |
| WO | 2010/020548 | 2/2010 |
| WO | 2010/025856 | 3/2010 |
| WO | 2010/029180 | 8/2010 |
| WO | 2010/092181 | 8/2010 |
| WO | 2010/138901 | 12/2010 |
| WO | 2012/020130 | 2/2012 |
| WO | 2012/020131 | 2/2012 |
| WO | 2012/020133 | 2/2012 |
| WO | 2012/152915 | 11/2012 |

OTHER PUBLICATIONS

Ashby, E.C. et al., "Single electron transfer in reactions of alkyl halides with lithium thiolates," J. Org. Chem. (1985) 50(25):5184-5193.

Barbasiewicz, M. et al., "Intermolecular reactions of chlorohydrine anions: acetalization of carbonyl compounds under basic conditions," Org. Lett. (2006) 8(17):3745-3748.

Belliotti, T.R. et al., "Structure-activity relationships of pregabalin and analogues that target the alpha(2)-delta protein," J. Med. Chem. (2005) 48(7):2294-2307.

Bermejo, a. et al., "Syntheses and antitumor targeting G1 phase of the cell cycle of benzoyldihydroisoquinolines and related 1-substituted isoquinolines," J. Med. Chem. (2002) 45:5058-5068.

Beylot, M. et al., "In vivo studies of intrahepatic metabolic pathways," Diabetes Metabolism (1997) 23(3):251-257.

Bishop, D.C., "Analgetics based on the azetidine ring," Azetidine Analgetics (1968) 11:466-470.

Blagojevic, N. et al., "Role of heavy water in boron neutron capture therapy," Topics in Dosimetry and Treatment Planning for Neutron Capture Thearpy (1994) 125-134.

Blake, M.I. et al., "Studies with deuterated drugs," J. Pharm. Sci. (1975) 64(3):367-391.

Boulay, D. et al., "Characterization of SSR103800, a selective inhibitor of the glycine transporter-1 in models predictive of therapeutic activity in schizophrenia," Pharmacology, Biochemistry and Behavior (2008) 91:47-58.

(56) References Cited

OTHER PUBLICATIONS

Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.
Burn, D., "Alkylation with the vilsmeier reagent," Chem. And Industry (1973) 870-873.
Burns, N.Z. et al., "Total synthesis of haouamine A: the indeno-tetrahydropyridine core," Tetrahedron (2009) 65(33):6600-6610.
Butte, N.F. et al., "Measurement of milk intake: tracer-to-infant deuterium dilution method," Br. J. Nutrition (1991) 65:3-14.
Cheng, Y. et al., "Relationship between the inhibition constant (KI) and the concentration of inhibitor which causes 50 percent inhibition ($I_{50}$) of an enzymatic reaction," Biochem. Pharmacol. (1973) 22:3099-3108.
Cheung, F.K. et al., "the use of a [4+2] cycloadditional reaction for the preparation of a series of 'tethered' Ru(II)-diamine and aminoalcohol complexes," Org. & Biomol. Chem. (2007) 5(7):1093-1103.
Chrzanowska, M. et al., "Asymmetric synthesis of isoquinoline alkaloids," Chem. Rev. (2004) 104(7):3341-3370.
Clayden et al., Tetra. Lett. (2003) 44(15):3059-3062.
Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.
Colandrea, V.J. et al., "Synthesis and regioselective alkylation of 1.6- and 1.7-naphthyridines," Tetra. Lett. (2000) 41:8053-8057.
Coward, W.A. et al., "New method for measuring milk intakes in breast-fed babies," The Lancet (1979) 13-14.
Czajka, D.M. et al., "Effect of deuterium oxide on the reproductive potential of mice," Annals of the New York Academy of Sciences (1960) 84:770-779.
Czajka, D.M. et al., "Physiological effects of deuterium on dogs," Am. J. Physiology (1961) 201(2):357-362.
Denkewalter, R.G. et al., Progress of Pharmaceutical Research, Drug Research (1966) 10:223-226.
Di, L. et al., "Optimization of a higher throughput microsomal stability screening assay for profiling drug discovery candidates," J. Biomol. Screening (2003) 8(4):453-462.
Dohi, T. et al., "Glycine transporter inhibitors as a novel drug discovery strategy for neuropathic pain," Pharma. & Therapeutics (2009) 123(1):54-79.
Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.
Erhunmwunse, M.O. et al., "A novel rearrangement reaction of beta-diaxo-alpha-ketoacetals," Tetra. Lett. (2009) 50:3568-3570.
Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.
Fiedler, H.B., "Lexikon der hilfsstoffe fur pharmazie, Kosmetik and angrenzende Gebiete," (1996) 4th Edition, Table of Contents.
Foster, A.B. et al., "Deuterium isotope effects in the metabolism of drugs and xenobiotics: implications for drug design," Advances in Drug Research (1985) 14:2-36.
Fraser et al., Canadian Journal of Chemistry (1971) 49(5):800-802.
Grant & Hackh's Chemical Dictionary, 5th Edition (1987), p. 148.
Green, G.M. et al., "Polystyrene-supported benzenesulfonyl azide: a diazo transfer reagent that is both efficient and safe," J. Org. Chem. (2001) 66(7):2509-2511.
Greene, T.W. et al., in Protective Groups in Organic Synthesis, 2nd Edition, John Wiley & Sons, Inc., (1991) Table of Contents.
Greene, T.W. et al., in Protective Groups in Organic Synthesis, 3rd Edition, John Wiley & Sons, Inc., (1999) Preface, Table of Contents and Abbreviations.
Guillonneau, C. et al., "Synthesis of 9-O-substituted derivatives of 9-hydroxy-5, 6-dimethyl-6H-pyrido[4,3-b]carbazole-1-carboxylic acid (2-(dimethylamino)ethyl)amide and their 10- and 11-methyl analogues with improved antitumor activity," J. Med. Chem. (1999) 42(12):2191-2203.
Gupta, A. et al., "Simple and efficient synthesis of steroidal hybrids of estrogen and vitamin D3," Synthetic Comm. (2009) 39:61-69.
Harsing, L.G. et al., "Glycine transporter Type-1 and its inhibitors," Curr. Med. Chem. (2006) 13:1017-1044.
Hashimoto, K. "Glycerine transport inhibitors for the treatment of schizophrenia," The Open Medicinal Chemistry Journal (2010) 4:10-19.
Hashimoto, K. et al., "Phencyclidine-induced cognitive deficits in mice are improved by subsequent subchronic administration of the glycine transporter-1 inhibitor NFPS and D-serine," Eurp. Neuropsychopharmacology (2008) 18:414-421.
Hashimoto, K., "Glycine transporter inhibitors as therapeutic agents for schizophrenia," Recent Patents on CNS Drug Discovery (2006) 1:43-53.
Hillier, M.C. et al., "A one-pot preparation of 1,3-disubstituted azetidines," J. Org. Chem. (2006) 71(20):7885-7887.
Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.
Javitt, D.C., "Glutamate as a therapeutic target in psychiatric disorders," Mol. Psychiatry (2004) 9:984-997.
Jellimann, C. et al., "Synthesis of phenalene and acenaphthene derivatives as new conformationally restricted ligands for melatonin receptors," J. Med. Chem. (2000) 43(22):4051-4062.
Jensen, B.L. et al., "Total synthesis of 4,5,7a,8-tetrahydro-1,2-dimethoxyphenantluo[10,1-bc]-azepin-6(7H)-one: a photochemical approach," J. Heterocyclic Chem. (1986) 23:343-347.
Jetter, M.C. et al., "Heteroaryl beta-tetralin ureas as novel antagonists of human TRPV1," Bioorg. Med. Chem. Lett. (2007) 17(22):6160-6163.
Jutz, C. et al., "The Vilsmeier-Haackarnold acylations. C-C bond-forming reactions of chloromethyleniminium ions," Adv. Org. Chem. (1976) 9(1):225-342.
Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(11):2381-2384.
Kato, S. et al., "Synthesis of deuterated mosapride citrate," J. Labelled Compounds and Radiopharmaceuticals (1995) 36(10):927-932.
King, F.D., editor "Bioisosteres, conformational restriction and pro-drugs—case history: an example of a conformational restriction approach," Medical Chemistry: Principles and Practice (1994), Chapter 14, 206-209.
Kinney, G.G. et al., "The glycerine transporter type 1 inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neurosci. (2003) 23(20):7586-7591.
Kocienski, P.J., Protective Groups, Georg Thieme Verlag Stuttgart, Germany, Table of Contents (1994).
Kreher, R.P., Hetarene II, Georg Thieme Verlag Stuttgart, Germany (1991) 583-726.
Kuhakarn, C. et al., "Synthesis of alkylated indolizidine alkaloids via pummerer mediated cyclization: synthesis of indolizidine 167B, 5-butylindolizidine and monomorine I," Tetrahedron (2008) 64(8):1663-1670.
Kushner et al., "Pharmacological uses and perspectives of heavy water and deuterated compounds," Canadian J. Physiol. Pharmacol. (1999) 77(2):79-88.
Lindsley, C.W. et al., "Design, synthesis, and in vivo efficacy of glycine transporter-1 (GlyT1) inhibitors derived from a series of [4-phenyl-1-(propylsulfonyl)piperidin-4-yl]methyl benzamides," Chem. Med. Chem. (2006) 1(8):807-811.
Lindsley, C.W. et al., "Progress in the preparation and testing of glycine transporter type-1 (glyT1) inhibitors," Curr. Top. Med. Chem. (2006) 6:1883-1896.
Lindsley, C.W. et al., "Progress towards validating the NMDA receptor hypofunction hypothesis of schizophrenia," Cur. Top. Med. Chem. (2006) 6:771-785.

(56) References Cited

OTHER PUBLICATIONS

Lizondo, J. et al., "Linezolid: oxazolindinone antibacterial," Drugs of the Future (1996) 21(11):1116-1123.
Lowe, J. et al., "A novel-nonsubstrate-based series of glycine type 1 transporter inhibitors derived from high-throughput screening," Bioorg. Med. Chem. Lett. (2007) 17(6):1675-1678.
MacLennan, A.H. et al., "Neonatal body water turnover: a putative index of perinatal morbidity," Amer. J. Obstetrics & Gynecology (1981) 139(8):948-952.
Mai, K. et al., "A fast n-substituted alpha-aminonitrile synthesis," Synthetic Commun. (1985) 15(2):157-163.
Mallesham, B. et al., "Highly efficient cul-catalyzed coupline of aryl bromides with oxazolidinones using Buchwald's protocol: a short route to linezolid and toloxatone," Org. Left. (2003) 5(7):963-965.
McOmie, J.F.W., ed., Protective Groups in Organic Chemistry, Plenum Press (1973) Table of Contents.
Meek, J.S. et al., "Diels-Alder reactions of 9-substituted anthracenes.1 II. 9-cyanoanthracene," J. Amer. Chem. Soc. (1956) 78(20):5413-5416.
Memetzidis, G. et al., "Synthesis of aromatic chloroberbines," Heterocycles (1990) 31(2):341-351.
Mezler, M. et al., "Inhibitors of GlyT1 affect glycine transport via discrete binding sites," Mol. Pharmacol. (2008) 74(6):1705-1715.
Munson, P.J. et al., "Ligand: a versatile computerized approach for characterization of ligand-binding systems," Anal. Biochem. (1980) 107(1):220-239.
Nunez, E. et al., "Differential effects of the tricyclic antidepressant amoxapine on glycine uptake mediated by the recombinant GLYT1 and CLYT2 glycine transporters," Br. J. Pharm. (2000) 129(1):200-206.
Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.
Obach, R.S., "The prediction of human clearance from hepatic microsomal metabolism data," Curr. Opin. Drug Disc. & Development (2001) 4(1):36-44.
Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.
Papageorgiou, C. et al., "163 synthesis of hydroxy-and methoxy-substituted octahydrobenzo[g]isoquinolines as potential ligands for serotonin receptors," Helvetica Chimica Acta (1989) 72:1463-1470.
Pinard, E. et al., "Selective gly T1 inhibitors: discovery of [4-(3-fluoro-5-trifluoremethylpyridin-2-yl)piperazin-l-yl]-]-[5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.
Pitts, M.R. et al., "Indium metal as a reducing agent in organic synthesis," J. Chem Soc. Perkin Transactions (2001) 1:955-977.
Pons, G. et al., "Stable isotopes labeling of drugs in pediatric clinical pharmacology," Pediatrics (1999) 104(32):633-639.
Prout, F.S. et al., "3-Benzyl-3-Methylpentanoic acid," Organic Syntheses, Coll. (1963) 4:93; (1955) 35:6.
Quirante, J. et al., "Synthesis of diazatricyclic core of magangamines from Cis-perhydroisoquinolines," J. Org. Chem. (2008) 73(7):768-771.
Rand et al., "Indium (III) chloride-promoted rearrangement of epoxides: a selective synthesis of substituted benzylic aldehydes and ketones," J. Org. Chem. (1998) 8212-8216.
Reddy, K.S. et al., "Synthesis of a 9-fluorenone derived beta-amino alcohol ligand depicting high catalytic activity and pronounced non-linear stereochemical effects," Synthesis (2000) 1:165-176.
Reddy, M.P. et al., "Applications of the Vilsmeier reaction. 13. Vilsmeier approach to polycyclic aromatic hydrocarbons," J. Org. Chem. (1981) 46:5371-5373.
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCl3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tavares, F.X. et al., "Potent, selective, and orally efficacious antagonists of melanin-concentrating hormone receptor 1," J. Med. Chem. (2006) 49(24):7095-7107.
Thompson, H.W. et al., "Stereochemical control of reductions. 9. Haptophilicity studies with 1,1-disubstituted 2-methyleneacenaphthenes," J. Org. Chem. (2002) 67(9):2813-2825.
Thomson, J.F., "Physiological effects of D20 in mammals," Annals of the N.Y. Academy of Sci. (1960) 84:736-744.
Ting, P.C. et al., "The synthesis of substituted bipiperidine amide compounds as CCR3 antagonists," Bioorg. Med. Chem. Lett. (2005) 15(5):1375-1378.
Tsai, G. et al., "Gene knockout of glycine transporter 1: characterization of the behavioral phenotype," PNAS (2004) 101(22):8485-8490.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.
White, J.D. et al., "Catalyzed asymmetric diels-alder reaction of benzoquinone. Total synthesis of (-)-ibogamine," Org. Left. (2000) 2(15):2373-2376.
Zhao, Z. et al., "Synthesis and SAR of GlyT1 inhibitors derived from a series of N-((4-(morpholine-4-carbonyl)-1-(propylsulfonyl) piperidin-4-yl) methyl) benzamindes," Bioorg. Med. Chem. Lett. (2006) 16(23):5968-5972.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/706,326 dated Jun. 11, 2013 (10 pages).
United States Patent Office Notice of Allowance for U.S. Appl. No. 12/706,326 dated Feb. 21, 2013 (9 pages).
United States Patent Office Action for U.S. Appl. No. 12/706,326 dated Sep. 21, 2012 (7 pages).
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Jul. 19, 2012 (7 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United States Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).

(56) References Cited

OTHER PUBLICATIONS

United States Patent Office Action for U.S. Appl. No. 13/206,750 dated Feb. 19, 2014 (6 pages).
United States Patent Office Notice of Allowance for U.S. Appl. No. 13/207,030 dated Mar. 11, 2014 (9 pages).
United States Patent Office Action for U.S. Appl. No. 13/566,051 dated Sep. 16, 2013 (15 pages).
United States Patent Office Action for U.S. Appl. No. 13/680,488 dated Dec. 5, 2013 (17 pages).
United States Patent Office Action for U.S. Appl. No. 13/680,488 dated Jun. 21, 2013 (43 pages).
International Search Report for Application No. PCT/EP2010/051903, mailed May 26, 2010.
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
Written Opinion for Application No. PCT/EP2010/051903, mailed Aug. 16, 2011.
Written Opinion for Application No. PCT/EP2008/061007 dated Aug. 10, 2009 (7 pages).
Written Opinion for Application No. PCT/EP2009/053 800 dated Nov. 20, 2009 (7 pages).
Written Opinion for Application No. PCT/EP2012/058760 dated Aug. 27, 2012 (4 pages).
United States Patent Office Action for U.S. Appl. No. 13/546,434 dated Apr. 14, 2014 (12 pages).
United States Patent Office Action for U.S. Appl. No. 13/792,105 dated Apr. 16, 2014 (6 pages).
United States Patent Office Action for U.S. Appl. No. 13/789,967 dated Apr. 1, 2014 (11 pages).
United States Patent Office Action for U.S. Appl. No. 14/031,265 dated Apr. 15, 2014 (14 pages).
United States Patent Office Notice of Allowance for U.S. Appl. No. 13/680,488 dated Apr. 28, 2014 (13 pages).
United States Patent Office Notice of Allowance for U.S. Appl. No. 13/207,030 dated May 13, 2015 (9 pages).

* cited by examiner

PHENALKYLAMINE DERIVATIVES, PHARMACEUTICAL COMPOSITIONS CONTAINING THEM, AND THEIR USE IN THERAPY

CROSS-REFERENCE TO RELATED APPLICATION

This claims priority to U.S. Provisional Patent Application No. 61/373,526, filed on Aug. 13, 2010, the contents of which are hereby incorporated by reference.

BACKGROUND OF THE INVENTION

The present invention relates to phenalkylamine derivatives, pharmaceutical compositions comprising such phenalkylamine derivatives, and the use of such phenalkylamine derivatives for therapeutic purposes. The phenalkylamine derivatives are GlyT1 inhibitors.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

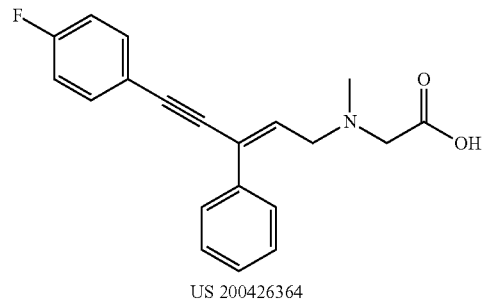

US 200426364

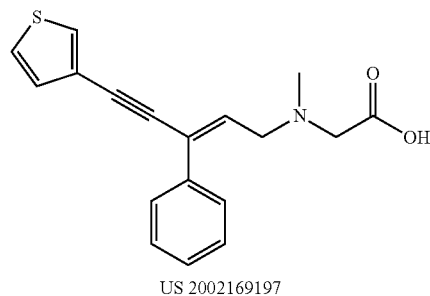

US 2002169197

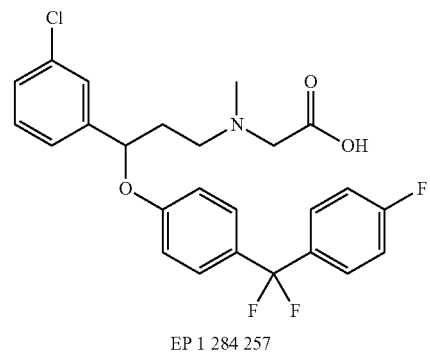

EP 1 284 257

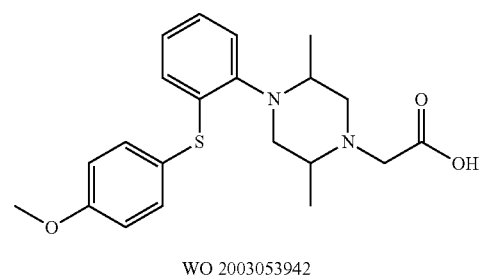

WO 2003053942

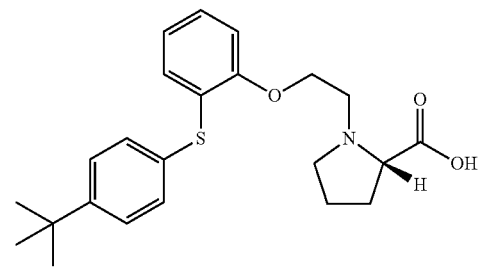

WO 2004096761

-continued
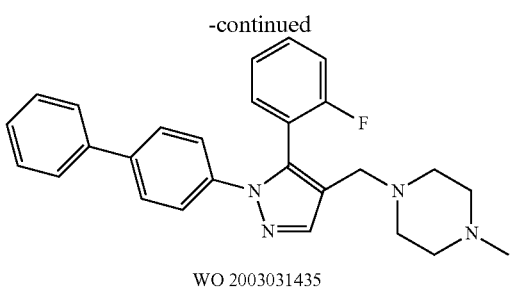
WO 2003031435
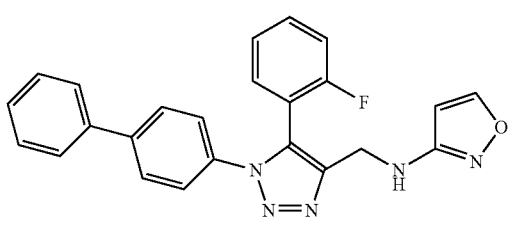
DE 10315570
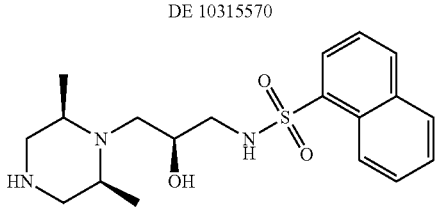
WO 2003055478
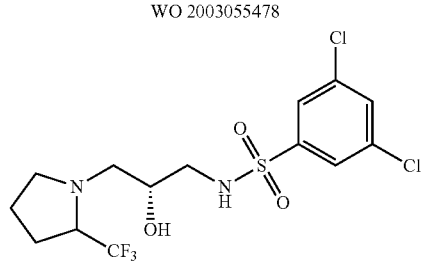
WO 2004113280
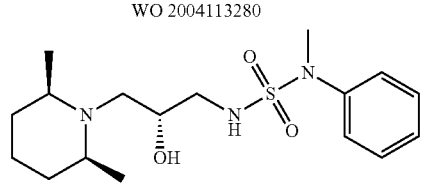
WO 2004112787
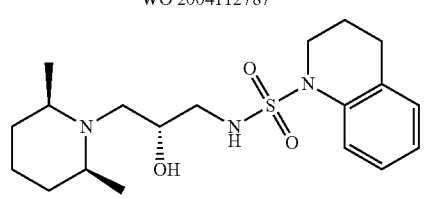
WO 2004113301
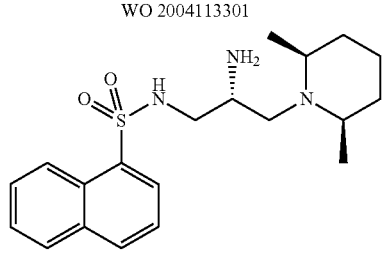
WO 2005049023
-continued
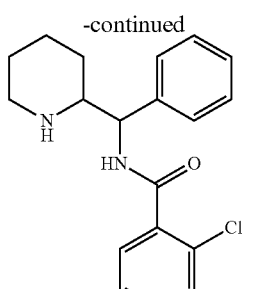
WO 2003089411
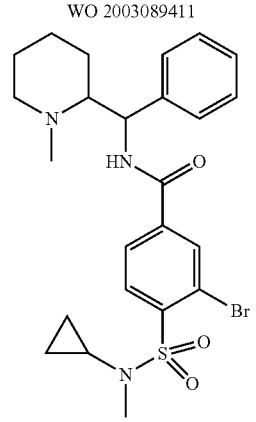
WO 2004013100
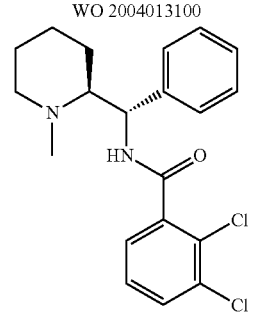
WO 2004013101
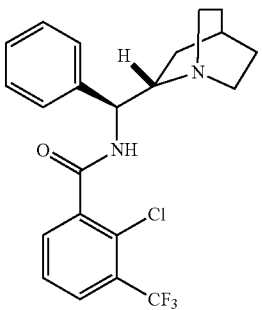
WO 2005037783
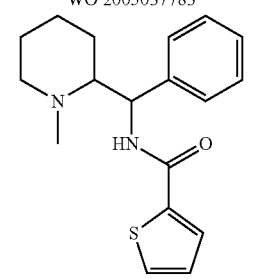
WO 2005037792

-continued
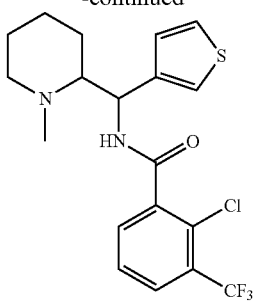
WO 2005037781
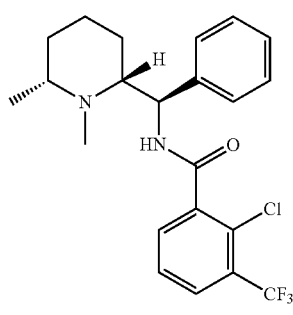
WO 2005037782
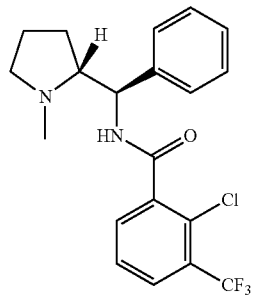
WO 2005037785
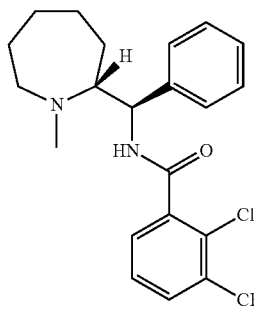
WO 2005037785
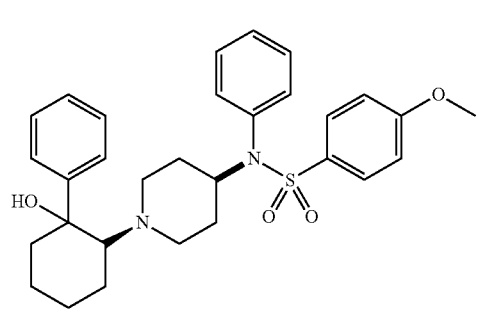
WO 2004072034
-continued
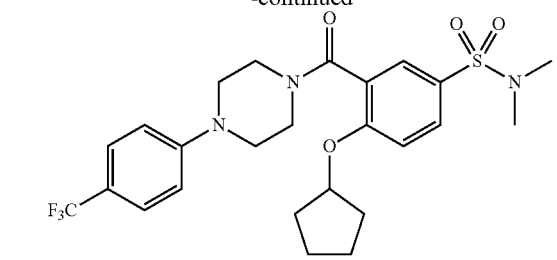
WO 2005014563
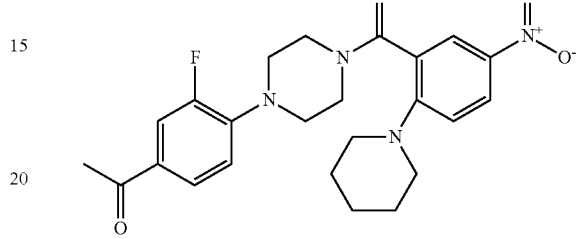
WO 2005023260
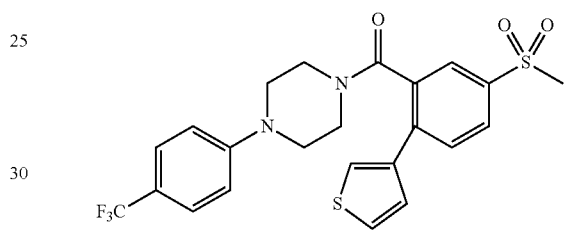
WO 2005023261
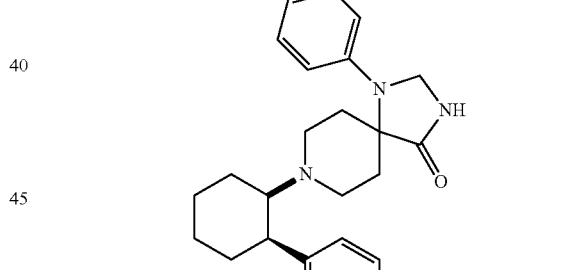
WO 2005040166
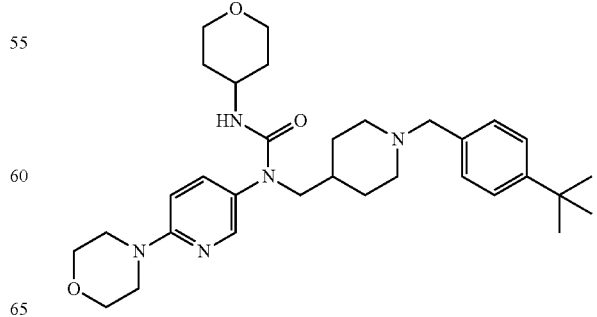
WO 2005058882

-continued

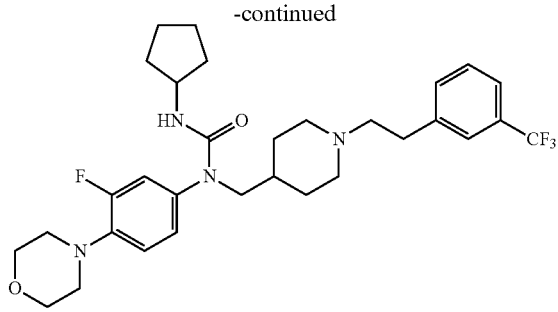

WO 2005058885

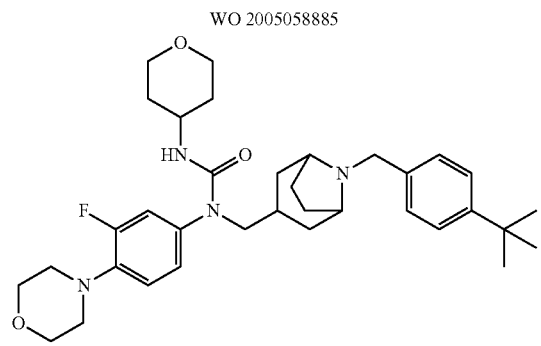

WO 2005058317

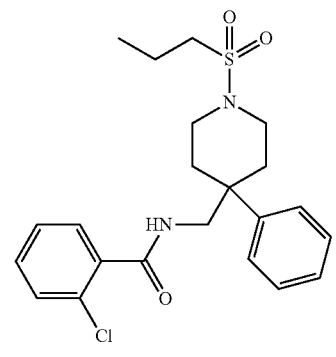

WO 2005046601

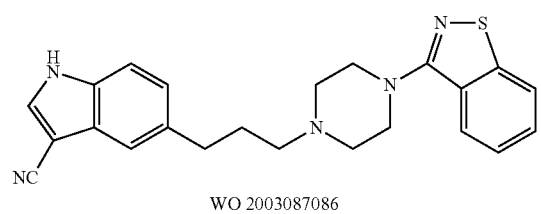

WO 2003087086

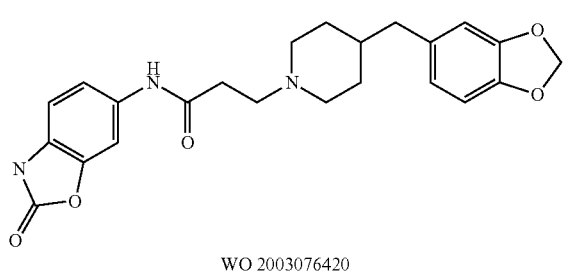

WO 2003076420

-continued

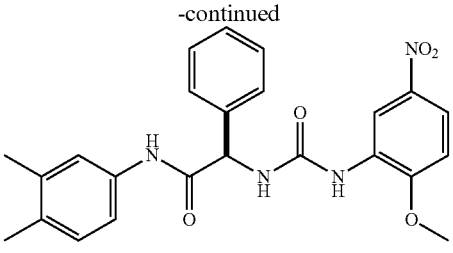

WO 2004022528

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to phenalkylamine derivatives of the formula (I)

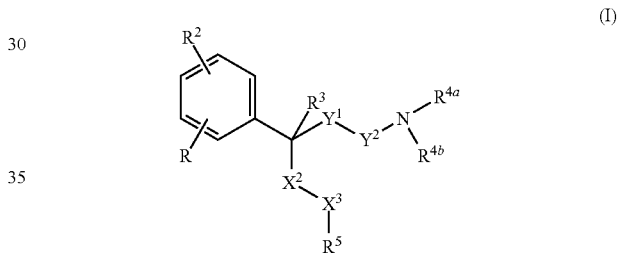

(I)

wherein
R is $R^1$—W—$A^1$-Q-Y-$A^2$-$X^1$—;
$R^1$ is hydrogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl) aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl) sulfonylamino, arylsulfonylamino or optionally substituted heterocyclyl;

W is —NR$^8$— or a bond;
A$^1$ is optionally substituted alkylene or a bond;
Q is —S(O)$_2$— or —C(O)—;
Y is —NR$^9$— or a bond;
A$^2$ is optionally substituted alkylene, alkylene-CO—, —CO-alkylene, alkylene-O-alkylene, alkylene-NR$^{10}$-alkylene, optionally substituted alkenylene, optionally substituted alkynylene, optionally substituted arylene, optionally substituted heteroarylene or a bond;
X$^1$ is —O—, —NR$^{11}$—, —S—, optionally substituted alkylene, optionally substituted alkenylen, optionally substituted alkynylene;
R$^2$ is hydrogen, halogen, alkyl, halogenated alkyl, hydroxyalkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals R$^2$ together with the ring atoms to which they are bound form a 5- or 6-membered ring;
R$^3$ is hydrogen or alkyl;
X$^2$ is —O—, —NR$^6$—, —S—, >CR$^{12a}$R$^{12b}$ or a bond;
X$^3$ is —O—, —S—, >CR$^{13a}$R$^{13b}$ or a bond;
R$^5$ is optionally substituted aryl, optionally substituted cycloalkyl or optionally substituted heterocyclyl;
Y$^1$ is >CR$^{14a}$R$^{14b}$ or a bond;
Y$^2$ is >CR$^{15a}$R$^{15b}$ or a bond;
R$^{4a}$ is hydrogen, alkyl, cycloalkylalkyl, halogenated alkyl, hydroxyalkyl, alkoxyalkyl, aminoalkyl, CH$_2$CN, arylalkyl, cycloalkyl, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl;
R$^{4a}$, R$^3$ together are optionally substituted alkylene; or
R$^{4a}$, R$^{14a}$ together are optionally substituted alkylene; or
R$^{4b}$ is hydrogen, alkyl, halogenated alkyl, hydroxyalkyl, alkoxyalkyl, aminoalkyl, CH$_2$CN, cycloalkyl, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl; or
R$^{4a}$, R$^{4b}$
together are optionally substituted alkylene, wherein one —CH$_2$— of alkylene may be replaced by an oxygen atom or —NR$^{16}$;
R$^6$ is hydrogen or alkyl;
R$^7$ is hydrogen or alkyl;
R$^8$ is hydrogen or alkyl;
R$^9$ is hydrogen, alkyl, cycloalkyl, aminoalkyl, optionally substituted arylalkyl or heterocyclyl; or
R$^9$, R$^1$
together are alkylene; or
R$^9$ is alkylene that is bound to a carbon atom in A$^2$ and A$^2$ is alkylene or to a carbon atom in X$^1$ and X$^1$ is alkylene;
R$^{10}$ is hydrogen, alkyl or alkylsulfonyl;
R$^{11}$ is hydrogen or alkyl, or
R$^9$, R$^{11}$
together are alkylene,
R$^{12a}$ is hydrogen, optionally substituted alkyl, alkylaminoalkyl, dialkylaminoalkyl, heterocyclylalkyl, optionally substituted aryl or hydroxy;
R$^{12b}$ is hydrogen or alkyl, or
R$^{12a}$, R$^{12b}$
together are carbonyl or optionally substituted alkylene, wherein one —CH$_2$— of alkylene may be replaced by an oxygen atom or —NR$^{17}$—;

R$^{13a}$ is hydrogen, optionally substituted alkyl, alkylaminoalkyl, dialkylaminoalkyl, heterocyclylalkyl, optionally substituted aryl or hydroxy;
R$^{13b}$ is hydrogen or alkyl, or
R$^{13a}$, R$^{13b}$
together are carbonyl or optionally substituted alkylene, wherein one —CH$_2$— of alkylene may be replaced by an oxygen atom or —NR$^{18}$—;
R$^{14a}$ is hydrogen, optionally substituted alkyl, alkylaminoalkyl, dialkylaminoalkyl, C$_3$-C$_{12}$-heterocyclylalkyl, optionally substituted aryl or hydroxy;
R$^{14b}$ is hydrogen or alkyl, or
R$^{14a}$, R$^{14b}$
together are carbonyl or optionally substituted alkylene which may contain one or two heteroatoms independently selected from oxygen or nitrogen;
R$^{15a}$ is hydrogen, optionally substituted alkyl, alkylaminoalkyl, dialkylaminoalkyl, heterocyclylalkyl, optionally substituted aryl or hydroxy;
R$^{15b}$ is hydrogen or C$_1$-C$_6$-alkyl, or
R$^{15a}$, R$^{15b}$
together are carbonyl or optionally substituted alkylene which may contain one or two heteroatoms independently selected from oxygen or nitrogen;
R$^{16}$ is hydrogen or C$_1$-C$_6$-alkyl;
R$^{17}$ is hydrogen or C$_1$-C$_6$-alkyl; and
R$^{18}$ is hydrogen or C$_1$-C$_6$-alkyl,
or a physiologically tolerated salt thereof.

Thus, the present invention relates to phenalkylamine derivatives having the formula (Ia)

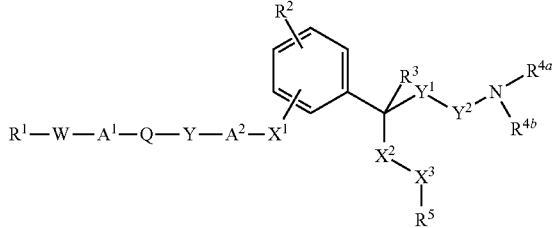

(Ia)

wherein R$^1$, W, A$^1$, Q, Y, A$^2$, X$^1$, R$^2$, R$^3$, X$^2$, X$^3$, R$^5$, Y$^1$, Y$^2$, R$^{4a}$, R$^{4b}$ are as defined herein.

Thus, the term phenalkylamine derivative is used herein to denote in particular phenethylamines (Y$^1$ is a bond) and phenpropylamines (Y$^1$ is >CR$^{14a}$R$^{14b}$).

Said compounds of formula (I), i.e., the phenalkylamine derivatives of formula (I) and their physiologically tolerated salts, are glycine transporter inhibitors and thus useful as pharmaceuticals.

The present invention thus further relates to the compounds of formula (I) for use in therapy.

The present invention also relates to pharmaceutical compositions which comprise a carrier and a compound of formula (I).

In particular, said compounds, i.e., the phenalkylamine derivatives and their physiologically tolerated salts, are inhibitors of the glycine transporter GlyT1.

The present invention thus further relates to the compounds of formula (I) for use in inhibiting the glycine transporter.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention further relates to the compounds of formula (I) for use in treating pain.

The present invention also relates to the use of the compounds of formula (I) in the manufacture of a medicament for treating a neurologic or psychiatric disorder and corresponding methods of treating said disorders. The present invention also relates to the use of the compounds of formula (I) in the manufacture of a medicament for treating pain and corresponding methods of treating pain.

DETAILED DESCRIPTION OF THE INVENTION

Provided that the phenalkylamine derivatives of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts.

According to one embodiment, an enantiomer of the phenalkylamine derivatives of the present invention has the following formula:

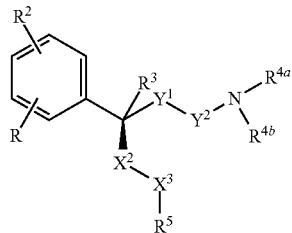

wherein R, $A^2$, $R^3$, $X^2$, $X^3$, $R^5$, $Y^1$, $Y^2$, $R^{4a}$, $R^{4b}$ are as defined herein.

According to another embodiment, an enantiomer of the phenalkylamine derivatives of the present invention has the following formula:

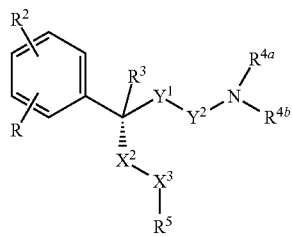

wherein R, $R^2$, $R^3$, $X^2$, $X^3$, $R^5$, $Y^1$, $Y^2$, $R^{4a}$, $R^{4b}$ are as defined herein.

The physiologically tolerated salts of the phenalkylamine derivatives of the formula (I) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. The physiologically tolerated salts of the phenalkylamine derivatives also include salts of a physiologically tolerated anion with an phenalkylamine derivatives wherein one or more than one nitrogen atom is quaternized, e.g. with an alkyl residue (e.g. methyl or ethyl).

The present invention moreover relates to compounds of formula (I) as defined herein, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, such compounds contain more of the respective isotope than this naturally occurs and thus is anyway present in the compounds (I).

Stable isotopes (e.g., deuterium, $^{13}C$, $^{15}N$, $^{18}O$) are nonradioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic Press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D Metal., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$-$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1$-$C_4$-alkoxy -$C_1$-$C_4$-alkyl, amino-$C_1$-$C_4$-alkyl, $C_1$-$C_4$-alkenyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, $NH_2$, NH—$C_1$-$C_6$-alkyl, N—($C_1$-$C_6$-alkyl)$_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2NH$—$C_6$-$C_{12}$-aryl, CONH—$C_3$-$C_{12}$-heterocyclyl, $SO_2NH$—$C_3$-$C_{12}$-heterocyclyl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl, oxo (=O) being a further substituent, wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, iso-butylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonyl amino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, isopropylsulfonylaminomethyl, n-butylsulfonylaminomethyl, 2-butylsulfonylaminomethyl, isobutylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene. A further example is propylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, isobutoxy(2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, isopropylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a di-alkylamino group'having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, iso-propylcarbonylaminomethoxy, n-butylcarbonylaminomethoxy, 2-butylcarbonylaminomethoxy, iso-butylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(isobutylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, isobutoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(isopropoxycarbonylamino)ethoxy, 2-(n-butoxycarbonylamino)ethoxy, 2-(2-butoxycarbonylamino)ethoxy, 2-(isobutoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy(2-propen-1-yloxy), 1-propen-1-yloxy, 2-propen-2-yloxy, methallyloxy (2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_5$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein.

Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl, tertbutylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido (methylcarbonylamino), propionamido, n-butyramido, 2-methylpropionamido (isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino(2-propen-1-ylamino), 1-propen-1-ylamino, 2-propen-2-ylamino, methallylamino(2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, isopropylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6- yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetra-hydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro 1,4-thiazin 5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene.

With respect to the compounds' capability of inhibiting glycine transporter 1, the variables $R^1$, W, $A^1$, Q, Y, $A^2$, $X^1$, $R^2$, $R^3$, $X^2$, $X^3$, $R^5$, $Y^1$, $Y^2$, $R^{4a}$, $R^{4b}$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{20}$ preferably have the following meanings which, when taken alone or in combination, represent particular embodiments of the phenalkylamine derivatives of the formula (I) or any other formula disclosed herein.

In said formula (I), there may be one or more than one substituent R and/or $R^2$. More particularly, there may be up to 4 substituents $R^2$. Preferably there is one substituent R and 1, 2, 3 or 4 substituents $R^2$. Formula (I) may thus be depicted as follows:

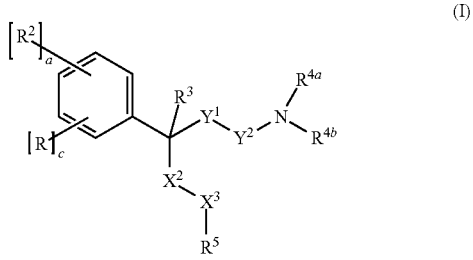

(I)

wherein a is 1, 2, 3 or 4, and c is 1. If there is more than one radical $R^2$, these may be the same or different radicals.

$R^1$ is hydrogen, $C_1$-$C_6$-alkyl (e.g. methyl, ethyl, n-propyl, isopropyl, n-butyl, sec-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)silyl-$C_1$-$C_4$-alkyl (e.g. trimethylsilylethyl), hydroxy-$C_1$-$C_4$-alkyl, $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl (e.g. cyclopropyl or cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl (e.g. prop-1,2-en-1-yl), $C_2$-$C_6$-alkynyl, optionally substituted $C_6$-$C_{12}$-aryl (e.g. phenyl, 2-methylphenyl), hydroxy, $C_1$-$C_6$-alkoxy (e.g. tert-butyloxy), halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino (e.g. dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl, 3-pyrrolidinyl, 1-methyl-pyrrol-3-yl, 2-pyridyl, 1-methyl-1,2-diazol-3-yl, 1-methyl-3-trifluoromethyl-1,2-diazol-4-yl, 1,2-dimethyl-1,3-diazol-4-yl, 5-methylisoxazol-3-yl or 1-methyl-1,2,4-triazol-3-yl).

Preferably, $R^1$ is $C_1$-$C_6$-alkyl (e.g. methyl, ethyl, n-propyl, isopropyl, sec-butyl, n-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl).

In particular, $R^1$ is $C_1$-$C_6$-alkyl (e.g. n-propyl), $C_3$-$C_{12}$-cycloalkyl-$C_1$-$C_4$-alkyl (e.g. cyclopropylmethyl), halogenated $C_1$-$C_6$-alkyl (e.g. 3-fluoroprop-1-yl), or optionally substituted $C_3$-$C_{12}$-heterocyclyl (e.g. 1-methyl-1,2-diazol-4-yl, 1-methyl-1,3-diazol-4-yl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, piperidinyl, piperazinyl or morpholinyl, pyrrolyl, isoxazolyl and triazolyl being further examples of such $C_3$-$C_{12}$-heterocyclyl, substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl). The same applies to substituted $C_3$-$C_{12}$-heteroaryl in substituted $C_3$-$C_{12}$-heteroaryl-$C_1$-$C_4$-alkyl.

According to one embodiment, W is —$NR^8$— and Y is a bond. According to an alternative embodiment, W is a bond and Y is —$NR^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —$S(O)_2$—. According to an alternative embodiment, Q is —$C(O)$—.

According to a particular embodiment, —W-$A^1$-Q-Y— is —W-$A^1$-$S(O)_2$—$NR^9$—, —$NR^8$—$S(O)_2$—, -$A^1$-$S(O)_2$— or —$S(O)_2$—. According to a further particular embodiment, —W-$A^1$-Q-Y— is —W-$A^1$-CO—$NR^9$— or —$NR^8$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —$NR^8$—.

$A^2$ is optionally substituted $C_1$-$C_4$-alkylene (e.g. 1,2-ethylene or 1,3-propylene), $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond. Additionally, $A^2$ may be optionally substituted $C_2$-$C_4$-alkenylen or optionally substituted $C_2$-$C_4$-alkynylene. Preferably, $A^2$ is optionally substituted $C_1$-$C_4$-alkylene (e.g. 1,2-ethylene or 1,3-propylene). More preferably, $A^2$ is $C_1$-$C_4$-alkylene (e.g. 1,2-ethylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, $X^1$ is preferably optionally substituted $C_1$-$C_4$-alkylene. Alternatively, if $A^2$ is a bond, $X^1$ is in particular optionally substituted $C_2$-$C_4$-alkenylene or optionally substituted $C_2$-$C_4$-alkynylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g. morpholino or piperidinyl).

$X^1$ is —O—, —$NR^{11}$—, —S— or optionally substituted $C_1$-$C_4$-alkylene (e.g. —$CH_2$—, 1,2-ethylene and 1,3-popylene). In connection with $X^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Additionally, $X^1$ may be optionally substituted $C_2$-$C_4$-alkenylen or optionally substituted $C_2$-$C_4$-alkynylene (e.g. propynylene). In connection with $X^1$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano. Preferably, $X^1$ is —O—, —$NR^{11}$, or —S—. More preferably, $X^1$ is —O—. Alternatively, it is preferred if $X^1$ is optionally substituted $C_1$-$C_4$-alkylene (e.g. —$CH_2$—).

According to a particular embodiment, $A^2$ is a bond and $X^1$ is optionally substituted $C_1$-$C_4$-alkylene, optionally substituted $C_2$-$C_4$-alkenylene or optionally substituted $C_2$-$C_4$-alkynylene.

According to a particular embodiment, $R^1$—W-$A^1$-Q-Y-$A^2$-$X^1$— is $R^1$—$S(O)_2$—NH-$A^2$-$X^1$—, $R^1$—NH—$S(O)_2$-$A^2$-$X^1$—, $R^1$—C(O)—NH-$A^2$-$X^1$— or $R^1$—NH—C(O)-$A^2$-$X^1$—.

According to a particular embodiment, the structural element —Y-$A^2$-$X^1$— comprises at least 2, 3 or 4 atoms in the main chain. According to further particular embodiments the structural element —Y-$A^2$-$X^1$— has up to 4, 5 or 6 atoms in the main chain, such as 2 to 6, 2 to 5, or 2 to 4 atoms in the main chain, or especially 2, 3 or 4 atoms in the main chain.

According to a further particular embodiment —Y-$A^2$-$X^1$— is —$C_1$-$C_4$-alkylene-O— or —$NR^9$—$C_1$-$C_4$-alkylene-O—, with —Y-$A^2$-$X^1$— preferably having 2 to 6, 3 to 5, or especially 4 atoms in the main chain. Particular examples of —Y-$A^2$-$X^1$— include —$(CH_2)_3$—O— and —$NR^9$—$(CH_2)_2$—O—. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl), or $R^9$ is $C_1$-$C_4$-alkylene that is bound to a carbon atom in $A^2$ which is $C_1$-$C_4$-alkylene.

According to a further particular embodiment, —Y-$A^2$-$X^1$— is —$NR^9$—$C_1$-$C_4$-alkylene- (e.g. —NH—$CH_2$—, —NH—$(CH_2)_2$— or —NH—$(CH_2)_3$—), with —Y-$A^2$-$X^1$— preferably having 2 to 6, 2 to 5, 2 to 4, or especially 2, 3 or 4 atoms in the main chain. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl); or $R^9$ is $C_1$-$C_4$-alkylene that is bound to a carbon atom in $X^1$ which is $C_1$-$C_4$-alkylene.

According to a further particular embodiment, —Y-$A^2$-$X^1$— is —$NR^9$—$C_2$-$C_4$-alkenylene- or —$NR^9$—$C_2$-$C_4$-alkynylene- (e.g. —NH—$CH_2$—C≡C—), with —Y-$A^2$-$X^1$— preferably having 2 to 6, 3 to 5, or especially 4 atoms in the main chain. In this particular embodiment, $R^9$ is as defined herein and preferably is $R^9$ is hydrogen, $C_1$-$C_6$-alkyl (e.g. methyl or ethyl) or $C_3$-$C_{12}$-cycloalkyl (e.g. cyclopropyl or cyclobutyl).

According to a further particular embodiment, —Y-$A^2$-$X^1$— is —$C_1$-$C_4$-alkylene- (e.g. —$(CH_2)_2$—), with —Y-$A^2$-$X^1$— preferably having 2 to 6, 2 to 5, 2 to 4, or especially 2 atoms in the main chain.

According to a further particular embodiment, the structural motif —Y-A²-X¹— as disclosed herein is bound to Q being —S(O)₂— or —C(O)—. Particular examples for this embodiment include phenalkylamine derivatives of the invention wherein R is R¹—S(O)₂—Y-A²-X¹— or R¹—C(O)—Y-A²-X¹—.

The radical R (i.e. the radical R¹—W-A¹-Q-Y-A²-X¹—) may, in principle, be bound to the phenyl moiety in ortho-, meta- or para-position with respect to the alkylamine moiety:

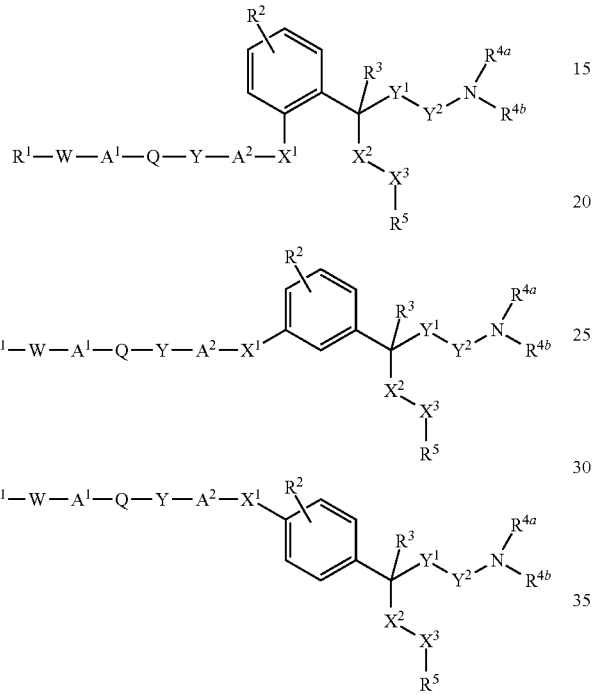

In said formulae, R¹, W, A¹, Q, Y, A², X¹, R², R³, Y¹, Y², R⁴ᵃ, R⁴ᵇ, X², X³, R⁵ are as defined herein.

Particularly preferred are phenalkylamine derivatives having the radical R¹—W-A¹-Q-Y-A²-X¹— in the meta-position (with respect to the alkylamine moiety).

In addition to the radical R¹—W-A¹-Q-Y-A²-X¹—, the phenalkylamine derivatives of the invention may have one or more than one further substituent bound to the benzene ring. In these positions, the skeleton of the phenalkylamine derivatives may thus be substituted with one or more than one radical R². If there is more than one radical R², these may be the same or different radicals. The phenalkylamine derivatives of the invention may therefore be represented by one of the following formulae:

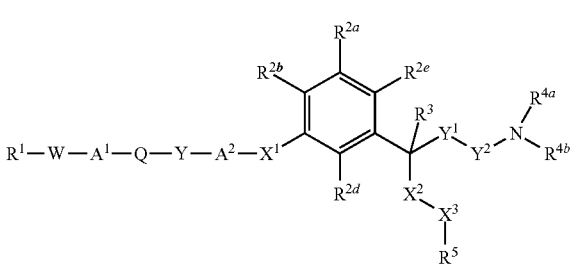

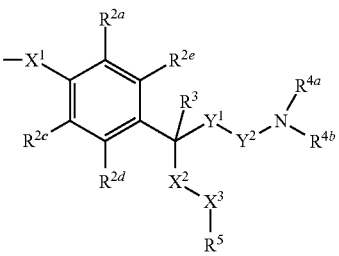

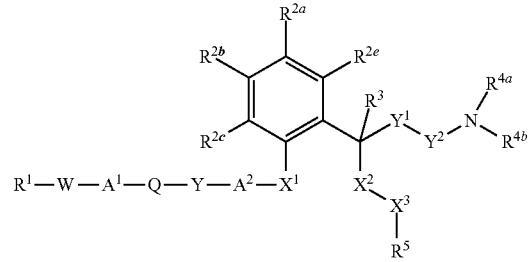

wherein R²ᵃ, R²ᵇ, R²ᶜ, R²ᵈ, R²ᵉ independently have one of the meanings given for R², and R¹, W, A¹, Q, Y, A², X¹, R³, X², X³, R⁵, Y¹, Y², R⁴ᵃ, R⁴ᵇ are as defined herein.

R² is hydrogen, halogen (e.g. fluorine), C₁-C₆-alkyl, halogenated C₁-C₄-alkyl, hydroxy-C₁-C₄-alkyl, —CN, C₂-C₆-alkenyl, C₂-C₆-alkynyl, optionally substituted C₆-C₁₂-aryl, hydroxy, C₁-C₆-alkoxy, halogenated C₁-C₆-alkoxy, C₁-C₆-alkoxycarbonyl, C₂-C₆-alkenyloxy, C₆-C₁₂-aryl-C₁-C₄-alkoxy, C₁-C₆-alkylcarbonyloxy, C₁-C₆ alkylthio, C₁-C₆-alkylsulfinyl, C₁-C₆-alkylsulfonyl, aminosulfonyl, amino, C₁-C₆-alkylamino, C₂-C₆-alkenylamino, nitro or optionally substituted C₃-C₁₂-heterocyclyl, or two radicals R² together with the ring atoms to which they are bound form a 5- or 6 membered ring.

An optionally substituted 5- or 6-membered ring that is formed by two radicals R² together with the ring atoms of the benzene ring to which they are bound is, for instance, a benzene ring.

In connection with R², substituted C₆-C₁₂-aryl in particular includes C₆-C₁₂-aryl, such as phenyl, substituted with 1, 2 or 3 substituents selected from the group consisting of halogen and C₁-C₄-alkyl, C₁-C₄-haloalkyl, cyano, C₁-C₄-alkoxy and C₁-C₄-haloalkoxy.

In connection with R², substituted C₃-C₁₂-heterocyclyl in particular includes C₃-C₁₂-heterocyclyl, such as morpholinyl, pyrrolidinyl and piperidinyl, substituted with 1, 2 or 3 substituents selected from the group consisting of halogen, C₁-C₄-alkyl, C₁-C₄-haloalkyl, cyano, C₁-C₄-alkoxy and C₁-C₄-haloalkoxy.

Preferably, R² is hydrogen, halogen (e.g. fluorine) or C₁-C₆-alkoxy. In particular, R² is hydrogen or halogen (e.g. fluorine).

According to a particular embodiment, the phenalkylamine derivatives of the invention have one of the following formulae:

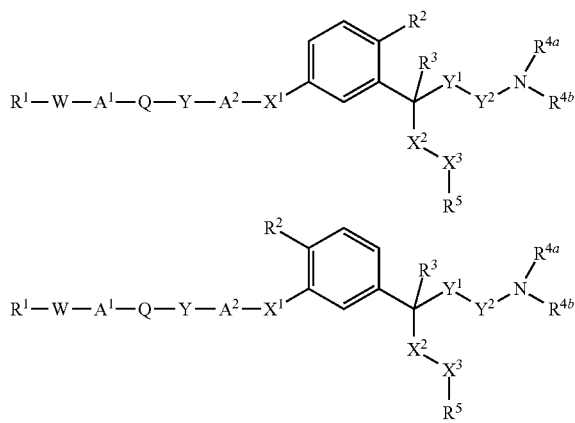

wherein $R^1$, W, $A^1$, Q, Y, $A^2$, $X^1$, $R^2$, $R^3$, $X^2$, $X^3$, $R^5$, $Y^1$, $Y^2$, $R^{4a}$, $R^{4b}$ are as defined herein.

$R^3$ is hydrogen or $C_1$-$C_6$-alkyl. In particular, $R^3$ is hydrogen.

$X^2$ is —O—, —$NR^6$—, —S—, >$CR^{12a}R^{12b}$ or a bond. Preferably, $X^2$ is >$CR^{12a}R^{12b}$.

$X^3$ is —O—, —S—, >$CR^{13a}R^{13b}$ or a bond. Preferably, $X^3$ is a bond.

Thus, it is preferred if $X^2$ is >$CR^{12a}R^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{12a}$ is hydrogen or $C_1$-$C_6$-alkyl.

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{13a}$ is hydrogen or $C_1$-$C_6$-alkyl.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_6$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together are together are carbonyl or, preferably, optionally substituted $C_1$-$C_4$-alkylene (e.g. 1,3-propylene), wherein one —$CH_2$— of $C_1$-$C_4$-alkylene may be replaced by an oxygen atom or —$NR^{17}$— or $NR^{18}$.

In connection with $R^{12a}$ and $R^{12b}$, or $R^{13a}$ and $R^{13b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is $C_1$-$C_6$-alkyl and $R^{12b}$ is hydrogen or $C_1$-$C_6$-alkyl, or $R^{13a}$ is $C_1$-$C_6$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted 1,3-propylene, or $R^{13a}$ and $R^{13b}$ together are optionally substituted 1,3-propylene.

$R^5$ is optionally substituted $C_6$-$C_{12}$-aryl (e.g. phenyl, 2-fluorophenyl, 3-fluorophenyl, 3-chlorophenyl, 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 2,4-dichlorophenyl or 3,4-dichlorophenyl,), optionally substituted $C_3$-$C_{12}$-cycloalkyl (e.g. cyclohexyl) or optionally substituted $C_3$-$C_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_3$-$C_{12}$-heterocyclyl in particular includes $C_3$-$C_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, $C_3$-$C_{12}$-heterocyclyl in particular is $C_3$-$C_{12}$-heteroaryl.

Preferably, $R^5$ is optionally substituted $C_6$-$C_{12}$-aryl, in particular as in the phenalkylamine derivatives of the formula:

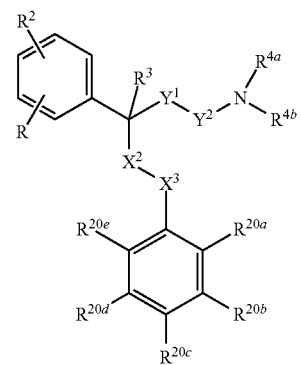

wherein R, $R^2$, $R^3$, $X^2$, $X^3$, $Y^1$, $Y^2$, $R^{4a}$, $R^{4b}$ are as defined herein, and $R^{20a}$, $R^{20b}$, $R^{20c}$, $R^{20d}$, $R^{20e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

It is also preferred if $R^5$ is optionally substituted $C_6$-$C_{12}$-heteroaryl, in particular as in the phenalkylamine derivatives of the formula:

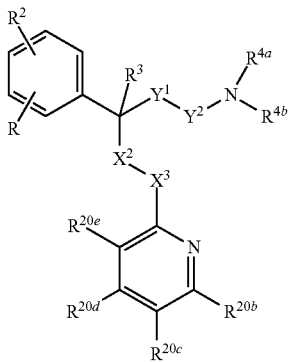

wherein R, $R^2$, $R^3$, $X^2$, $X^3$, $Y^1$, $Y^2$, $R^{4a}$, $R^{4b}$ are as defined herein, and $R^{20b}$, $R^{20c}$, $R^{20d}$, $R^{20e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

According to a particular embodiment, the invention relates to phenalkylamine derivatives of the formula:

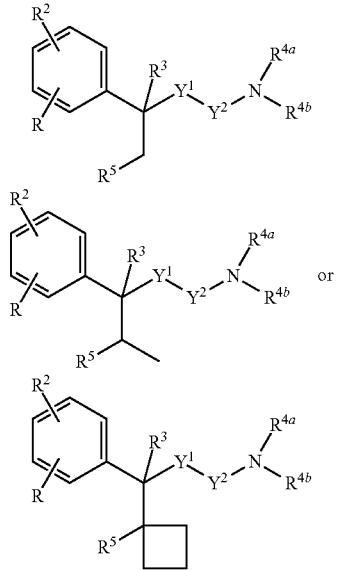

wherein R, $R^2$, $R^3$, $R^5$, $Y^1$, $Y^2$, $R^{4a}$, $R^{4b}$ are as defined herein, $R^5$ preferably being optionally substituted aryl and in particular optionally substituted phenyl as disclosed herein.

In connection with $R^5$ or $R^{20a}$, $R^{20b}$, $R^{20c}$, $R^{20d}$, $R^{20e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $C_3$-$C_{12}$-heterocyclyl (e.g. morpholinyl or piperidinyl).

According to a particular embodiment, $R^{20a}$, $R^{20b}$, $R^{20d}$, $R^{20e}$ are hydrogen and $R^{20c}$ is different from hydrogen (para-mono-substitution).

According to a further particular embodiment, $R^{20a}$, $R^{20c}$, $R^{20d}$, $R^{20e}$ are hydrogen and $R^{20b}$ is different from hydrogen (meta-mono-substitution).

In connection with $R^{20a}$, $R^{20b}$, $R^{20c}$, $R^{20d}$, $R^{20e}$, $C_3$-$C_{12}$-heterocyclyl in particular includes morpholinyl, imidazolyl and pyrazolyl.

$Y^1$ is a bond or $>CR^{14a}R^{14b}$. According to one embodiment, $Y^1$ is a bond.

$Y^2$ is $>CA^{15a}R^{15b}$ or a bond.

Thus, according to one embodiment —$Y^1$—$Y^2$— is $>CR^{15a}R^{15b}$ and according to another embodiment —$Y^1$—$Y^2$— is a bond.

$R^{14a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxyl.

$R^{14b}$ is hydrogen or $C_1$-$C_6$-alkyl.

Alternatively, $R^{14a}$, $R^{14b}$ together are carbonyl or optionally substituted alkylene which may contain one or two heteroatoms independently selected from oxygen or nitrogen, i.e. $R^{14a}$, $R^{14b}$ together are carbonyl or optionally substituted $C_1$-$C_4$-alkylene, wherein one or two —$CH_2$— of $C_1$-$C_4$-alkylene may be replaced by an oxygen atom or —$NR^{19}$—.

$R^{15a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxyl.

$R^{15b}$ is hydrogen or $C_1$-$C_6$-alkyl.

According to a particular embodiment, $R^{15a}$ is hydrogen and $R^{15b}$ is hydrogen.

Alternatively, $R^{15a}$, $R^{15b}$ together are carbonyl or optionally substituted alkylene which may contain one or two heteroatoms independently selected from oxygen or nitrogen, i.e. $R^{15a}$, $R^{15b}$ together are carbonyl or optionally substituted $C_1$-$C_4$-alkylene, wherein one or two —$CH_2$— of $C_1$-$C_4$-alkylene may be replaced by an oxygen atom or —$NR^{19}$—.

In connection with $R^{14a}$ and $R^{14b}$, or $R^{15a}$ and $R^{153b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

$R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), hydroxy-$C_1$-$C_4$-alkyl, $C_1$-$C_6$-alkoxy-$C_1$-$C_4$-alkyl, amino-$C_1$-$C_4$-alkyl, $C_3$-$C_{12}$—$CH_2CN$, $C_6$-$C_{12}$-aryl-$C_1$-$C_4$-alkyl (e.g. benzyl), cycloalkyl (e.g. cyclopropyl), —CHO, $C_1$-$C_4$-alkylcarbonyl (e.g. methylcarbonyl, ethylcarbonyl or isopropylcarbonyl), (halogenated $C_1$-$C_4$-alkyl)carbonyl (e.g. fluoromethylcarbonyl, difluoromethylcarbonyl, trifluoromethylcarbonyl, 1,1,1-trifluoroeth-2-ylcarbonyl or 1,1,1-trifluoroprop-3-ylcarbonyl), $C_6$-$C_{12}$-arylcarbonyl (e.g. phenylcarbonyl), $C_1$-$C_4$-alkoxycarbonyl (e.g. ethoxycarbonyl or tertbutyloxycarbonyl), $C_6$-$C_{12}$-aryloxycarbonyl (e.g. phenoxycarbonyl), $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl (e.g. 3-oxetanyl).

Preferably, $R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), amino-$C_1$-$C_4$-alkyl, $CH_2CN$, $C_6$-$C_{12}$-aryl-$C_1$-$C_4$-alkyl (e.g. benzyl), cycloalkyl (e.g. cyclopropyl), $C_1$-$C_4$-alkylcarbonyl (e.g. methylcarbonyl or isopropylcarbonyl), (halogenated $C_1$-$C_4$-alkyl)carbonyl (e.g. fluoromethylcarbonyl, difluoromethylcarbonyl or trifluoromethylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl), —C(=NH)NH$_2$, —C(=NH)NHCN, $C_1$-$C_6$-alkylsulfonyl, amino, —NO or $C_3$-$C_{12}$-heterocyclyl (e.g. 3-oxetanyl).

In particular, $R^{4a}$ is hydrogen, $C_1$-$C_6$-alkyl (e.g. methyl), $C_6$-$C_{12}$-aryl-$C_1$-$C_4$-alkyl (e.g. benzyl), cycloalkyl (e.g. cyclopropyl), or $C_1$-$C_4$-alkoxycarbonyl (e.g. tert-butyloxycarbonyl).

Alternatively, $R^{4a}$ and $R^3$ together are optionally substituted $C_1$-$C_4$-alkylene (e.g. methylene or 1,2 ethylene, a further example being 1,3-propylene, 1-oxo-1,2-ethylene, 1-oxo-1,3-propylene) so that $R^{4a}$ and $R^3$ together with the —$Y^1$—$Y^2$—N— moiety and the C atom to which $R^3$ is bound form an heterocyclic ring having, in particular, 4, 5, or 6 ring member atoms (including the nitrogen atom). With $R^{4a}$ and $R^3$ together being optionally substituted $C_1$-$C_4$-alkylene, such phenalkylamine derivatives may be represented by the following partial structure:

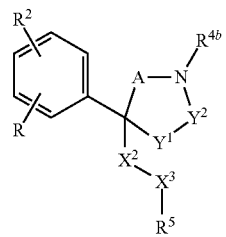

wherein A is optionally substituted $C_1$-$C_4$-alkylene (e.g. methylene or 1,2-ethylene, a further example being 1,3-propylene, 1-oxo-1,2-ethylene, 1-oxo-1,3-propylene) and R, $R^2$, $X^2$, $X^3R^5$, $Y^1$, $Y^2$, $R^{4b}$ are as defined herein, with —$Y^1$—$Y^2$— in particular being >$CR^{15a}R^{15b}$ (e.g. methylene).

In connection with $R^{4a}$ and $R^3$, substituted $C_1$-$C_4$-alkylene in particular includes $C_1$-$C_4$-alkylene substituted with 1, 2 or 3 substituents selected from the group consisting of halogen (e.g. fluoro), $C_1$-$C_4$-alkyl or oxo.

Alternatively, $Y^1$ is >$CR^{14a}R^{14b}$ and $R^{4a}$ and $R^{14a}$ together are optionally substituted $C_1$-$C_4$-alkylene (e.g. methylene) so that $R^{4a}$ and $R^{14a}$ together with the —$C(R^{14b})$—$Y^2$—N— moiety is bound form an heterocyclic ring having, in particular, 4, 5, or 6 ring member atoms (including the nitrogen atom). With $R^{4a}$ and $R^{14a}$ together being $C_1$-$C_4$-alkylene, such a ring may be represented by the following partial structure:

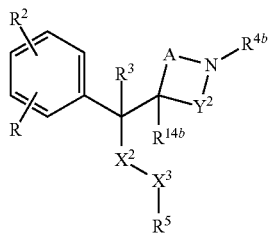

wherein A is optionally substituted $C_1$-$C_4$-alkylene (e.g. methylene) and R, $R^2$, $R^3$, $X^2$, $X^3$, $R^5$, $R^{14b}$, $Y^2$, $R^{4a}$ are as defined herein, with —$Y^2$— in particular being >$CR^{15a}R^{15b}$.

In connection with $R^{4a}$ and $R^{14a}$, substituted $C_1$-$C_4$-alkylene in particular includes $C_1$-$C_4$-alkylene substituted with 1, 2 or 3 substituents selected from the group consisting halogen (e.g. fluoro), $C_1$-$C_4$-alkyl or oxo.

$R^{4b}$ is hydrogen, $C_1$-$C_6$-alkyl (e.g. methyl, ethyl), halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl.

In particular, $R^{4b}$ is hydrogen or $C_1$-$C_6$-alkyl (e.g. methyl, ethyl) or, especially if $R^{4a}$ and $R^3$ together are optionally substituted $C_1$-$C_4$-alkylene, $R^{4b}$ is hydrogen, $C_1$-$C_6$-alkyl (e.g. methyl, ethyl, 2-propyl, 2,2,2-trimethylethyl), halogenated $C_1$-$C_4$-alkyl (e.g. 2-fluoroethyl, 2,2-difluoroethyl, 2,2,2-trifluoroethyl), $C_1$-$C_6$-alkoxy-$C_1$-$C_4$-alkyl (e.g. 2-methoxyethyl), (halogenated $C_1$-$C_4$-alkyl)carbonyl (e.g. 2-fluoroacetyl, 2,2-difluoroacetyl, 2,2,2-trifluoroacetyl) or $C_1$-$C_4$-alkoxycarbonyl (e.g. ethoxycarbonyl).

Alternatively, $R^{4a}$, $R^{4b}$ together are optionally substituted $C_1$-$C_6$-alkylene (e.g. 1,4-butylene, 1,3-propylene, 2-fluorobut-1,4-ylene or 1-oxo-but-1,4-ylene), wherein one —$CH_2$— of $C_1$-$C_6$-alkylene may be replaced by an oxygen atom (e.g. —$CH_2$—$CH_2$—O—$CH_2$—$CH_2$—) or —$NR^{16}$.

In connection with $R^{4a}$ and $R^{4b}$, substituted $C_1$-$C_6$-alkylene in particular includes $C_1$-$C_6$-alkylene substituted with 1, 2 or 3 substituents selected from the group consisting of halogen (e.g. fluoro, chloro), $C_1$-$C_4$-alkyl (e.g. methyl), cyano, hydroxy and $C_1$-$C_4$-alkoxy.

$R^6$ is hydrogen or $C_1$-$C_6$-alkyl. Preferably, $R^6$ is hydrogen.
$R^7$ is hydrogen or $C_1$-$C_6$-alkyl. Preferably, $R^7$ is hydrogen.
$R^8$ is hydrogen or $C_1$-$C_6$-alkyl. Preferably, $R^8$ is hydrogen.
$R^9$ is hydrogen, $C_1$-$C_6$-alkyl (e.g. methyl or ethyl), $C_3$-$C_{12}$-cycloalkyl (e.g. cyclopropyl), amino-$C_1$-$C_6$-alkyl, optionally substituted $C_6$-$C_{12}$-aryl-$C_1$-$C_4$-alkyl or $C_3$-$C_{12}$-heterocyclyl (e.g. 3-azetidinyl). Preferably, $R^9$ is hydrogen or $C_1$-$C_6$-alkyl (e.g. methyl or ethyl).

According to a particular embodiment, $R^9$ and $R^1$ together are $C_1$-$C_4$-alkylene (e.g. 1,3-1,2-ethylene or propylene) so as that $R^9$ and $R^1$ together with the atom in Q to which $R^1$ is bound and the nitrogen atom to which $R^9$ is bound form an heterocyclic ring having, in particular, 4, 5 or 6 ring member atoms (including the nitrogen atom and Q). With W and $A^1$ both being a bond, such a ring may be represented by the following partial structure:

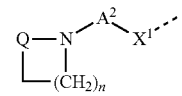

wherein $A^2$, $X^1$, Q are as defined herein (e.g. $S(O)_2$) and n is 0, 1, 2, 3 or 4.

According to a further particular embodiment, $R^9$ is $C_1$-$C_4$-alkylene (e.g. methylene or 1,3-propylene) that is bound to a carbon atom in $A^2$ and $A^2$ is $C_1$-$C_4$-alkylene so that $R^9$ and at least part of $A^2$ together with the nitrogen atom to which $R^9$ is bound form an N-containing heterocyclic ring having, in particular, 4, 5, 6 or 7 ring member atoms (including the nitrogen atom). Such a ring may be represented by the following partial structure:

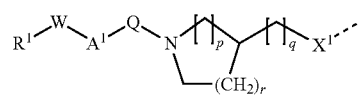

wherein $R^1$, W, $A^1$, Q and $X^1$ are as defined herein, p is 1 or 2, r is 0, 1 or 2 and q is 0, 1 or 2. In this particular embodiment, $X^1$ preferably is —O—. Particular combinations of p, r and q include p=1, r=0, q=1; and p=1, r=0, q=0. Alternatively, p is 0, r is 3 and q is 1, with $X^1$ preferably being —O—.

According to a further particular embodiment, $R^9$ is $C_1$-$C_4$-alkylene (e.g. methylene or 1,3-propylene) that is bound to a carbon atom in $X^1$ and $X^1$ is $C_1$-$C_4$-alkylene (e.g. 1,2-ethylene) so that $R^9$ and at least part of $X^1$ together with the nitrogen atom to which $R^9$ is bound form an N-containing heterocyclic ring having, in particular, 4, 5, 6 or 7 ring member atoms (including the nitrogen atom). With $A^2$ being a bond, such a ring may be represented by the following partial structure:

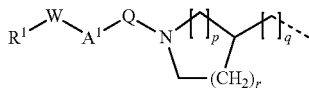

wherein $R^1$, W, $A^1$ and Q are as defined herein, p is 1 or 2, r is 0, 1 or 2 and q is 0, 1 or 2. Particular combinations of p, r and q include p=1, r=0, q=0.

$R^{10}$ is hydrogen, $C_1$-$C_6$-alkyl or $C_1$-$C_6$-alkylsulfonyl. Preferably, $R^{10}$ is hydrogen.

$R^{11}$ is hydrogen or $C_1$-$C_6$-alkyl. Preferably, $R^{11}$ is hydrogen.

Alternatively, $R^9$, $R^{11}$ together are $C_1$-$C_4$-alkylene (e.g. ethylene).

$R^{16}$ is hydrogen or $C_1$-$C_6$-alkyl. Preferably, $R^{16}$ is hydrogen.

$R^{17}$ is hydrogen or $C_1$-$C_6$-alkyl. Preferably, $R^{14}$ is hydrogen.

$R^{18}$ is hydrogen or $C_1$-$C_6$-alkyl. Preferably, $R^{15}$ is hydrogen.

Particular embodiments of phenalkylamine derivatives of the invention result if
R is $R^1$—W-$A^1$-Q-Y-$A^2$-$X^1$—;
$R^1$ is $C_1$-$C_6$-alkyl (e.g. n-propyl), $C_3$-$C_{12}$-cycloalkyl-$C_1$-$C_4$-alkyl (e.g. cyclopropylmethyl), halogenated $C_1$-$C_6$-alkyl (e.g. 3-fluoroprop-1-yl), or optionally substituted $C_3$-$C_{12}$-heterocyclyl (e.g. 1-methyl-1,2-diazol-4-yl or 1-methyl-1, 3-diazol-4-yl);
W is a bond;
$A^1$ is a bond;
Q is —S(O)$_2$—;
Y is —NR$^9$—;
$A^2$ is $C_1$-$C_4$-alkylene (e.g. 1,2-ethylene) or a bond;
$X^1$ is —O— or optionally substituted $C_1$-$C_4$-alkylene (e.g. methylene);
$R^2$ is hydrogen or halogen (e.g. fluorine);
$R^3$ is hydrogen;
$X^2$ is >CR$^{12a}$R$^{12b}$;
$X^3$ is a bond;
$R^5$ is optionally substituted phenyl (e.g. phenyl, 3-chlorophenyl, 3-trifluoromethylphenyl, 4-chlorophenyl, 3,5-difluorophenyl);
$Y^1$ is a bond;
$Y^2$ is >CR$^{15a}$R$^{15b}$ or a bond;
$R^{4a}$ is hydrogen, $C_1$-$C_6$-alkyl (e.g. methyl), $C_6$-$C_{12}$-aryl-$C_1$-$C_4$-alkyl (e.g. benzyl), or $C_1$-$C_4$-alkoxycarbonyl (e.g. tert-butyloxycarbonyl); or
$R^{4a}$, $R^3$
together are optionally substituted $C_1$-$C_6$-alkylene (e.g. methylene, 1,2-ethylene, 1,3-propylene, 1-oxo-1,2-ethylene, 1-oxo-1,3-propylene),
$R^{4b}$ is hydrogen, $C_1$-$C_6$-alkyl (e.g. methyl, ethyl, 2-propyl, 2,2,2-trimethylethyl), halogenated $C_1$-$C_4$-alkyl (e.g. 2-fluoroethyl, 2,2-difluoroethyl, 2,2,2-trifluoroethyl), $C_1$-$C_6$-alkoxy-$C_1$-$C_4$-alkyl (e.g. 2-methoxyethyl), (halogenated $C_1$-$C_4$-alkyl)carbonyl (e.g. 2-fluoroacetyl, 2,2-difluoroacetyl, 2,2,2-trifluoroacetyl) or $C_1$-$C_4$-alkoxycarbonyl (e.g. ethoxycarbonyl); or
$R^{4a}$, $R^{4b}$
together are $C_1$-$C_6$-alkylene (e.g. 1,3-propylene or 1,4-butylene), wherein one —CH$_2$— of $C_1$-$C_4$-alkylene may be replaced by an oxygen atom (e.g. —CH$_2$—CH$_2$—O—CH$_2$—CH$_2$—);
$R^9$ is hydrogen, $C_1$-$C_6$-alkyl (e.g. methyl), or
$R^{12a}$ is hydrogen;
$R^{12b}$ is hydrogen; or
$R^{12a}$, $R^{12b}$
together are optionally substituted $C_1$-$C_4$-alkylene (e.g. 1,3-propylene);
$R^{15a}$ is hydrogen; and
$R^{15b}$ is hydrogen; or
$R^{15a}$, $R^{15b}$
together are carbonyl.

Further particular embodiments of phenalkylamine derivatives of the invention result if
R is $R^1$—W-$A^1$-Q-Y-$A^2$-$X^1$—;
$R^1$ is $C_1$-$C_6$-alkyl (e.g. n-propyl), $C_3$-$C_{12}$-cycloalkyl-$C_1$-$C_4$-alkyl (e.g. cyclopropylmethyl), halogenated $C_1$-$C_6$-alkyl (e.g. 3-fluoroprop-1-yl), or optionally substituted $C_3$-$C_{12}$-heterocyclyl (e.g. 1-methyl-1,2-diazol-4-yl or 1-methyl-1, 3-diazol-4-yl);
W is a bond;
$A^1$ is a bond;
Q is —S(O)$_2$—;
Y is —NR$^9$—;
$A^2$ is $C_1$-$C_4$-alkylene (e.g. 1,2-ethylene) or a bond;
$X^1$ is —O— or optionally substituted $C_1$-$C_4$-alkylene (e.g. methylene);
$R^2$ is hydrogen or halogen (e.g. fluorine);
$R^3$ is hydrogen;
$X^2$ is >CR$^{12a}$R$^{12b}$;
$X^3$ is a bond;
$R^5$ is optionally substituted phenyl (e.g. phenyl, 3-chlorophenyl, 3-trifluoromethylphenyl, 4-chlorophenyl, 3,5-difluorophenyl);
$Y^1$ is a bond;
$Y^2$ is >CR$^{15a}$R$^{15b}$ or a bond;
$R^{4a}$ is hydrogen, $C_1$-$C_6$-alkyl (e.g. methyl), $C_6$-$C_{12}$-aryl-$C_1$-$C_4$-alkyl (e.g. benzyl), or $C_1$-$C_4$-alkoxycarbonyl (e.g. tert-butyloxycarbonyl);
$R^{4b}$ is hydrogen or $C_1$-$C_6$-alkyl (e.g. methyl); or
$R^{4a}$, $R^{4b}$
together are $C_1$-$C_6$-alkylene (e.g. 1,3-propylene or 1,4-butylene), wherein one —CH$_2$— of $C_1$-$C_4$-alkylene may be replaced by an oxygen atom (e.g. —CH$_2$—CH$_2$—O—CH$_2$—CH$_2$—);
$R^9$ is hydrogen, $C_1$-$C_6$-alkyl (e.g. methyl), or
$R^{12a}$ is hydrogen;
$R^{12b}$ is hydrogen; or
$R^{12a}$, $R^{12b}$
together are optionally substituted $C_1$-$C_4$-alkylene (e.g. 1,3-propylene);
$R^{15a}$ is hydrogen; and
$R^{15b}$ is hydrogen; or
$R^{15a}$, $R^{15b}$
together are carbonyl.

Further particular compounds of the present invention are the individual phenalkylamine derivatives of the formula (Id) as listed in the following tables 1 to 24 and physiologically tolerated salts thereof:

$$R^1\text{—}S(O)_2\text{—}Y\text{—}A^2\text{—}X^1 \quad \text{(Id)}$$

Table 1

Compounds of the formula (Id) wherein —$Y^1$—$Y^2$— is as defined herein and in particular represents a —$CH_2$—, —C(O)— or a bond, $R^2$ is hydrogen, $R^3$ is as defined herein and in particular represents hydrogen, $R^{20}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 2

Compounds of the formula (Id) wherein —$Y^1$—$Y^2$— is as defined herein and in particular represents —$CH_2$—, —C(O)— or a bond, $R^2$ is hydrogen, $R^3$ is as defined herein and in particular represents hydrogen, $R^{20}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 3

Compounds of the formula (Id) wherein —$Y^1$—$Y^2$— is as defined herein and in particular represents —$CH_2$—, —C(O)— or a bond, $R^2$ is hydrogen, $R^3$ is as defined herein and in particular represents hydrogen, $R^{20}$ is 3-Cl and the combination of $R^1$, >$CR^{12a}R^{12b}$, $R^{4a}$, $R^{4b}$ for a compound in each case corresponds to one line of Table A (A-1 to A-480).

Table 4

Compounds of the formula (Id) wherein —$Y^1$—$Y^2$— is as defined herein and in particular represents —$CH_2$—, —C(O)— or a bond, $R^2$ is hydrogen, $R^3$ is as defined herein and in particular represents hydrogen, $R^{20}$ is 3-$CF_3$ and the combination of $R^1$, >$CR^{12a}R^{12b}$, $R^{4a}$, $R^{4b}$ for a compound in each case corresponds to one line of Table A (A-1 to A-480).

Table 5

Compounds of the formula (Id) wherein —$Y^1$—$Y^2$— is as defined herein and in particular represents —$CH_2$—, —C(O)— or a bond, $R^2$ is hydrogen, $R^3$ is as defined herein and in particular represents hydrogen, $R^{20}$ is 2-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 6

Compounds of the formula (Id) wherein —$Y^1$—$Y^2$— is as defined herein and in particular represents —$CH_2$—, —C(O)— or a bond, $R^2$ is hydrogen, $R^3$ is as defined herein and in particular represents hydrogen, $R^{20}$ is 2-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 7

Compounds of the formula (Id) wherein —$Y^1$—$Y^2$— is as defined herein and in particular represents —$CH_2$—, —C(O)— or a bond, $R^2$ is 2-F, $R^3$ is as defined herein and in particular represents hydrogen, $R^{20}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 8

Compounds of the formula (Id) wherein —$Y^1$—$Y^2$— is as defined herein and in particular represents —$CH_2$—, —C(O)— or a bond, $R^2$ is 2-F, $R^3$ is as defined herein and in particular represents hydrogen, $R^{20}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 9

Compounds of the formula (Id) wherein —$Y^1$—$Y^2$— is as defined herein and in particular represents —$CH_2$—, —C(O)— or a bond, $R^2$ is 2-F, $R^3$ is as defined herein and in particular represents hydrogen, $R^{20}$ is 3-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 10

Compounds of the formula (Id) wherein —$Y^1$—$Y^2$— is as defined herein and in particular represents —$CH_2$—, —C(O)— or a bond, $R^2$ is 2-F, $R^3$ is as defined herein and in particular represents hydrogen, $R^{20}$ is 3-$CF_3$ and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 11

Compounds of the formula (Id) wherein —$Y^1$—$Y^2$— is as defined herein and in particular represents —$CH_2$—, —C(O)— or a bond, $R^2$ is 2-F, $R^3$ is as defined herein and in particular represents hydrogen, $R^{20}$ is 2-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 12

Compounds of the formula (Id) wherein —$Y^1$—$Y^2$— is as defined herein and in particular represents —$CH_2$—, —C(O)— or a bond, $R^2$ is 2-F, $R^3$ is as defined herein and in particular represents hydrogen, $R^{20}$ is 2-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 13

Compounds of the formula (Id) wherein —$Y^1$—$Y^2$— is as defined herein and in particular represents —$CH_2$—, —C(O)— or a bond, $R^2$ is 4-F, $R^3$ is as defined herein and in particular represents hydrogen, $R^{20}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 14

Compounds of the formula (Id) wherein —$Y^1$—$Y^2$— is as defined herein and in particular represents —$CH_2$—, —C(O)— or a bond, $R^2$ is 4-F, $R^3$ is as defined herein and in particular represents hydrogen, $R^{20}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 15

Compounds of the formula (Id) wherein —$Y^1$—$Y^2$— is as defined herein and in particular represents —$CH_2$—, —C(O)— or a bond, $R^2$ is 4-F, $R^3$ is as defined herein and in particular represents hydrogen, $R^{20}$ is 3-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 16

Compounds of the formula (Id) wherein —$Y^1$—$Y^2$— is as defined herein and in particular represents —$CH_2$—, —C(O)— or a bond, $R^2$ is 4-F, $R^3$ is as defined herein and in particular represents hydrogen, $R^{20}$ is 3-CF$_3$ and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 17

Compounds of the formula (Id) wherein —$Y^1$—$Y^2$— is as defined herein and in particular represents —CH$_2$—, —C(O)— or a bond, $R^2$ is 4-F, $R^3$ is as defined herein and in particular represents hydrogen, $R^{20}$ is 2-F and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 18

Compounds of the formula (Id) wherein —$Y^1$—$Y^2$— is as defined herein and in particular represents —CH$_2$—, —C(O)— or a bond, $R^2$ is 4-F, $R^3$ is as defined herein and in particular represents hydrogen, $R^{20}$ is 2-Cl and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 19

Compounds of the formula (Id) wherein —$Y^1$—$Y^2$— is as defined herein and in particular represents —CH$_2$—, —C(O)— or a bond, $R^2$ is 4-Cl, $R^3$ is as defined herein and in particular represents hydrogen, $R^{20}$ is hydrogen and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 20

Compounds of the formula (Id) wherein —$Y^1$—$Y^2$— is as defined herein and in particular represents —CH$_2$—, —C(O)— or a bond, $R^2$ is 4-Cl, $R^3$ is as defined herein and in particular represents hydrogen, $R^{20}$ is 3-F and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 21

Compounds of the formula (Id) wherein —$Y^1$—$Y^2$— is as defined herein and in particular represents —CH$_2$—, —C(O)— or a bond, $R^2$ is 4-Cl, $R^3$ is as defined herein and in particular represents hydrogen, $R^{20}$ is 3-Cl and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 22

Compounds of the formula (Id) wherein —$Y^1$—$Y^2$— is as defined herein and in particular represents —CH$_2$—, —C(O)— or a bond, $R^2$ is 4-Cl, $R^3$ is as defined herein and in particular represents hydrogen, $R^{20}$ is 3-CF$_3$ and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 23

Compounds of the formula (Id) wherein —$Y^1$—$Y^2$— is as defined herein and in particular represents —CH$_2$—, —C(O)— or a bond, $R^2$ is 4-Cl, $R^3$ is as defined herein and in particular represents hydrogen, $R^{20}$ is 2-F and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

Table 24

Compounds of the formula (Id) wherein —$Y^1$—$Y^2$— is as defined herein and in particular represents —CH$_2$—, —C(O)— or a bond, $R^2$ is 4-Cl, $R^3$ is as defined herein and in particular represents hydrogen, $R^{20}$ is 2-Cl and the combination of $R^1$, —Y-$A^2$-$X^1$—, >CR$^{12a}$R$^{12b}$, $R^{4a}$, $R^{4b}$ for a compound in each case corresponds to one line of Table A (A-1 to A-480).

|  | $R^1$ | —Y—$A^2$—$X^1$— | >CR$^{12a}$R$^{12b}$ | $R^{4a}$, $R^{4b}$ |
|---|---|---|---|---|
| A-1. | 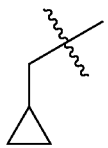 [SMILES: *CC1CC1] | —NH—(CH$_2$)$_2$—O— | —CH$_2$— | —CH$_3$, H |
| A-2. | 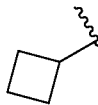 | —NH—(CH$_2$)$_2$—O— | —CH$_2$— | —CH$_3$, H |
| A-3. | 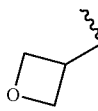 | —NH—(CH$_2$)$_2$—O— | —CH$_2$— | —CH$_3$, H |
| A-4. |  | —NH—(CH$_2$)$_2$—O— | —CH$_2$— | —CH$_3$, H |
| A-5. | 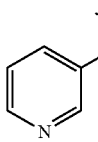 | —NH—(CH$_2$)$_2$—O— | —CH$_2$— | —CH$_3$, H |

-continued
| | R¹ | —Y—A²—X¹— | >CR¹²ᵃR¹²ᵇ | R⁴ᵃ, R⁴ᵇ |
|---|---|---|---|---|
| A-6. | 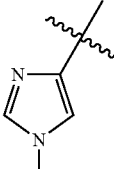 | —NH—(CH₂)₂—O— | —CH₂— | —CH₃, H |
| A-7. | 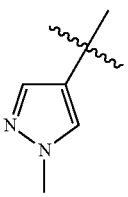 | —NH—(CH₂)₂—O— | —CH₂— | —CH₃, H |
| A-8. | 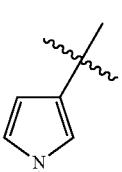 | —NH—(CH₂)₂—O— | —CH₂— | —CH₃, H |
| A-9. | 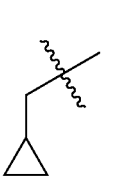 [SMILES: *CC1CC1] | —NH—(CH₂)₂— | —CH₂— | —CH₃, H |
| A-10. |  | —NH—(CH₂)₂— | —CH₂— | —CH₃, H |
| A-11. | 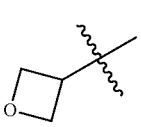 [SMILES: *C1COC1] | —NH—(CH₂)₂— | —CH₂— | —CH₃, H |
| A-12. | 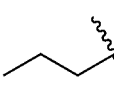 | —NH—(CH₂)₂— | —CH₂— | —CH₃, H |
| A-13. | 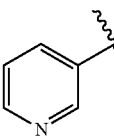 | —NH—(CH₂)₂— | —CH₂— | —CH₃, H |
| A-14. | 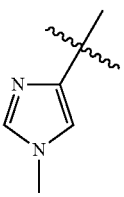 [SMILES: *c1cn(C)cn1] | —NH—(CH₂)₂— | —CH₂— | —CH₃, H |

-continued
| | R¹ | —Y—A²—X¹— | >CR¹²ᵃR¹²ᵇ | R⁴ᵃ, R⁴ᵇ |
|---|---|---|---|---|
| A-15. | 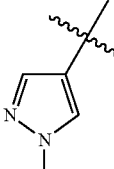 | —NH—(CH₂)₂— | —CH₂— | —CH₃, H |
| A-16. | 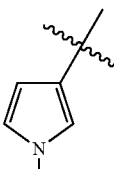 | —NH—(CH₂)₂— | —CH₂— | —CH₃, H |
| A-17. | 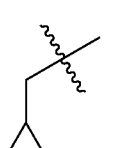 | —NH—CH₂— | —CH₂— | —CH₃, H |
| A-18. | 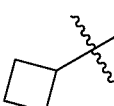 | —NH—CH₂— | —CH₂— | —CH₃, H |
| A-19. | 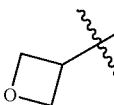 | —NH—CH₂— | —CH₂— | —CH₃, H |
| A-20. | 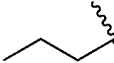 | —NH—CH₂— | —CH₂— | —CH₃, H |
| A-21. | 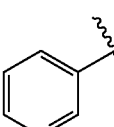 | —NH—CH₂— | —CH₂— | —CH₃, H |
| A-22. | 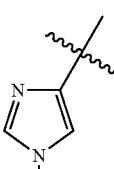 | —NH—CH₂— | —CH₂— | —CH₃, H |
| A-23. | 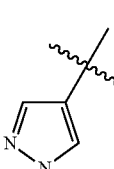 | —NH—CH₂— | —CH₂— | —CH₃, H |

| | R¹ | —Y—A²—X¹— | >CR¹²ᵃR¹²ᵇ | R⁴ᵃ, R⁴ᵇ |
|---|---|---|---|---|
| A-24. | 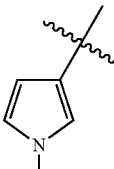 | —NH—CH₂— | —CH₂— | —CH₃, H |
| A-25. | 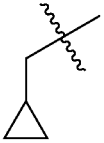 | 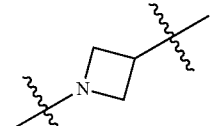 | —CH₂— | —CH₃, H |
| A-26. | 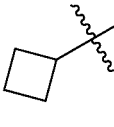 | 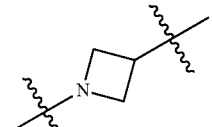 | —CH₂— | —CH₃, H |
| A-27. | 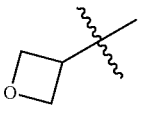 [SMILES: *C1COC1] | 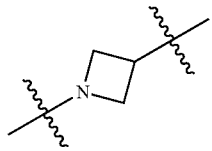 [SMILES: *C1CN(*)C1] | —CH₂— | —CH₃, H |
| A-28. | 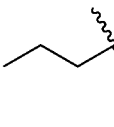 | 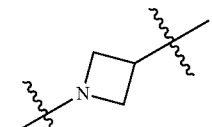 | —CH₂— | —CH₃, H |
| A-29. | 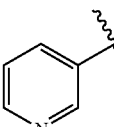 | 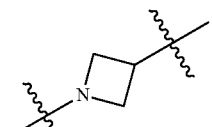 | —CH₂— | —CH₃, H |
| A-30. | 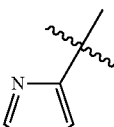 | 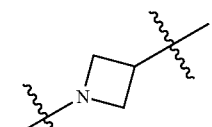 | —CH₂— | —CH₃, H |
| A-31. |  |  | —CH₂— | —CH₃, H |

-continued

| | R¹ | —Y—A²—X¹— | >CR$^{12a}$R$^{12b}$ | R$^{4a}$, R$^{4b}$ |
|---|---|---|---|---|
| A-32. | (1-methyl-pyrrol-3-yl) | (azetidin-3-yl, N-linked) | —CH$_2$— | —CH$_3$, H |
| A-33. | (cyclopropylmethyl) | —(CH$_2$)$_2$— | —CH$_2$— | —CH$_3$, H |
| A-34. | (cyclobutyl) | —(CH$_2$)$_2$— | —CH$_2$— | —CH$_3$, H |
| A-35. | (oxetan-3-yl) | —(CH$_2$)$_2$— | —CH$_2$— | —CH$_3$, H |
| A-36. | (sec-butyl) | —(CH$_2$)$_2$— | —CH$_2$— | —CH$_3$, H |
| A-37. | (pyridin-3-yl) | —(CH$_2$)$_2$— | —CH$_2$— | —CH$_3$, H |
| A-38. | (1-methyl-imidazol-4-yl) | —(CH$_2$)$_2$— | —CH$_2$— | —CH$_3$, H |
| A-39. | (1-methyl-pyrazol-4-yl) | —(CH$_2$)$_2$— | —CH$_2$— | —CH$_3$, H |
| A-40. | (1-methyl-pyrrol-3-yl) | —(CH$_2$)$_2$— | —CH$_2$— | —CH$_3$, H |

-continued
| | R¹ | —Y—A²—X¹— | >CR¹²ᵃR¹²ᵇ | R⁴ᵃ, R⁴ᵇ |
|---|---|---|---|---|
| A-41. | 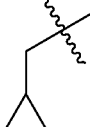 | —NH—(CH₂)₂—O— | 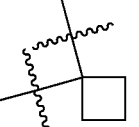 | —CH₃, H |
| A-42. |  | —NH—(CH₂)₂—O— | 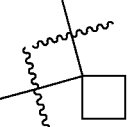 | —CH₃, H |
| A-43. | 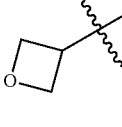 | —NH—(CH₂)₂—O— | 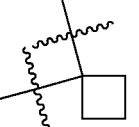 | —CH₃, H |
| A-44. | 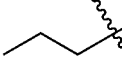 | —NH—(CH₂)₂—O— | 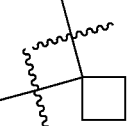 | —CH₃, H |
| A-45. | 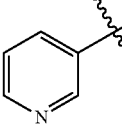 | —NH—(CH₂)₂—O— | 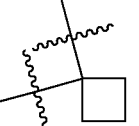 | —CH₃, H |
| A-46. | 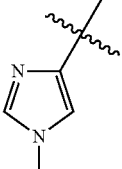 | —NH—(CH₂)₂—O— | 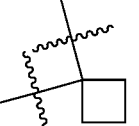 | —CH₃, H |
| A-47. | 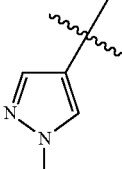 | —NH—(CH₂)₂—O— | 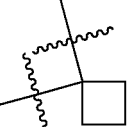 | —CH₃, H |
| A-48. | 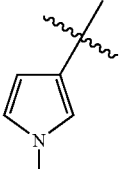 | —NH—(CH₂)₂—O— | 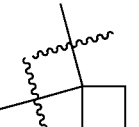 | —CH₃, H |
| A-49. | 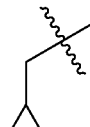 | —NH—(CH₂)₂— | 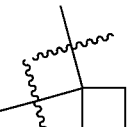 | —CH₃, H |

-continued

| | R¹ | —Y—A²—X¹— | >CR^{12a}R^{12b} | R^{4a}, R^{4b} |
|---|---|---|---|---|
| A-50. | cyclobutyl | —NH—(CH$_2$)$_2$— | | —CH$_3$, H |
| A-51. | oxetanyl | —NH—(CH$_2$)$_2$— | | —CH$_3$, H |
| A-52. | n-butyl | —NH—(CH$_2$)$_2$— | | —CH$_3$, H |
| A-53. | pyridin-3-yl | —NH—(CH$_2$)$_2$— | | —CH$_3$, H |
| A-54. | 1-methyl-1H-imidazol-4-yl | —NH—(CH$_2$)$_2$— | | —CH$_3$, H |
| A-55. | 1-methyl-1H-pyrazol-4-yl | —NH—(CH$_2$)$_2$— | | —CH$_3$, H |
| A-56. | 1H-pyrrol-3-yl | —NH—(CH$_2$)$_2$— | | —CH$_3$, H |
| A-57. | cyclopropylmethyl | —NH—CH$_2$— | | —CH$_3$, H |
| A-58. | cyclobutyl | —NH—CH$_2$— | | —CH$_3$, H |

-continued

| | R¹ | —Y—A²—X¹— | >CR¹²ᵃR¹²ᵇ | R⁴ᵃ, R⁴ᵇ |
|---|---|---|---|---|
| A-59. | (oxetan-3-yl) | —NH—CH₂— | (cyclobutyl) | —CH₃, H |
| A-60. | (butan-2-yl) | —NH—CH₂— | (cyclobutyl) | —CH₃, H |
| A-61. | (pyridin-3-yl) | —NH—CH₂— | (cyclobutyl) | —CH₃, H |
| A-62. | (1-methyl-1H-imidazol-4-yl) | —NH—CH₂— | (cyclobutyl) | —CH₃, H |
| A-63. | (1-methyl-1H-pyrazol-4-yl) | —NH—CH₂— | (cyclobutyl) | —CH₃, H |
| A-64. | (1-methyl-1H-pyrrol-3-yl) | —NH—CH₂— | (cyclobutyl) | —CH₃, H |
| A-65. | (cyclopropylmethyl) | (azetidin-3-yl) | (cyclobutyl) | —CH₃, H |
| A-66. | (cyclobutyl) | (azetidin-3-yl) | (cyclobutyl) | —CH₃, H |
| A-67. | (oxetan-3-yl) | (azetidin-3-yl) | (cyclobutyl) | —CH₃, H |

-continued

| | R¹ | —Y—A²—X¹— | >CR¹²ᵃR¹²ᵇ | R⁴ᵃ, R⁴ᵇ |
|---|---|---|---|---|
| A-68. | (n-butyl) | azetidine (N,3-linked) | cyclobutyl | —CH₃, H |
| A-69. | pyridin-3-yl | azetidine (N,3-linked) | cyclobutyl | —CH₃, H |
| A-70. | 1-methylimidazol-4-yl | azetidine (N,3-linked) | cyclobutyl | —CH₃, H |
| A-71. | 1-methylpyrazol-4-yl | azetidine (N,3-linked) | cyclobutyl | —CH₃, H |
| A-72. | 1-methylpyrrol-3-yl | azetidine (N,3-linked) | cyclobutyl | —CH₃, H |
| A-73. | cyclopropylmethyl | —(CH₂)₂— | cyclobutyl | —CH₃, H |
| A-74. | cyclobutyl | —(CH₂)₂— | cyclobutyl | —CH₃, H |
| A-75. | oxetan-3-yl | —(CH₂)₂— | cyclobutyl | —CH₃, H |
| A-76. | (n-propyl) | —(CH₂)₂— | cyclobutyl | —CH₃, H |

-continued
| | R¹ | —Y—A²—X¹— | >CR¹²ᵃR¹²ᵇ | R⁴ᵃ, R⁴ᵇ |
|---|---|---|---|---|
| A-77. | 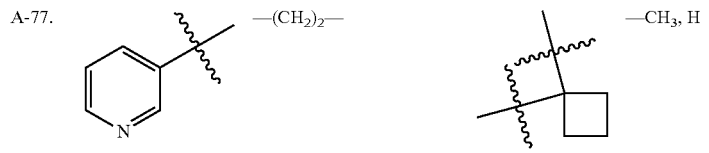 | —(CH₂)₂— | | —CH₃, H |
| A-78. | 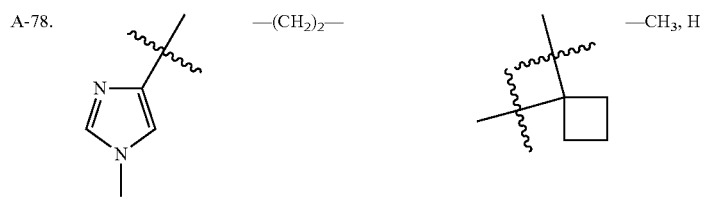 | —(CH₂)₂— | | —CH₃, H |
| A-79. | 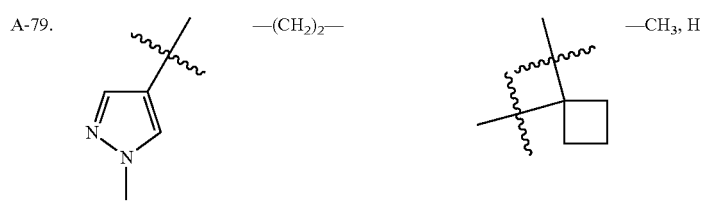 | —(CH₂)₂— | | —CH₃, H |
| A-80. | 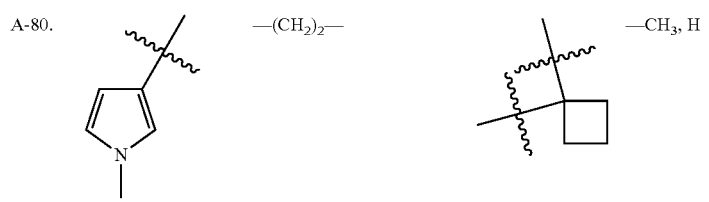 | —(CH₂)₂— | | —CH₃, H |
| A-81. | 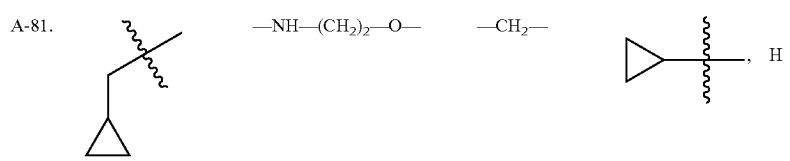 | —NH—(CH₂)₂—O— | —CH₂— | , H |
| A-82. | 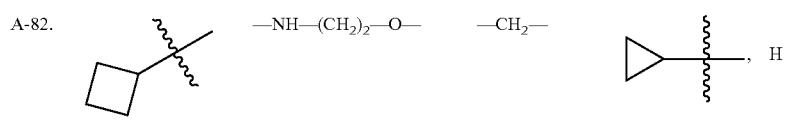 | —NH—(CH₂)₂—O— | —CH₂— | , H |
| A-83. | 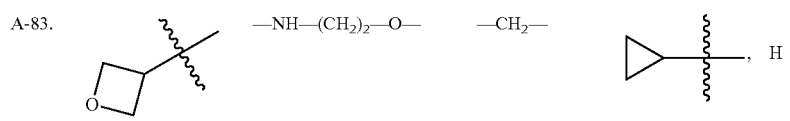 | —NH—(CH₂)₂—O— | —CH₂— | , H |
| A-84. | 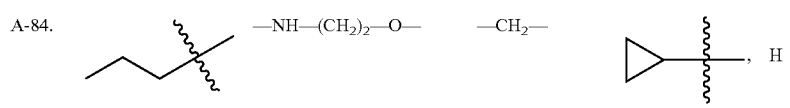 | —NH—(CH₂)₂—O— | —CH₂— | , H |
| A-85. | 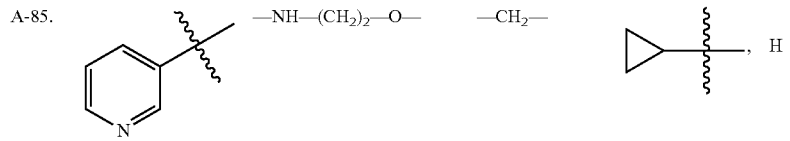 | —NH—(CH₂)₂—O— | —CH₂— | , H |

| | R¹ | —Y—A²—X¹— | >CR¹²ᵃR¹²ᵇ | R⁴ᵃ, R⁴ᵇ |
|---|---|---|---|---|
| A-86. | 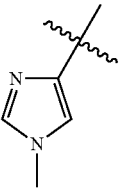 [SMILES: *c1cn(C)cn1] | —NH—(CH₂)₂—O— | —CH₂— | 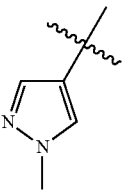, H |
| A-87. | 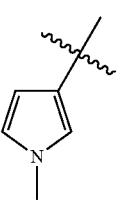 [SMILES: *c1ccn(C)c1] | —NH—(CH₂)₂—O— | —CH₂— | 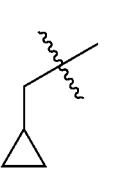, H |
| A-88. | 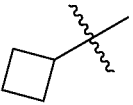 [SMILES: *C1CCC1] | —NH—(CH₂)₂—O— | —CH₂— | , H |
| A-89. | 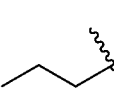 | —NH—(CH₂)₂— | —CH₂— | 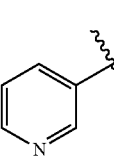, H |
| A-90. | 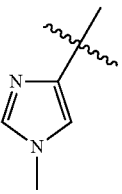 [SMILES: *c1cn(C)cn1] | —NH—(CH₂)₂— | —CH₂— | , H |
| A-91. | | —NH—(CH₂)₂— | —CH₂— | , H |
| A-92. | | —NH—(CH₂)₂— | —CH₂— | , H |
| A-93. | | —NH—(CH₂)₂— | —CH₂— | , H |
| A-94. | | —NH—(CH₂)₂— | —CH₂— | , H |

-continued

| | R¹ | —Y—A²—X¹— | >CR¹²ᵃR¹²ᵇ | R⁴ᵃ, R⁴ᵇ |
|---|---|---|---|---|
| A-95. | 1-methyl-1H-pyrazol-4-yl | —NH—(CH₂)₂— | —CH₂— | cyclopropyl, H |
| A-96. | 1-methyl-1H-pyrrol-3-yl | —NH—(CH₂)₂— | —CH₂— | cyclopropyl, H |
| A-97. | cyclopropylmethyl | —NH—CH₂— | —CH₂— | cyclopropyl, H |
| A-98. | cyclobutyl | —NH—CH₂— | —CH₂— | cyclopropyl, H |
| A-99. | oxetan-3-yl | —NH—CH₂— | —CH₂— | cyclopropyl, H |
| A-100. | sec-butyl | —NH—CH₂— | —CH₂— | cyclopropyl, H |
| A-101. | pyridin-3-yl | —NH—CH₂— | —CH₂— | cyclopropyl, H |
| A-102. | 1-methyl-1H-imidazol-5-yl | —NH—CH₂— | —CH₂— | cyclopropyl, H |
| A-103. | 1-methyl-1H-pyrazol-4-yl | —NH—CH₂— | —CH₂— | cyclopropyl, H |

-continued

| | R¹ | —Y—A²—X¹— | >CR¹²ᵃR¹²ᵇ | R⁴ᵃ, R⁴ᵇ |
|---|---|---|---|---|
| A-104. | 1-methylpyrrol-3-yl | —NH—CH₂— | —CH₂— | cyclopropyl, H |
| A-105. | cyclopropylmethyl | azetidin-3-yl (N-linked) | —CH₂— | cyclopropyl, H |
| A-106. | cyclobutyl | azetidin-3-yl (N-linked) | —CH₂— | cyclopropyl, H |
| A-107. | oxetan-3-yl | azetidin-3-yl (N-linked) | —CH₂— | cyclopropyl, H |
| A-108. | n-propyl | azetidin-3-yl (N-linked) | —CH₂— | cyclopropyl, H |
| A-109. | pyridin-3-yl | azetidin-3-yl (N-linked) | —CH₂— | cyclopropyl, H |
| A-110. | 1-methylimidazol-5-yl | azetidin-3-yl (N-linked) | —CH₂— | cyclopropyl, H |
| A-111. | 1-methylpyrazol-4-yl | azetidin-3-yl (N-linked) | —CH₂— | cyclopropyl, H |

-continued

| | R¹ | —Y—A²—X¹— | >CR$^{12a}$R$^{12b}$ | R$^{4a}$, R$^{4b}$ |
|---|---|---|---|---|
| A-112. | *N-methylpyrrol-3-yl* | *azetidin-3-yl (N-linked)* | —CH$_2$— | cyclopropyl, H |
| A-113. | cyclopropylmethyl | —(CH$_2$)$_2$— | —CH$_2$— | cyclopropyl, H |
| A-114. | cyclobutyl | —(CH$_2$)$_2$— | —CH$_2$— | cyclopropyl, H |
| A-115. | oxetan-3-yl | —(CH$_2$)$_2$— | —CH$_2$— | cyclopropyl, H |
| A-116. | *sec-butyl* | —(CH$_2$)$_2$— | —CH$_2$— | cyclopropyl, H |
| A-117. | pyridin-3-yl | —(CH$_2$)$_2$— | —CH$_2$— | cyclopropyl, H |
| A-118. | 1-methylimidazol-4-yl | —(CH$_2$)$_2$— | —CH$_2$— | cyclopropyl, H |
| A-119. | 1-methylpyrazol-4-yl | —(CH$_2$)$_2$— | —CH$_2$— | cyclopropyl, H |
| A-120. | 1-methylpyrrol-3-yl | —(CH$_2$)$_2$— | —CH$_2$— | cyclopropyl, H |

-continued
| | R¹ | —Y—A²—X¹— | >CR^{12a}R^{12b} | R^{4a}, R^{4b} |
|---|---|---|---|---|
| A-121. |  | —NH—(CH₂)₂—O— |  | , H |
| A-122. |  | —NH—(CH₂)₂—O— |  | , H |
| A-123. |  | —NH—(CH₂)₂—O— |  | , H |
| A-124. |  | —NH—(CH₂)₂—O— |  | , H |
| A-125. |  | —NH—(CH₂)₂—O— |  | , H |
| A-126. |  | —NH—(CH₂)₂—O— |  | , H |
| A-127. | | —NH—(CH₂)₂—O— | | , H |
| A-128. | | —NH—(CH₂)₂—O— | | , H |
| A-129. | | —NH—(CH₂)₂— | | , H |

US 8,877,794 B2
-continued
| | R¹ | —Y—A²—X¹— | >CR¹²ᵃR¹²ᵇ | R⁴ᵃ, R⁴ᵇ |
|---|---|---|---|---|
| A-130. | 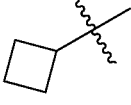 | —NH—(CH₂)₂— | 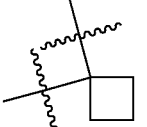 | 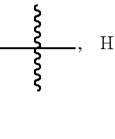, H |
| A-131. | 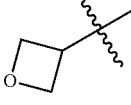 | —NH—(CH₂)₂— | 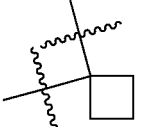 | 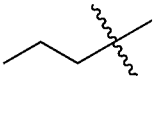 [SMILES: *CCC], H |
| A-132. | 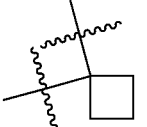 | —NH—(CH₂)₂— | 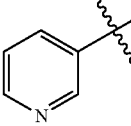 | 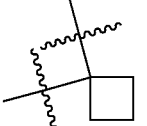, H |
| A-133. | 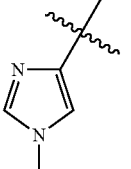 | —NH—(CH₂)₂— | 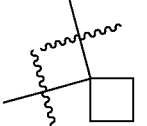 | 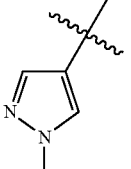, H |
| A-134. | 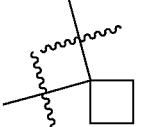 | —NH—(CH₂)₂— | 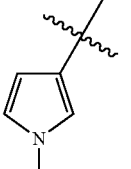 | 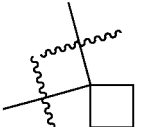, H |
| A-135. | 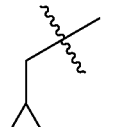 | —NH—(CH₂)₂— | 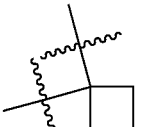 | 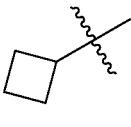, H |
| A-136. | 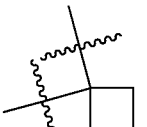 | —NH—(CH₂)₂— | | , H |
| A-137. | | —NH—CH₂— | | , H |
| A-138. | | —NH—CH₂— | | , H |

-continued
| | R¹ | —Y—A²—X¹— | >CR¹²ᵃR¹²ᵇ | R⁴ᵃ, R⁴ᵇ |
|---|---|---|---|---|
| A-139. | 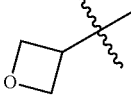 | —NH—CH₂— | 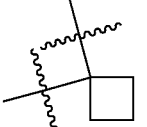 | 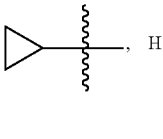, H |
| A-140. | 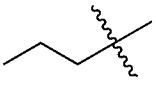 [SMILES: *CCC] | —NH—CH₂— | 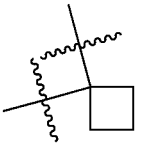 [SMILES: *C1(*)CCC1] | 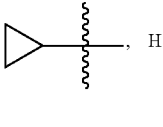, H |
| A-141. | 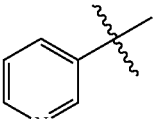 | —NH—CH₂— | 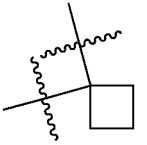 | 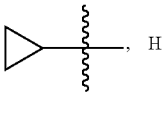, H |
| A-142. | 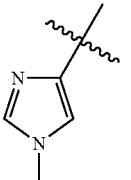 | —NH—CH₂— | 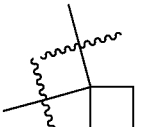 | 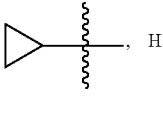, H |
| A-143. | 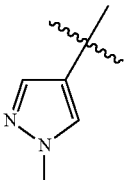 | —NH—CH₂— | 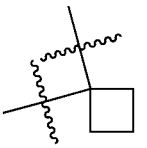 [SMILES: *C1(*)CCC1] | 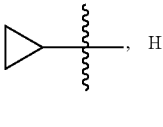, H |
| A-144. | 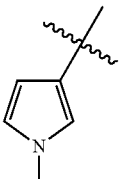 | —NH—CH₂— | 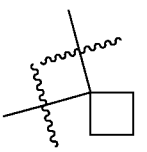 [SMILES: *C1(*)CCC1] | 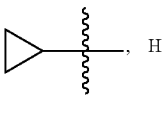, H |
| A-145. | 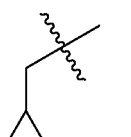 | 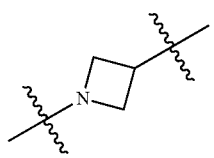 [SMILES: *C1CN(*)C1] | 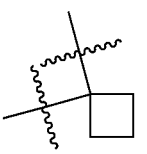 [SMILES: *C1(*)CCC1] | 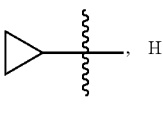, H |
| A-146. | 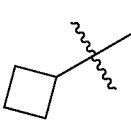 [SMILES: *C1CCC1] | 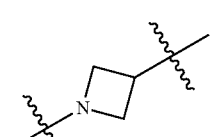 | 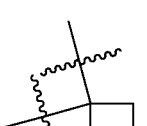 | 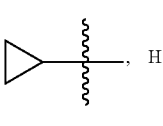, H |
| A-147. | 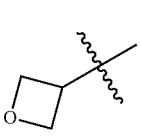 [SMILES: *C1COC1] | 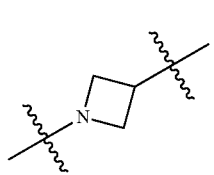 [SMILES: *C1CN(*)C1] | 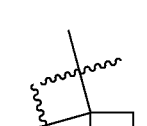 | 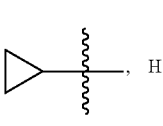, H |

-continued

| | R¹ | —Y—A²—X¹— | >CR$^{12a}$R$^{12b}$ | R$^{4a}$, R$^{4b}$ |
|---|---|---|---|---|
| A-148. | | | | , H |
| A-149. | | | | , H |
| A-150. | | | | , H |
| A-151. | | | | , H |
| A-152. | | | | , H |
| A-153. | | —(CH$_2$)$_2$— | | , H |
| A-154. | | —(CH$_2$)$_2$— | | , H |
| A-155. | | —(CH$_2$)$_2$— | | , H |
| A-156. | | —(CH$_2$)$_2$— | | , H |

-continued
| | R¹ | —Y—A²—X¹— | >CR^{12a}R^{12b} | R^{4a}, R^{4b} |
|---|---|---|---|---|
| A-157. | 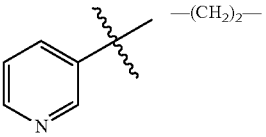 | —(CH₂)₂— | 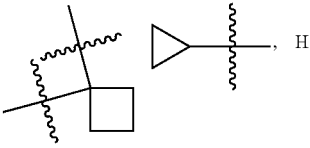 | 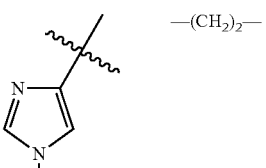, H |
| A-158. | 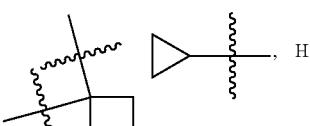 | —(CH₂)₂— | 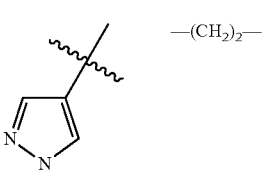 | 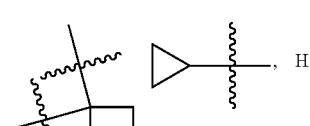, H |
| A-159. | 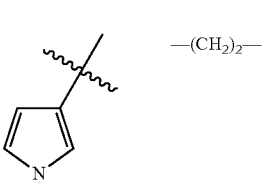 | —(CH₂)₂— | 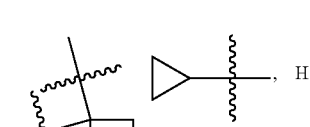 | 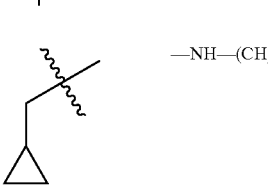, H |
| A-160. |  | —(CH₂)₂— | 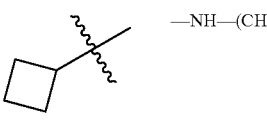 | 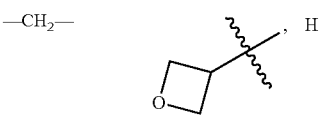, H |
| A-161. |  | —NH—(CH₂)₂—O— | —CH₂— | 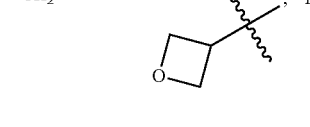, H |
| A-162. | 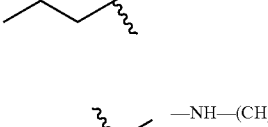 | —NH—(CH₂)₂—O— | —CH₂— | 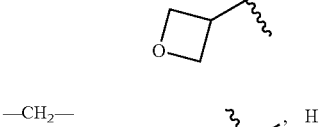, H |
| A-163. |  | —NH—(CH₂)₂—O— | —CH₂— | 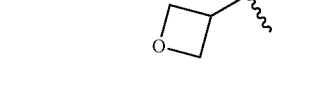, H |
| A-164. |  | —NH—(CH₂)₂—O— | —CH₂— | , H |
| A-165. |  | —NH—(CH₂)₂—O— | —CH₂— | , H |

| | R¹ | —Y—A²—X¹— | >CR¹²ᵃR¹²ᵇ | R⁴ᵃ, R⁴ᵇ |
|---|---|---|---|---|
| A-166. | 1-methylimidazol-4-yl | —NH—(CH₂)₂—O— | —CH₂— | oxetan-3-yl, H |
| A-167. | 1-methylpyrazol-4-yl | —NH—(CH₂)₂—O— | —CH₂— | oxetan-3-yl, H |
| A-168. | 1-methylpyrrol-3-yl | —NH—(CH₂)₂—O— | —CH₂— | oxetan-3-yl, H |
| A-169. | cyclopropylmethyl | —NH—(CH₂)₂— | —CH₂— | oxetan-3-yl, H |
| A-170. | cyclobutyl | —NH—(CH₂)₂— | —CH₂— | oxetan-3-yl, H |
| A-171. | oxetan-3-yl | —NH—(CH₂)₂— | —CH₂— | oxetan-3-yl, H |
| A-172. | n-propyl | —NH—(CH₂)₂— | —CH₂— | oxetan-3-yl, H |
| A-173. | pyridin-3-yl | —NH—(CH₂)₂— | —CH₂— | oxetan-3-yl, H |
| A-174. | 1-methylimidazol-5-yl | —NH—(CH₂)₂— | —CH₂— | oxetan-3-yl, H |

-continued

| | R¹ | —Y—A²—X¹— | >CR¹²ᵃR¹²ᵇ | R⁴ᵃ, R⁴ᵇ |
|---|---|---|---|---|
| A-175. | 1-methylpyrazol-4-yl | —NH—(CH₂)₂— | —CH₂— | oxetan-3-yl, H |
| A-176. | 1-methylpyrrol-3-yl | —NH—(CH₂)₂— | —CH₂— | oxetan-3-yl, H |
| A-177. | cyclopropylmethyl | —NH—CH₂— | —CH₂— | oxetan-3-yl, H |
| A-178. | cyclobutyl | —NH—CH₂— | —CH₂— | oxetan-3-yl, H |
| A-179. | oxetan-3-yl | —NH—CH₂— | —CH₂— | oxetan-3-yl, H |
| A-180. | sec-butyl | —NH—CH₂— | —CH₂— | oxetan-3-yl, H |
| A-181. | pyridin-3-yl | —NH—CH₂— | —CH₂— | oxetan-3-yl, H |
| A-182. | 1-methylimidazol-5-yl | —NH—CH₂— | —CH₂— | oxetan-3-yl, H |
| A-183. | 1-methylpyrazol-4-yl | —NH—CH₂— | —CH₂— | oxetan-3-yl, H |

-continued
| | R¹ | —Y—A²—X¹— | >CR^{12a}R^{12b} | R^{4a}, R^{4b} |
|---|---|---|---|---|
| A-184. | 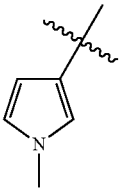 [SMILES: *c1ccn(C)c1] | —NH—CH₂— | —CH₂— | , H |
| A-185. | 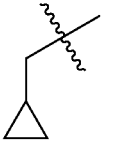 | 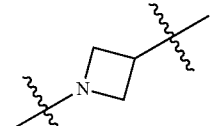 | —CH₂— | , H |
| A-186. | 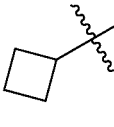 | 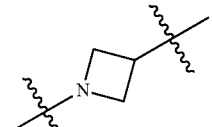 | —CH₂— | , H |
| A-187. | 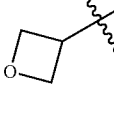 | 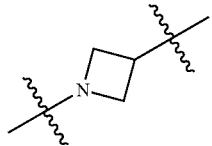 [SMILES: *C1CN(*)C1] | —CH₂— | 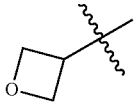, H |
| A-188. | 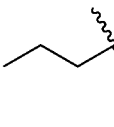 | 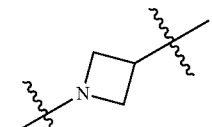 | —CH₂— | , H |
| A-189. | 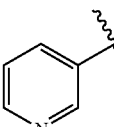 | 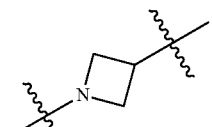 | —CH₂— | , H |
| A-190. | 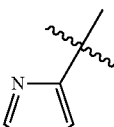 | 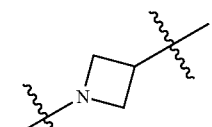 | —CH₂— | , H |
| A-191. | 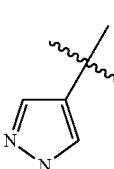 |  | —CH₂— | 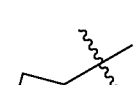, H |

-continued

| | R¹ | —Y—A²—X¹— | >CR¹²ᵃR¹²ᵇ | R⁴ᵃ, R⁴ᵇ |
|---|---|---|---|---|
| A-192. | 1-methylpyrrol-3-yl | azetidine-1,3-diyl | —CH₂— | oxetan-3-yl, H |
| A-193. | cyclopropylmethyl | —(CH₂)₂— | —CH₂— | oxetan-3-yl, H |
| A-194. | cyclobutyl | —(CH₂)₂— | —CH₂— | oxetan-3-yl, H |
| A-195. | oxetan-3-yl | —(CH₂)₂— | —CH₂— | oxetan-3-yl, H |
| A-196. | n-butyl | —(CH₂)₂— | —CH₂— | oxetan-3-yl, H |
| A-197. | pyridin-3-yl | —(CH₂)₂— | —CH₂— | oxetan-3-yl, H |
| A-198. | 1-methylimidazol-4-yl | —(CH₂)₂— | —CH₂— | oxetan-3-yl, H |
| A-199. | 1-methylpyrazol-4-yl | —(CH₂)₂— | —CH₂— | oxetan-3-yl, H |
| A-200. | 1-methylpyrrol-3-yl | —(CH₂)₂— | —CH₂— | oxetan-3-yl, H |

-continued
| | R¹ | —Y—A²—X¹— | >CR$^{12a}$R$^{12b}$ | R$^{4a}$, R$^{4b}$ |
|---|---|---|---|---|
| A-201. | 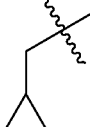 | —NH—(CH$_2$)$_2$—O— | 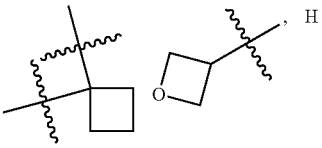 | , H |
| A-202. | 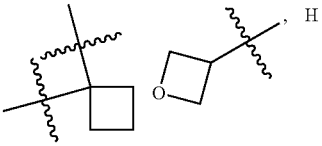 | —NH—(CH$_2$)$_2$—O— |  | 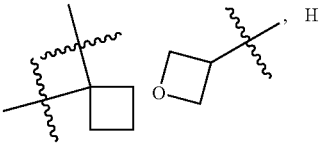, H |
| A-203. | 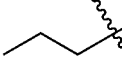 | —NH—(CH$_2$)$_2$—O— | 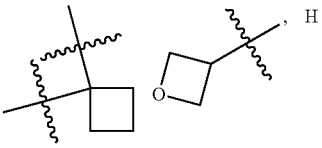 | 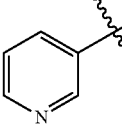, H |
| A-204. | 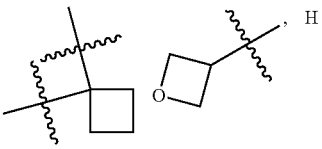 | —NH—(CH$_2$)$_2$—O— | 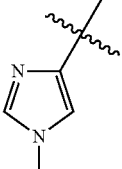 | 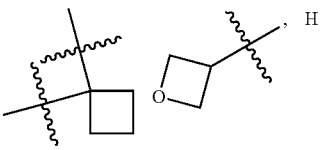, H |
| A-205. | 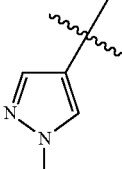 | —NH—(CH$_2$)$_2$—O— | 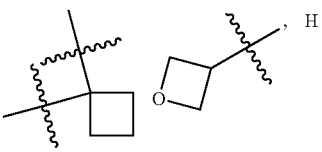 | 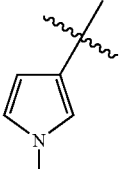, H |
| A-206. | 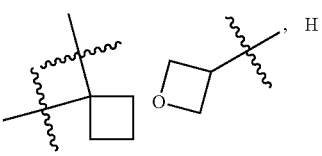 | —NH—(CH$_2$)$_2$—O— | | , H |
| A-207. | | —NH—(CH$_2$)$_2$—O— | | , H |
| A-208. | | —NH—(CH$_2$)$_2$—O— | | , H |
| A-209. | 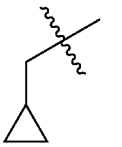 [SMILES: *CC1CC1] | —NH—(CH$_2$)$_2$— | 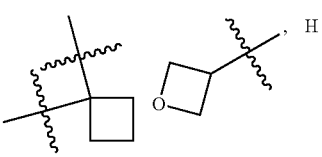 | , H |

|  | R¹ | —Y—A²—X¹— | >CR¹²ᵃR¹²ᵇ | R⁴ᵃ, R⁴ᵇ |
|---|---|---|---|---|
| A-210. | 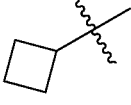 | —NH—(CH₂)₂— | 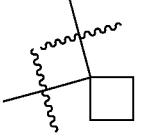 | 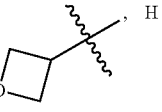, H |
| A-211. | 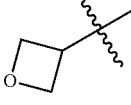 | —NH—(CH₂)₂— | 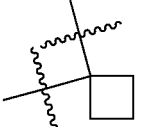 | 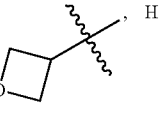, H |
| A-212. | 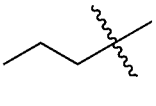 [SMILES: *CCC] | —NH—(CH₂)₂— | 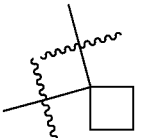 | 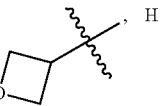, H |
| A-213. | 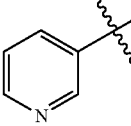 | —NH—(CH₂)₂— | 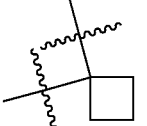 | 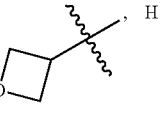, H |
| A-214. | 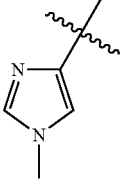 | —NH—(CH₂)₂— | 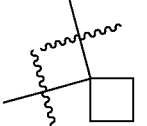 | 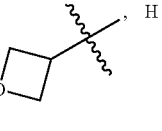, H |
| A-215. | 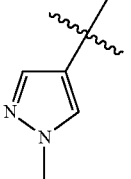 | —NH—(CH₂)₂— | 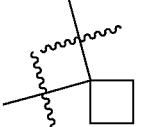 | 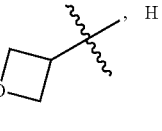, H |
| A-216. | 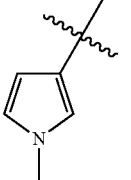 | —NH—(CH₂)₂— | 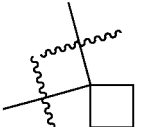 | 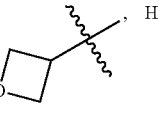, H |
| A-217. | 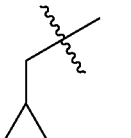 | —NH—CH₂— | 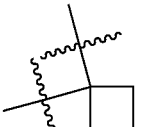 | 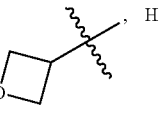, H |
| A-218. | 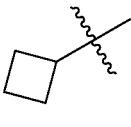 | —NH—CH₂— | 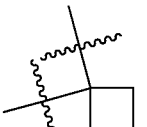 | 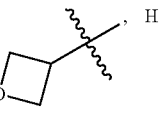, H |

-continued
| | R¹ | —Y—A²—X¹— | >CR¹²ᵃR¹²ᵇ | R⁴ᵃ, R⁴ᵇ |
|---|---|---|---|---|
| A-219. | 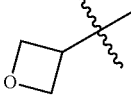 | —NH—CH₂— | 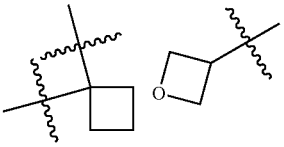 | , H |
| A-220. | 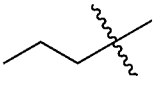 [SMILES: *CCC] | —NH—CH₂— | 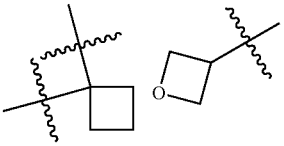 | , H |
| A-221. | 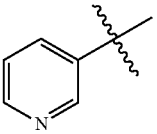 [SMILES: *c1cccnc1] | —NH—CH₂— | 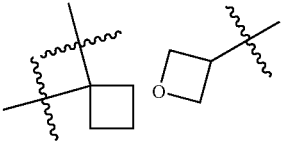 | , H |
| A-222. | 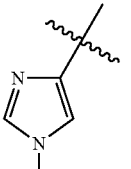 | —NH—CH₂— | 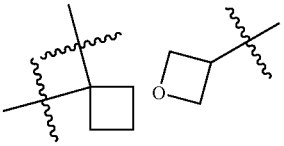 | , H |
| A-223. | 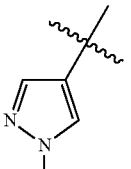 | —NH—CH₂— | 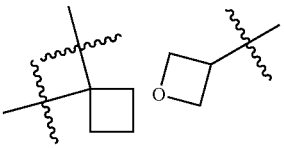 | , H |
| A-224. | 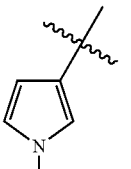 | —NH—CH₂— | 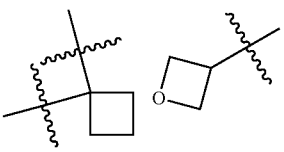 | , H |
| A-225. | 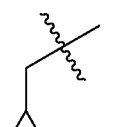 | 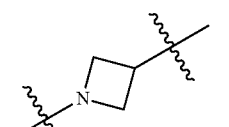 | 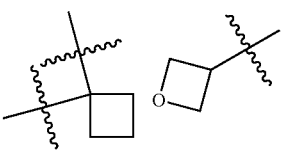 | , H |
| A-226. | 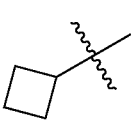 [SMILES: *C1CCC1] | 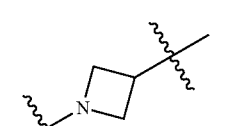 | 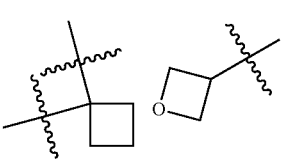 | , H |
| A-227. | 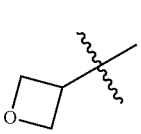 [SMILES: *C1COC1] | 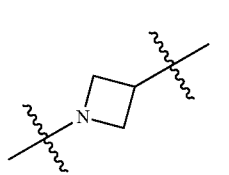 [SMILES: *C1CN(*)C1] | 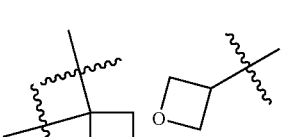 | , H |

-continued

| | R¹ | —Y—A²—X¹— | >CR$^{12a}$R$^{12b}$ | R$^{4a}$, R$^{4b}$ |
|---|---|---|---|---|
| A-228. | [propyl] | [azetidine] | [cyclobutane] | [oxetanyl], H |
| A-229. | [pyridin-3-yl] | [azetidine] | [cyclobutane] | [oxetanyl], H |
| A-230. | [1-methylimidazol-4-yl] | [azetidine] | [cyclobutane] | [oxetanyl], H |
| A-231. | [1-methylpyrazol-4-yl] | [azetidine] | [cyclobutane] | [oxetanyl], H |
| A-232. | [1-methylpyrrol-3-yl] | [azetidine] | [cyclobutane] | [oxetanyl], H |
| A-233. | [cyclopropylmethyl] | —(CH$_2$)$_2$— | [cyclobutane] | [oxetanyl], H |
| A-234. | [cyclobutyl] | —(CH$_2$)$_2$— | [cyclobutane] | [oxetanyl], H |
| A-235. | [oxetan-3-yl] | —(CH$_2$)$_2$— | [cyclobutane] | [oxetanyl], H |
| A-236. | [propyl] | —(CH$_2$)$_2$— | [cyclobutane] | [oxetanyl], H |

-continued
| | R¹ | —Y—A²—X¹— | >CR¹²ᵃR¹²ᵇ | R⁴ᵃ, R⁴ᵇ |
|---|---|---|---|---|
| A-237. |  | —(CH₂)₂— | | , H |
| A-238. | 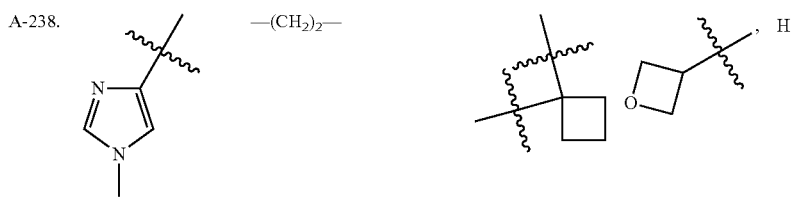 | —(CH₂)₂— | | , H |
| A-239. | 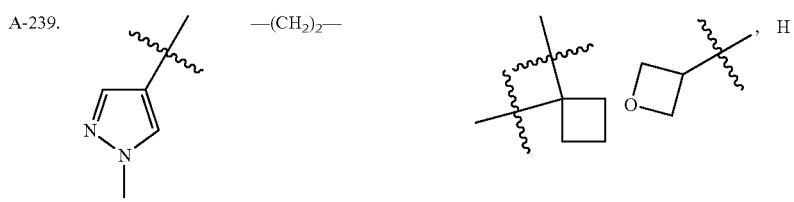 | —(CH₂)₂— | | , H |
| A-240. | 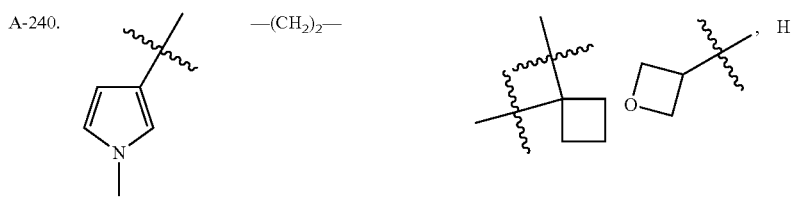 | —(CH₂)₂— | | , H |
| A-241. | 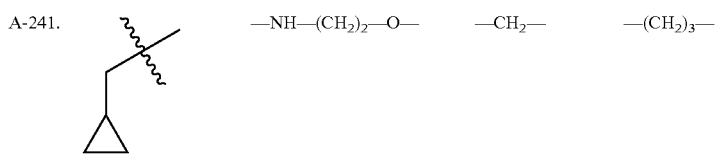 | —NH—(CH₂)₂—O— | —CH₂— | —(CH₂)₃— |
| A-242. | 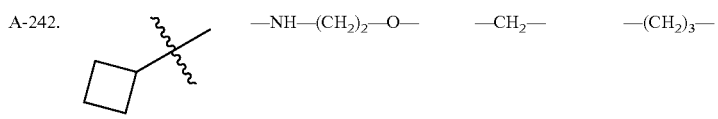 | —NH—(CH₂)₂—O— | —CH₂— | —(CH₂)₃— |
| A-243. | 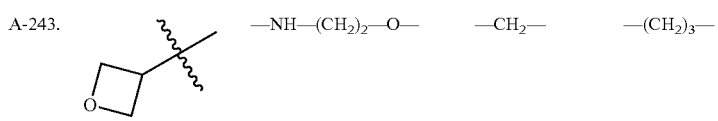 | —NH—(CH₂)₂—O— | —CH₂— | —(CH₂)₃— |
| A-244. | 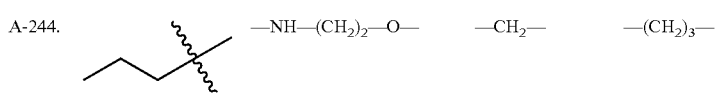 | —NH—(CH₂)₂—O— | —CH₂— | —(CH₂)₃— |
| A-245. | 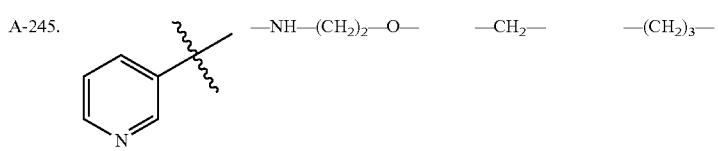 | —NH—(CH₂)₂—O— | —CH₂— | —(CH₂)₃— |

-continued
| R¹ | —Y—A²—X¹— | >CR¹²ᵃR¹²ᵇ | R⁴ᵃ, R⁴ᵇ |
|---|---|---|---|
| A-246. 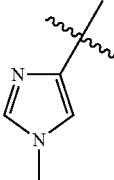 | —NH—(CH$_2$)$_2$—O— | —CH$_2$— | —(CH$_2$)$_3$— |
| A-247. 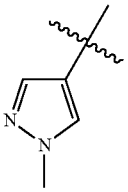 | —NH—(CH$_2$)$_2$—O— | —CH$_2$— | —(CH$_2$)$_3$— |
| A-248. 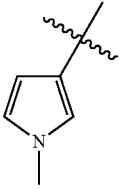 [SMILES: *c1ccn(C)c1] | —NH—(CH$_2$)$_2$—O— | —CH$_2$— | —(CH$_2$)$_3$— |
| A-249. 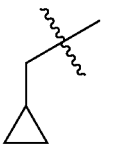 [SMILES: *CC1CC1] | —NH—(CH$_2$)$_2$— | —CH$_2$— | —(CH$_2$)$_3$— |
| A-250. 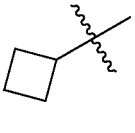 [SMILES: *C1CCC1] | —NH—(CH$_2$)$_2$— | —CH$_2$— | —(CH$_2$)$_3$— |
| A-251. 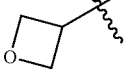 | —NH—(CH$_2$)$_2$— | —CH$_2$— | —(CH$_2$)$_3$— |
| A-252. 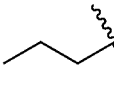 | —NH—(CH$_2$)$_2$— | —CH$_2$— | —(CH$_2$)$_3$— |
| A-253. 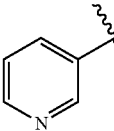 | —NH—(CH$_2$)$_2$— | —CH$_2$— | —(CH$_2$)$_3$— |
| A-254. 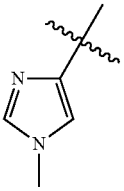 [SMILES: *c1cn(C)cn1] | —NH—(CH$_2$)$_2$— | —CH$_2$— | —(CH$_2$)$_3$— |

-continued
| R¹ | —Y—A²—X¹— | >CR¹²ᵃR¹²ᵇ | R⁴ᵃ, R⁴ᵇ |
|---|---|---|---|
| A-255. 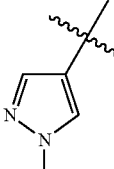 | —NH—(CH₂)₂— | —CH₂— | —(CH₂)₃— |
| A-256. 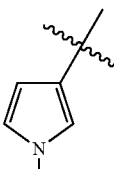 | —NH—(CH₂)₂— | —CH₂— | —(CH₂)₃— |
| A-257. 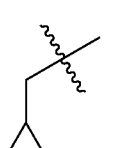 | —NH—CH₂— | —CH₂— | —(CH₂)₃— |
| A-258. 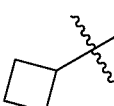 | —NH—CH₂— | —CH₂— | —(CH₂)₃— |
| A-259. 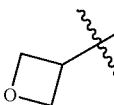 | —NH—CH₂— | —CH₂— | —(CH₂)₃— |
| A-260. 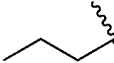 | —NH—CH₂— | —CH₂— | —(CH₂)₃— |
| A-261. 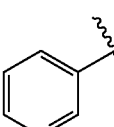 | —NH—CH₂— | —CH₂— | —(CH₂)₃— |
| A-262. 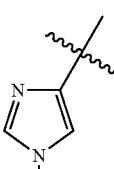 | —NH—CH₂— | —CH₂— | —(CH₂)₃— |
| A-263. 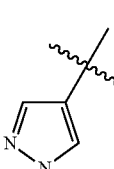 | —NH—CH₂— | —CH₂— | —(CH₂)₃— |

-continued
| | R¹ | —Y—A²—X¹— | >CR$^{12a}$R$^{12b}$ | R$^{4a}$, R$^{4b}$ |
|---|---|---|---|---|
| A-264. | 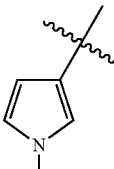 | —NH—CH$_2$— | —CH$_2$— | —(CH$_2$)$_3$— |
| A-265. | 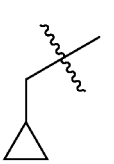 | 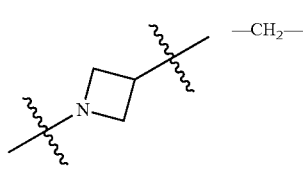 | —CH$_2$— | —(CH$_2$)$_3$— |
| A-266. | 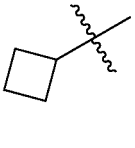 | 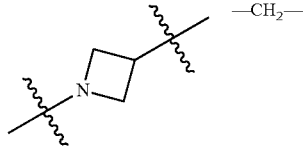 | —CH$_2$— | —(CH$_2$)$_3$— |
| A-267. | 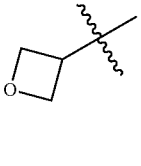 [SMILES: *C1COC1] | 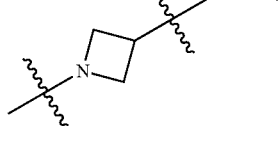 | —CH$_2$— | —(CH$_2$)$_3$— |
| A-268. | 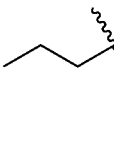 | 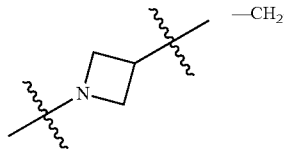 | —CH$_2$— | —(CH$_2$)$_3$— |
| A-269. | 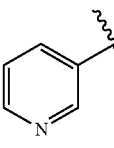 | 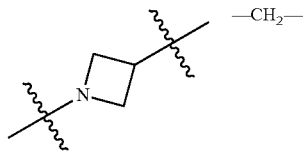 | —CH$_2$— | —(CH$_2$)$_3$— |
| A-270. | 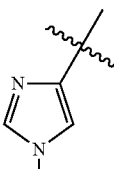 | 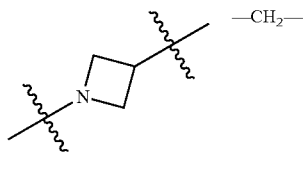 | —CH$_2$— | —(CH$_2$)$_3$— |
| A-271. | 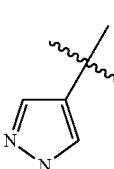 | 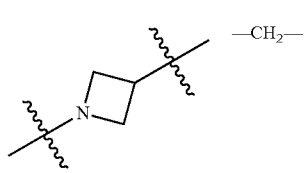 | —CH$_2$— | —(CH$_2$)$_3$— |

-continued

| | R¹ | —Y—A²—X¹— | >CR$^{12a}$R$^{12b}$ | R$^{4a}$, R$^{4b}$ |
|---|---|---|---|---|
| A-272. | (1-methylpyrrol-3-yl) | (azetidin-3-yl, N-linked) | —CH$_2$— | —(CH$_2$)$_3$— |
| A-273. | (cyclopropylmethyl) | —(CH$_2$)$_2$— | —CH$_2$— | —(CH$_2$)$_3$— |
| A-274. | (cyclobutyl) | —(CH$_2$)$_2$— | —CH$_2$— | —(CH$_2$)$_3$— |
| A-275. | (oxetan-3-yl) | —(CH$_2$)$_2$— | —CH$_2$— | —(CH$_2$)$_3$— |
| A-276. | (sec-butyl) | —(CH$_2$)$_2$— | —CH$_2$— | —(CH$_2$)$_3$— |
| A-277. | (pyridin-3-yl) | —(CH$_2$)$_2$— | —CH$_2$— | —(CH$_2$)$_3$— |
| A-278. | (1-methylimidazol-4-yl) | —(CH$_2$)$_2$— | —CH$_2$— | —(CH$_2$)$_3$— |
| A-279. | (1-methylpyrazol-4-yl) | —(CH$_2$)$_2$— | —CH$_2$— | —(CH$_2$)$_3$— |
| A-280. | (1-methylpyrrol-3-yl) | —(CH$_2$)$_2$— | —CH$_2$— | —(CH$_2$)$_3$— |

-continued

| | R¹ | —Y—A²—X¹— | >CR¹²ᵃR¹²ᵇ | R⁴ᵃ, R⁴ᵇ |
|---|---|---|---|---|
| A-281. | cyclopropylmethyl | —NH—(CH₂)₂—O— | cyclobutyl | —(CH₂)₃— |
| A-282. | cyclobutyl | —NH—(CH₂)₂—O— | cyclobutyl | —(CH₂)₃— |
| A-283. | oxetan-3-yl | —NH—(CH₂)₂—O— | cyclobutyl | —(CH₂)₃— |
| A-284. | sec-pentyl | —NH—(CH₂)₂—O— | cyclobutyl | —(CH₂)₃— |
| A-285. | pyridin-3-yl | —NH—(CH₂)₂—O— | cyclobutyl | —(CH₂)₃— |
| A-286. | 1-methyl-1H-imidazol-4-yl | —NH—(CH₂)₂—O— | cyclobutyl | —(CH₂)₃— |
| A-287. | 1-methyl-1H-pyrazol-4-yl | —NH—(CH₂)₂—O— | cyclobutyl | —(CH₂)₃— |
| A-288. | 1-methyl-1H-pyrrol-3-yl | —NH—(CH₂)₂—O— | cyclobutyl | —(CH₂)₃— |
| A-289. | cyclopropylmethyl | —NH—(CH₂)₂— | cyclobutyl | —(CH₂)₃— |

-continued

| | R¹ | —Y—A²—X¹— | >CR$^{12a}$R$^{12b}$ | R$^{4a}$, R$^{4b}$ |
|---|---|---|---|---|
| A-290. | cyclobutyl | —NH—(CH$_2$)$_2$— | cyclobutylidene | —(CH$_2$)$_3$— |
| A-291. | oxetanyl | —NH—(CH$_2$)$_2$— | cyclobutylidene | —(CH$_2$)$_3$— |
| A-292. | sec-butyl | —NH—(CH$_2$)$_2$— | cyclobutylidene | —(CH$_2$)$_3$— |
| A-293. | pyridin-3-yl | —NH—(CH$_2$)$_2$— | cyclobutylidene | —(CH$_2$)$_3$— |
| A-294. | 1-methylimidazol-4-yl | —NH—(CH$_2$)$_2$— | cyclobutylidene | —(CH$_2$)$_3$— |
| A-295. | 1-methylpyrazol-4-yl | —NH—(CH$_2$)$_2$— | cyclobutylidene | —(CH$_2$)$_3$— |
| A-296. | 1-methylpyrrol-3-yl | —NH—(CH$_2$)$_2$— | cyclobutylidene | —(CH$_2$)$_3$— |
| A-297. | cyclopropylmethyl | —NH—CH$_2$— | cyclobutylidene | —(CH$_2$)$_3$— |
| A-298. | cyclobutyl | —NH—CH$_2$— | cyclobutylidene | —(CH$_2$)$_3$— |

-continued
| | R¹ | —Y—A²—X¹— | >CR^{12a}R^{12b} | R^{4a}, R^{4b} |
|---|---|---|---|---|
| A-299. | 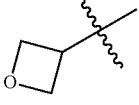 | —NH—CH₂— | 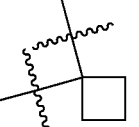 | —(CH₂)₃— |
| A-300. | 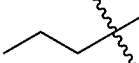 | —NH—CH₂— | 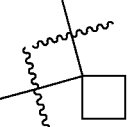 | —(CH₂)₃— |
| A-301. | 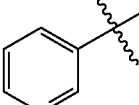 | —NH—CH₂— | 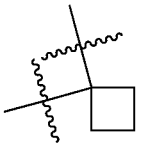 | —(CH₂)₃— |
| A-302. | 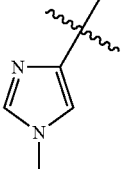 | —NH—CH₂— | 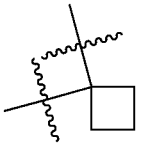 [SMILES: *C1(*)CCC1] | —(CH₂)₃— |
| A-303. | 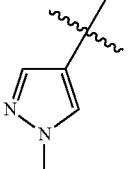 | —NH—CH₂— | 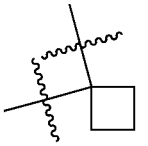 [SMILES: *C1(*)CCC1] | —(CH₂)₃— |
| A-304. | 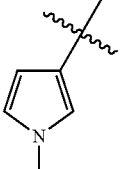 | —NH—CH₂— | 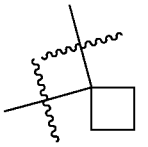 [SMILES: *C1(*)CCC1] | —(CH₂)₃— |
| A-305. | 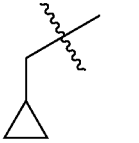 [SMILES: *CC1CC1] | 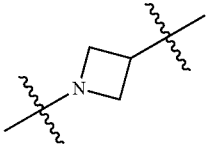 [SMILES: *C1CN(*)C1] | 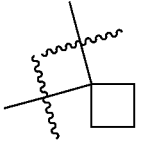 [SMILES: *C1(*)CCC1] | —(CH₂)₃— |
| A-306. | 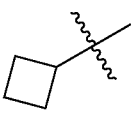 [SMILES: *C1CCC1] | 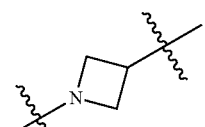 | 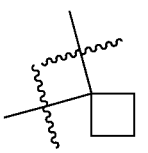 | —(CH₂)₃— |
| A-307. | 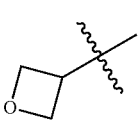 [SMILES: *C1COC1] | 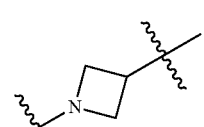 | 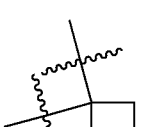 | —(CH₂)₃— |

-continued

| | R¹ | —Y—A²—X¹— | >CR$^{12a}$R$^{12b}$ | R$^{4a}$, R$^{4b}$ |
|---|---|---|---|---|
| A-308. | (propyl group) | (azetidine) | (cyclobutyl) | —(CH$_2$)$_3$— |
| A-309. | (pyridin-3-yl) | (azetidine) | (cyclobutyl) | —(CH$_2$)$_3$— |
| A-310. | (1-methylimidazol-4-yl) | (azetidine) | (cyclobutyl) | —(CH$_2$)$_3$— |
| A-311. | (1-methylpyrazol-4-yl) | (azetidine) | (cyclobutyl) | —(CH$_2$)$_3$— |
| A-312. | (1-methylpyrrol-3-yl) | (azetidine) | (cyclobutyl) | —(CH$_2$)$_3$— |
| A-313. | (cyclopropylmethyl) | —(CH$_2$)$_2$— | (cyclobutyl) | —(CH$_2$)$_3$— |
| A-314. | (cyclobutyl) | —(CH$_2$)$_2$— | (cyclobutyl) | —(CH$_2$)$_3$— |
| A-315. | (oxetan-3-yl) | —(CH$_2$)$_2$— | (cyclobutyl) | —(CH$_2$)$_3$— |
| A-316. | (propyl) | —(CH$_2$)$_2$— | (cyclobutyl) | —(CH$_2$)$_3$— |

-continued
| | R$^1$ | —Y—A$^2$—X$^1$— | >CR$^{12a}$R$^{12b}$ | R$^{4a}$, R$^{4b}$ |
|---|---|---|---|---|
| A-317. | 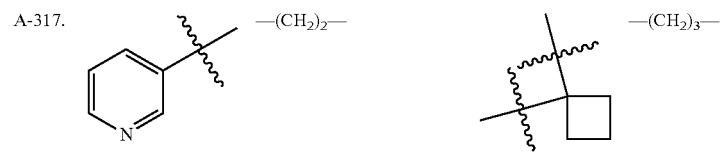 | —(CH$_2$)$_2$— | 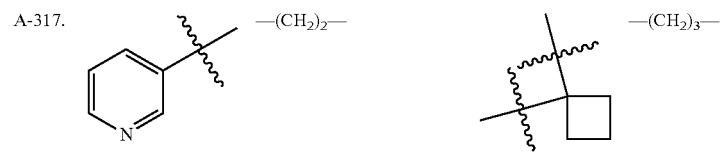 | —(CH$_2$)$_3$— |
| A-318. | 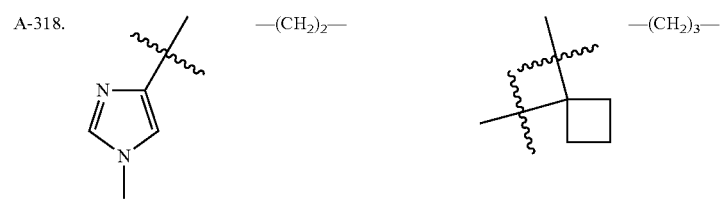 | —(CH$_2$)$_2$— | 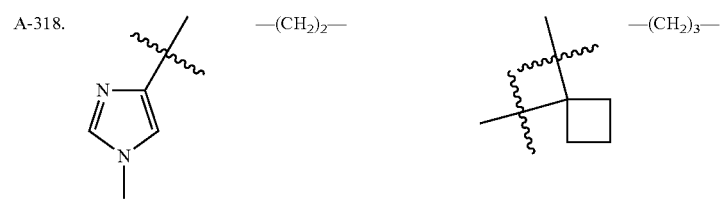 | —(CH$_2$)$_3$— |
| A-319. | 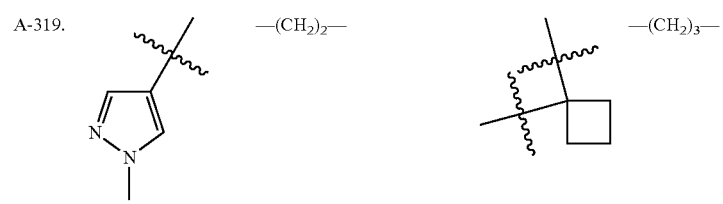 | —(CH$_2$)$_2$— | 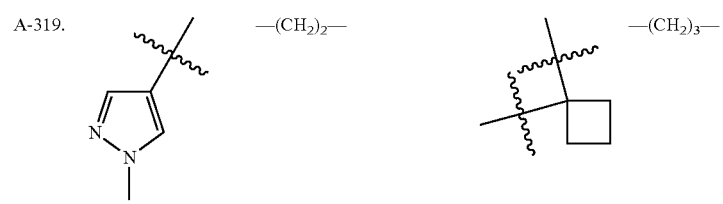 | —(CH$_2$)$_3$— |
| A-320. | 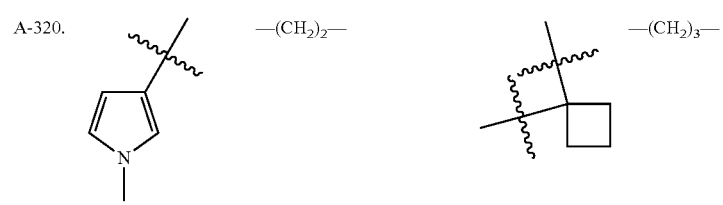 | —(CH$_2$)$_2$— | 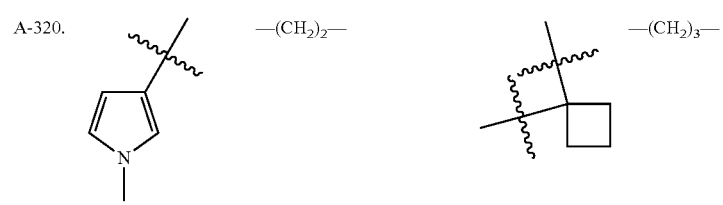 | —(CH$_2$)$_3$— |
| A-321. | 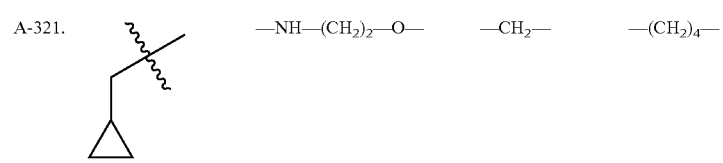 | —NH—(CH$_2$)$_2$—O— | —CH$_2$— | —(CH$_2$)$_4$— |
| A-322. | 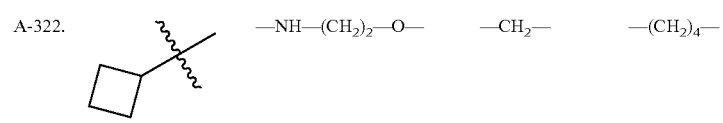 | —NH—(CH$_2$)$_2$—O— | —CH$_2$— | —(CH$_2$)$_4$— |
| A-323. | 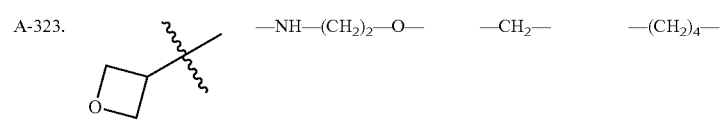 | —NH—(CH$_2$)$_2$—O— | —CH$_2$— | —(CH$_2$)$_4$— |
| A-324. | 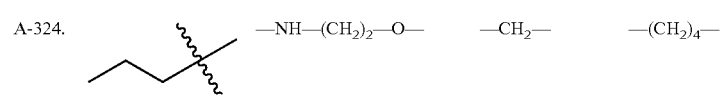 | —NH—(CH$_2$)$_2$—O— | —CH$_2$— | —(CH$_2$)$_4$— |
| A-325. | 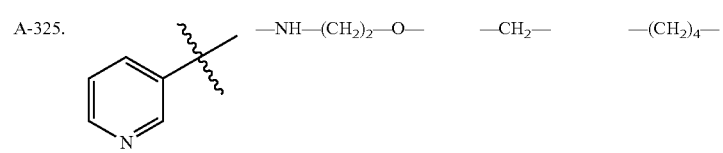 | —NH—(CH$_2$)$_2$—O— | —CH$_2$— | —(CH$_2$)$_4$— |

-continued
| R¹ | —Y—A²—X¹— | >CR$^{12a}$R$^{12b}$ | R$^{4a}$, R$^{4b}$ |
|---|---|---|---|
| A-326. 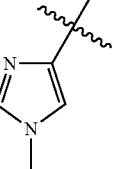 | —NH—(CH$_2$)$_2$—O— | —CH$_2$— | —(CH$_2$)$_4$— |
| A-327. 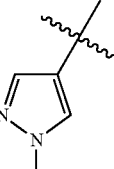 | —NH—(CH$_2$)$_2$—O— | —CH$_2$— | —(CH$_2$)$_4$— |
| A-328. 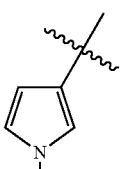 | —NH—(CH$_2$)$_2$—O— | —CH$_2$— | —(CH$_2$)$_4$— |
| A-329. 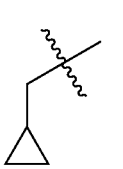 [SMILES: *CC1CC1] | —NH—(CH$_2$)$_2$— | —CH$_2$— | —(CH$_2$)$_4$— |
| A-330.  | —NH—(CH$_2$)$_2$— | —CH$_2$— | —(CH$_2$)$_4$— |
| A-331. 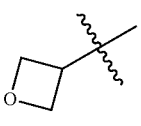 [SMILES: *C1COC1] | —NH—(CH$_2$)$_2$— | —CH$_2$— | —(CH$_2$)$_4$— |
| A-332. 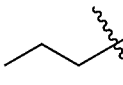 | —NH—(CH$_2$)$_2$— | —CH$_2$— | —(CH$_2$)$_4$— |
| A-333. 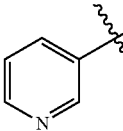 | —NH—(CH$_2$)$_2$— | —CH$_2$— | —(CH$_2$)$_4$— |
| A-334. 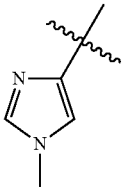 [SMILES: *c1cn(C)cn1] | —NH—(CH$_2$)$_2$— | —CH$_2$— | —(CH$_2$)$_4$— |

-continued
| R¹ | —Y—A²—X¹— | >CR¹²ᵃR¹²ᵇ | R⁴ᵃ, R⁴ᵇ |
|---|---|---|---|
| A-335. 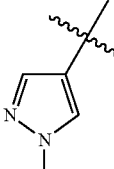 | —NH—(CH₂)₂— | —CH₂— | —(CH₂)₄— |
| A-336. 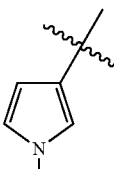 | —NH—(CH₂)₂— | —CH₂— | —(CH₂)₄— |
| A-337. 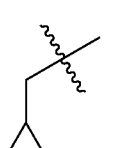 | —NH—CH₂— | —CH₂— | —(CH₂)₄— |
| A-338. 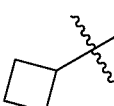 | —NH—CH₂— | —CH₂— | —(CH₂)₄— |
| A-339. 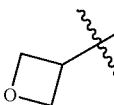 | —NH—CH₂— | —CH₂— | —(CH₂)₄— |
| A-340. 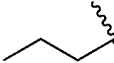 | —NH—CH₂— | —CH₂— | —(CH₂)₄— |
| A-341. 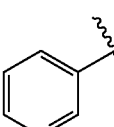 | —NH—CH₂— | —CH₂— | —(CH₂)₄— |
| A-342. 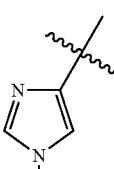 | —NH—CH₂— | —CH₂— | —(CH₂)₄— |
| A-343. 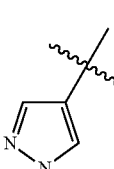 | —NH—CH₂— | —CH₂— | —(CH₂)₄— |

-continued
| | R$^1$ | —Y—A$^2$—X$^1$— | >CR$^{12a}$R$^{12b}$ | R$^{4a}$, R$^{4b}$ |
|---|---|---|---|---|
| A-344. | 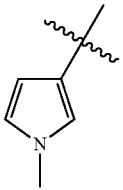 [SMILES: *c1ccn(C)c1] | —NH—CH$_2$— | —CH$_2$— | —(CH$_2$)$_4$— |
| A-345. | 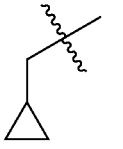 | 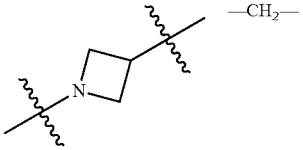 | —CH$_2$— | —(CH$_2$)$_4$— |
| A-346. | 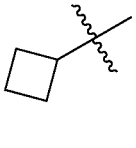 | 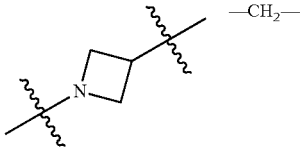 | —CH$_2$— | —(CH$_2$)$_4$— |
| A-347. | 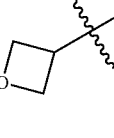 | 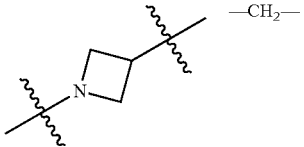 | —CH$_2$— | —(CH$_2$)$_4$— |
| A-348. | 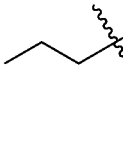 | 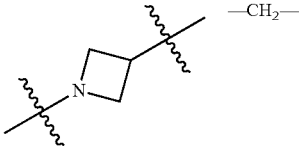 | —CH$_2$— | —(CH$_2$)$_4$— |
| A-349. | 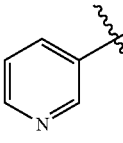 | 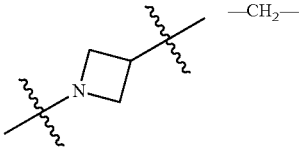 | —CH$_2$— | —(CH$_2$)$_4$— |
| A-350. | 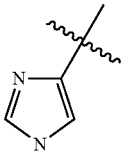 | 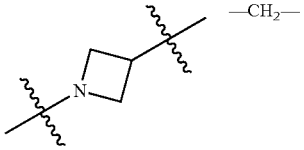 | —CH$_2$— | —(CH$_2$)$_4$— |
| A-351. | 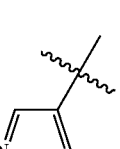 | 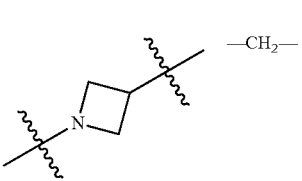 | —CH$_2$— | —(CH$_2$)$_4$— |

-continued
| | R¹ | —Y—A²—X¹— | >CR¹²ᵃR¹²ᵇ | R⁴ᵃ, R⁴ᵇ |
|---|---|---|---|---|
| A-352. | 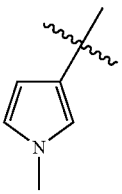 [SMILES: *c1ccn(C)c1] | 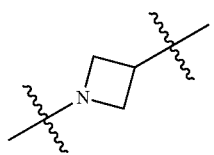 [SMILES: *C1CN(*)C1] | —CH₂— | —(CH₂)₄— |
| A-353. |  | —(CH₂)₂— | —CH₂— | —(CH₂)₄— |
| A-354. | 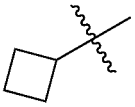 | —(CH₂)₂— | —CH₂— | —(CH₂)₄— |
| A-355. | 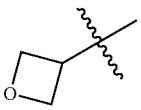 [SMILES: *C1COC1] | —(CH₂)₂— | —CH₂— | —(CH₂)₄— |
| A-356. | 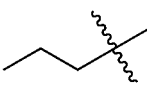 | —(CH₂)₂— | —CH₂— | —(CH₂)₄— |
| A-357. | 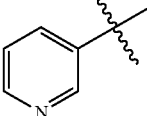 | —(CH₂)₂— | —CH₂— | —(CH₂)₄— |
| A-358. | 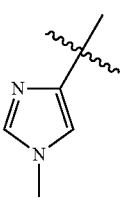 [SMILES: *c1cn(C)cn1] | —(CH₂)₂— | —CH₂— | —(CH₂)₄— |
| A-359. | 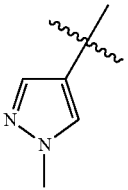 | —(CH₂)₂— | —CH₂— | —(CH₂)₄— |
| A-360. | 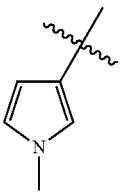 [SMILES: *c1ccn(C)c1] | —(CH₂)₂— | —CH₂— | —(CH₂)₄— |

-continued

| | R¹ | —Y—A²—X¹— | >CR¹²ᵃR¹²ᵇ | R⁴ᵃ, R⁴ᵇ |
|---|---|---|---|---|
| A-361. | cyclopropylmethyl | —NH—(CH$_2$)$_2$—O— | cyclobutyl | —(CH$_2$)$_4$— |
| A-362. | cyclobutyl | —NH—(CH$_2$)$_2$—O— | cyclobutyl | —(CH$_2$)$_4$— |
| A-363. | oxetan-3-yl | —NH—(CH$_2$)$_2$—O— | cyclobutyl | —(CH$_2$)$_4$— |
| A-364. | sec-butyl | —NH—(CH$_2$)$_2$—O— | cyclobutyl | —(CH$_2$)$_4$— |
| A-365. | pyridin-3-yl | —NH—(CH$_2$)$_2$—O— | cyclobutyl | —(CH$_2$)$_4$— |
| A-366. | 1-methyl-1H-imidazol-4-yl | —NH—(CH$_2$)$_2$—O— | cyclobutyl | —(CH$_2$)$_4$— |
| A-367. | 1-methyl-1H-pyrazol-4-yl | —NH—(CH$_2$)$_2$—O— | cyclobutyl | —(CH$_2$)$_4$— |
| A-368. | 1-methyl-1H-pyrrol-3-yl | —NH—(CH$_2$)$_2$—O— | cyclobutyl | —(CH$_2$)$_4$— |
| A-369. | cyclopropylmethyl | —NH—(CH$_2$)$_2$— | cyclobutyl | —(CH$_2$)$_4$— |

-continued

| | R¹ | —Y—A²—X¹— | >CR$^{12a}$R$^{12b}$ | R$^{4a}$, R$^{4b}$ |
|---|---|---|---|---|
| A-370. | cyclobutyl | —NH—(CH$_2$)$_2$— | cyclobutylidene | —(CH$_2$)$_4$— |
| A-371. | oxetan-3-yl | —NH—(CH$_2$)$_2$— | cyclobutylidene | —(CH$_2$)$_4$— |
| A-372. | n-butyl | —NH—(CH$_2$)$_2$— | cyclobutylidene | —(CH$_2$)$_4$— |
| A-373. | pyridin-3-yl | —NH—(CH$_2$)$_2$— | cyclobutylidene | —(CH$_2$)$_4$— |
| A-374. | 1-methyl-1H-imidazol-4-yl | —NH—(CH$_2$)$_2$— | cyclobutylidene | —(CH$_2$)$_4$— |
| A-375. | 1-methyl-1H-pyrazol-4-yl | —NH—(CH$_2$)$_2$— | cyclobutylidene | —(CH$_2$)$_4$— |
| A-376. | 1-methyl-1H-pyrrol-3-yl | —NH—(CH$_2$)$_2$— | cyclobutylidene | —(CH$_2$)$_4$— |
| A-377. | cyclopropylmethyl | —NH—CH$_2$— | cyclobutylidene | —(CH$_2$)$_4$— |
| A-378. | cyclobutyl | —NH—CH$_2$— | cyclobutylidene | —(CH$_2$)$_4$— |

-continued
| | R¹ | —Y—A²—X¹— | >CR¹²ᵃR¹²ᵇ | R⁴ᵃ, R⁴ᵇ |
|---|---|---|---|---|
| A-379. | 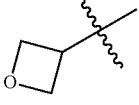 | —NH—CH₂— | 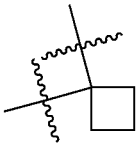 [SMILES: *C1(*)CCC1] | —(CH₂)₄— |
| A-380. |  | —NH—CH₂— | 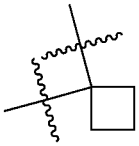 [SMILES: *C1(*)CCC1] | —(CH₂)₄— |
| A-381. | 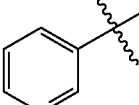 | —NH—CH₂— | 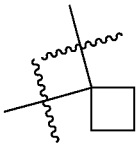 | —(CH₂)₄— |
| A-382. | 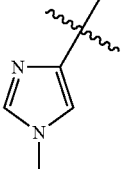 | —NH—CH₂— | 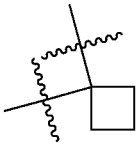 [SMILES: *C1(*)CCC1] | —(CH₂)₄— |
| A-383. | 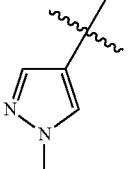 | —NH—CH₂— | 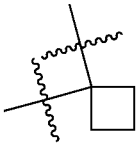 [SMILES: *C1(*)CCC1] | —(CH₂)₄— |
| A-384. | 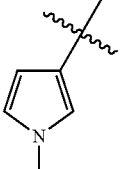 | —NH—CH₂— | 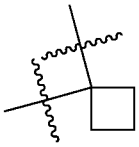 [SMILES: *C1(*)CCC1] | —(CH₂)₄— |
| A-385. | 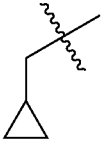 [SMILES: *CC1CC1] | 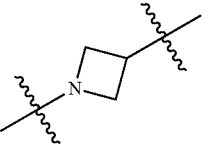 [SMILES: *C1CN(*)C1] | 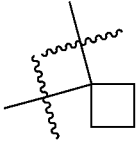 [SMILES: *C1(*)CCC1] | —(CH₂)₄— |
| A-386. | 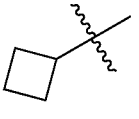 [SMILES: *C1CCC1] | 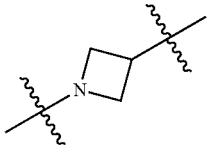 [SMILES: *C1CN(*)C1] | 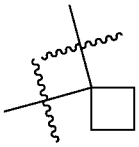 | —(CH₂)₄— |
| A-387. | 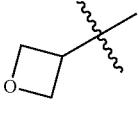 [SMILES: *C1COC1] | 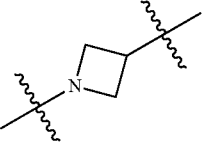 [SMILES: *C1CN(*)C1] | 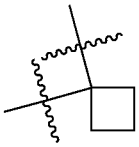 | —(CH₂)₄— |

-continued

| | R¹ | —Y—A²—X¹— | >CR¹²ᵃR¹²ᵇ | R⁴ᵃ, R⁴ᵇ |
|---|---|---|---|---|
| A-388. | (butyl) | azetidine | cyclobutane | —(CH₂)₄— |
| A-389. | pyridin-3-yl | azetidine | cyclobutane | —(CH₂)₄— |
| A-390. | 1-methylimidazol-4-yl | azetidine | cyclobutane | —(CH₂)₄— |
| A-391. | 1-methylpyrazol-4-yl | azetidine | cyclobutane | —(CH₂)₄— |
| A-392. | 1-methylpyrrol-3-yl | azetidine | cyclobutane | —(CH₂)₄— |
| A-393. | cyclopropylmethyl | —(CH₂)₂— | cyclobutane | —(CH₂)₄— |
| A-394. | cyclobutyl | —(CH₂)₂— | cyclobutane | —(CH₂)₄— |
| A-395. | oxetan-3-yl | —(CH₂)₂— | cyclobutane | —(CH₂)₄— |
| A-396. | propyl | —(CH₂)₂— | cyclobutane | —(CH₂)₄— |

-continued
| | $R^1$ | $-Y-A^2-X^1-$ | $>CR^{12a}R^{12b}$ | $R^{4a}, R^{4b}$ |
|---|---|---|---|---|
| A-397. | 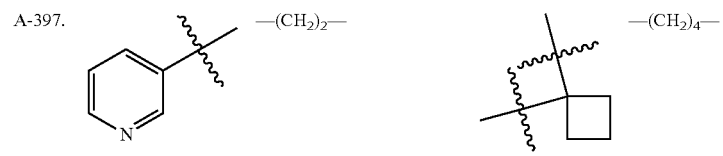 | $-(CH_2)_2-$ | | $-(CH_2)_4-$ |
| A-398. | 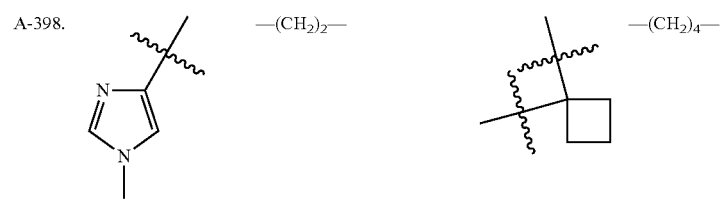 | $-(CH_2)_2-$ | | $-(CH_2)_4-$ |
| A-399. | 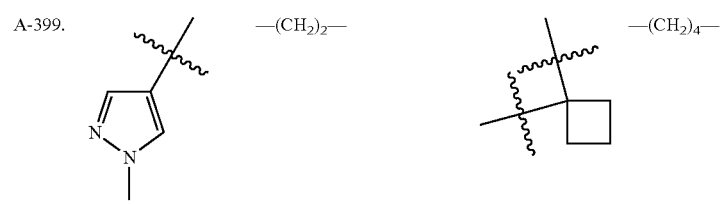 | $-(CH_2)_2-$ | | $-(CH_2)_4-$ |
| A-400. | 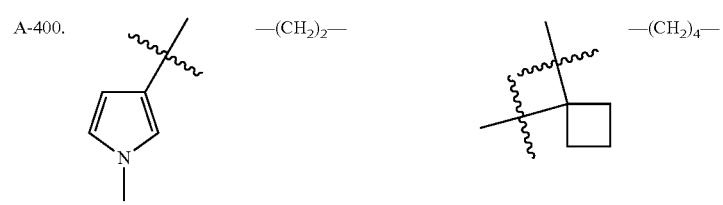 | $-(CH_2)_2-$ | | $-(CH_2)_4-$ |
| A-401. | 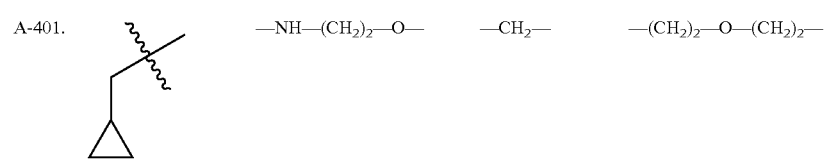 | $-NH-(CH_2)_2-O-$ | $-CH_2-$ | $-(CH_2)_2-O-(CH_2)_2-$ |
| A-402. | 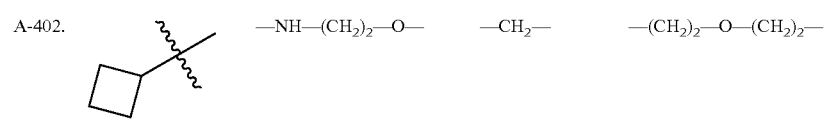 | $-NH-(CH_2)_2-O-$ | $-CH_2-$ | $-(CH_2)_2-O-(CH_2)_2-$ |
| A-403. | 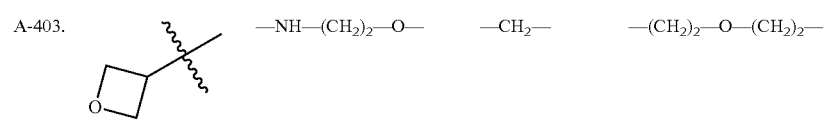 | $-NH-(CH_2)_2-O-$ | $-CH_2-$ | $-(CH_2)_2-O-(CH_2)_2-$ |
| A-404. | 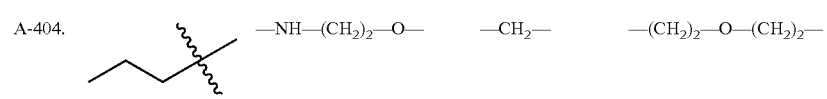 | $-NH-(CH_2)_2-O-$ | $-CH_2-$ | $-(CH_2)_2-O-(CH_2)_2-$ |
| A-405. | 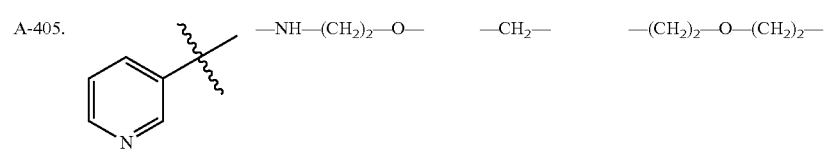 | $-NH-(CH_2)_2-O-$ | $-CH_2-$ | $-(CH_2)_2-O-(CH_2)_2-$ |

-continued
| | R¹ | —Y—A²—X¹— | >CR¹²ᵃR¹²ᵇ | R⁴ᵃ, R⁴ᵇ |
|---|---|---|---|---|
| A-406. | 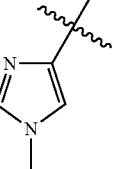 | —NH—(CH₂)₂—O— | —CH₂— | —(CH₂)₂—O—(CH₂)₂— |
| A-407. | 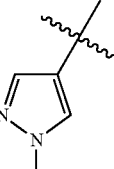 | —NH—(CH₂)₂—O— | —CH₂— | —(CH₂)₂—O—(CH₂)₂— |
| A-408. | 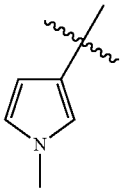 [SMILES: *c1ccn(C)c1] | —NH—(CH₂)₂—O— | —CH₂— | —(CH₂)₂—O—(CH₂)₂— |
| A-409. | 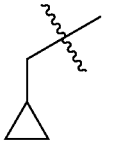 [SMILES: *CC1CC1] | —NH—(CH₂)₂— | —CH₂— | —(CH₂)₂—O—(CH₂)₂— |
| A-410. | 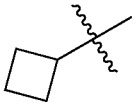 [SMILES: *C1CCC1] | —NH—(CH₂)₂— | —CH₂— | —(CH₂)₂—O—(CH₂)₂— |
| A-411. | 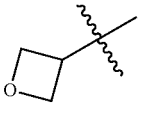 [SMILES: *C1COC1] | —NH—(CH₂)₂— | —CH₂— | —(CH₂)₂—O—(CH₂)₂— |
| A-412. | 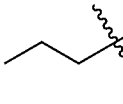 | —NH—(CH₂)₂— | —CH₂— | —(CH₂)₂—O—(CH₂)₂— |
| A-413. | 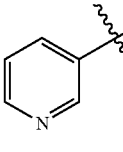 | —NH—(CH₂)₂— | —CH₂— | —(CH₂)₂—O—(CH₂)₂— |
| A-414. | 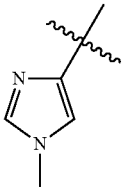 [SMILES: *c1cn(C)cn1] | —NH—(CH₂)₂— | —CH₂— | —(CH₂)₂—O—(CH₂)₂— |

-continued
| | R¹ | —Y—A²—X¹— | >CR¹²ᵃR¹²ᵇ | R⁴ᵃ, R⁴ᵇ |
|---|---|---|---|---|
| A-415. | 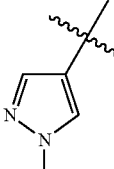 | —NH—(CH₂)₂— | —CH₂— | —(CH₂)₂—O—(CH₂)₂— |
| A-416. | 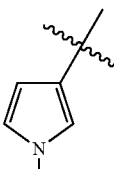 | —NH—(CH₂)₂— | —CH₂— | —(CH₂)₂—O—(CH₂)₂— |
| A-417. | 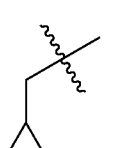 | —NH—CH₂— | —CH₂— | —(CH₂)₂—O—(CH₂)₂— |
| A-418. | 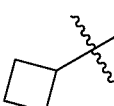 | —NH—CH₂— | —CH₂— | —(CH₂)₂—O—(CH₂)₂— |
| A-419. | 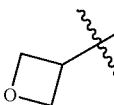 | —NH—CH₂— | —CH₂— | —(CH₂)₂—O—(CH₂)₂— |
| A-420. | 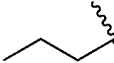 | —NH—CH₂— | —CH₂— | —(CH₂)₂—O—(CH₂)₂— |
| A-421. | 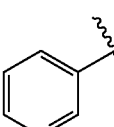 | —NH—CH₂— | —CH₂— | —(CH₂)₂—O—(CH₂)₂— |
| A-422. | 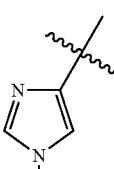 | —NH—CH₂— | —CH₂— | —(CH₂)₂—O—(CH₂)₂— |
| A-423. | 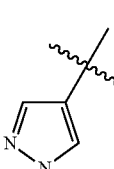 | —NH—CH₂— | —CH₂— | —(CH₂)₂—O—(CH₂)₂— |

| | R¹ | —Y—A²—X¹— | >CR¹²ᵃR¹²ᵇ | R⁴ᵃ, R⁴ᵇ |
|---|---|---|---|---|
| A-424. | 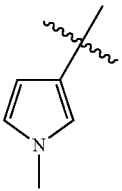 [SMILES: *c1ccn(C)c1] | —NH—CH₂— | —CH₂— | —(CH₂)₂—O—(CH₂)₂— |
| A-425. | 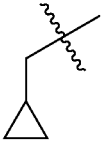 | 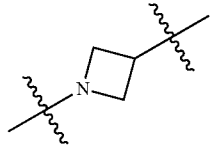 [SMILES: *C1CN(*)C1] | —CH₂— | —(CH₂)₂—O—(CH₂)₂— |
| A-426. | 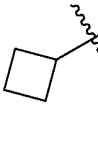 | 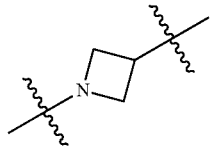 [SMILES: *C1CN(*)C1] | —CH₂— | —(CH₂)₂—O—(CH₂)₂— |
| A-427. | 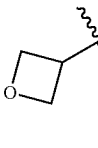 | 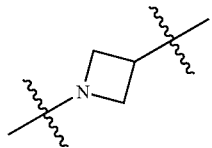 [SMILES: *C1CN(*)C1] | —CH₂— | —(CH₂)₂—O—(CH₂)₂— |
| A-428. | 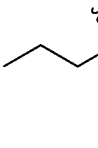 | 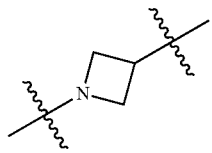 [SMILES: *C1CN(*)C1] | —CH₂— | —(CH₂)₂—O—(CH₂)₂— |
| A-429. | 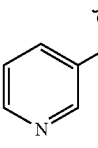 | | —CH₂— | —(CH₂)₂—O—(CH₂)₂— |
| A-430. | 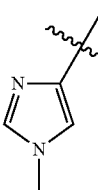 | | —CH₂— | —(CH₂)₂—O—(CH₂)₂— |
| A-431. | 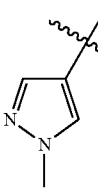 | | —CH₂— | —(CH₂)₂—O—(CH₂)₂— |

-continued
| | R¹ | —Y—A²—X¹— | >CR¹²ᵃR¹²ᵇ | R⁴ᵃ, R⁴ᵇ |
|---|---|---|---|---|
| A-432. | 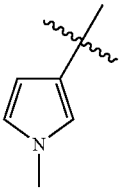 [SMILES: *c1ccn(C)c1] | 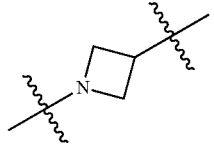 [SMILES: *C1CN(*)C1] | —CH₂— | —(CH₂)₂—O—(CH₂)₂— |
| A-433. | 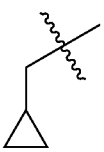 | —(CH₂)₂— | —CH₂— | —(CH₂)₂—O—(CH₂)₂— |
| A-434. | 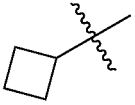 | —(CH₂)₂— | —CH₂— | —(CH₂)₂—O—(CH₂)₂— |
| A-435. | 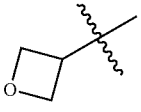 [SMILES: *C1COC1] | —(CH₂)₂— | —CH₂— | —(CH₂)₂—O—(CH₂)₂— |
| A-436. | 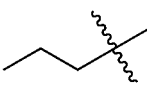 | —(CH₂)₂— | —CH₂— | —(CH₂)₂—O—(CH₂)₂— |
| A-437. | 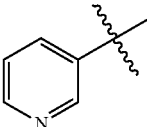 | —(CH₂)₂— | —CH₂— | —(CH₂)₂—O—(CH₂)₂— |
| A-438. | 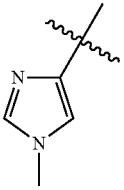 [SMILES: *c1cn(C)cn1] | —(CH₂)₂— | —CH₂— | —(CH₂)₂—O—(CH₂)₂— |
| A-439. | 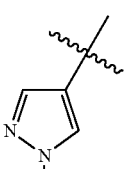 | —(CH₂)₂— | —CH₂— | —(CH₂)₂—O—(CH₂)₂— |
| A-440. | 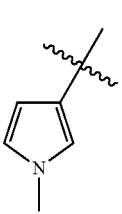 [SMILES: *c1ccn(C)c1] | —(CH₂)₂— | —CH₂— | —(CH₂)₂—O—(CH₂)₂— |

| | R¹ | —Y—A²—X¹— | >CR$^{12a}$R$^{12b}$ | R$^{4a}$, R$^{4b}$ |
|---|---|---|---|---|
| A-441. | 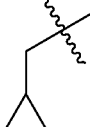 | —NH—(CH$_2$)$_2$—O— | 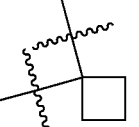 | —(CH$_2$)$_2$—O—(CH$_2$)$_2$— |
| A-442. |  | —NH—(CH$_2$)$_2$—O— | 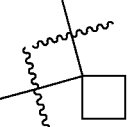 | —(CH$_2$)$_2$—O—(CH$_2$)$_2$— |
| A-443. | 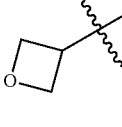 | —NH—(CH$_2$)$_2$—O— | 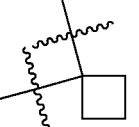 | —(CH$_2$)$_2$—O—(CH$_2$)$_2$— |
| A-444. | 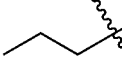 | —NH—(CH$_2$)$_2$—O— | 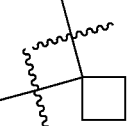 | —(CH$_2$)$_2$—O—(CH$_2$)$_2$— |
| A-445. | 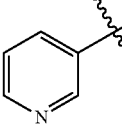 | —NH—(CH$_2$)$_2$—O— | 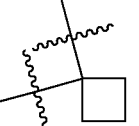 | —(CH$_2$)$_2$—O—(CH$_2$)$_2$— |
| A-446. | 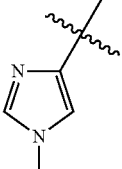 | —NH—(CH$_2$)$_2$—O— | 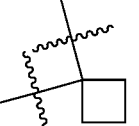 | —(CH$_2$)$_2$—O—(CH$_2$)$_2$— |
| A-447. | 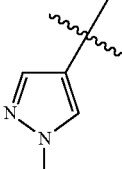 | —NH—(CH$_2$)$_2$—O— | 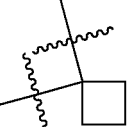 | —(CH$_2$)$_2$—O—(CH$_2$)$_2$— |
| A-448. | 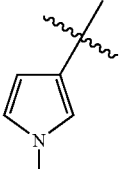 | —NH—(CH$_2$)$_2$—O— | 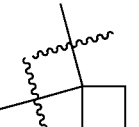 | —(CH$_2$)$_2$—O—(CH$_2$)$_2$— |
| A-449. | 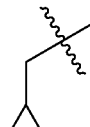 | —NH—(CH$_2$)$_2$— | 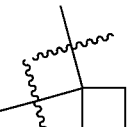 | —(CH$_2$)$_2$—O—(CH$_2$)$_2$— |

-continued

| | R¹ | —Y—A²—X¹— | >CR$^{12a}$R$^{12b}$ | R$^{4a}$, R$^{4b}$ |
|---|---|---|---|---|
| A-450. | cyclobutyl | —NH—(CH$_2$)$_2$— | cyclobutyl | —(CH$_2$)$_2$—O—(CH$_2$)$_2$— |
| A-451. | oxetanyl | —NH—(CH$_2$)$_2$— | cyclobutyl | —(CH$_2$)$_2$—O—(CH$_2$)$_2$— |
| A-452. | propyl | —NH—(CH$_2$)$_2$— | cyclobutyl | —(CH$_2$)$_2$—O—(CH$_2$)$_2$— |
| A-453. | pyridyl | —NH—(CH$_2$)$_2$— | cyclobutyl | —(CH$_2$)$_2$—O—(CH$_2$)$_2$— |
| A-454. | N-methylimidazolyl | —NH—(CH$_2$)$_2$— | cyclobutyl | —(CH$_2$)$_2$—O—(CH$_2$)$_2$— |
| A-455. | N-methylpyrazolyl | —NH—(CH$_2$)$_2$— | cyclobutyl | —(CH$_2$)$_2$—O—(CH$_2$)$_2$— |
| A-456. | N-methylpyrrolyl | —NH—(CH$_2$)$_2$— | cyclobutyl | —(CH$_2$)$_2$—O—(CH$_2$)$_2$— |
| A-457. | cyclopropylmethyl | —NH—CH$_2$— | cyclobutyl | —(CH$_2$)$_2$—O—(CH$_2$)$_2$— |
| A-458. | cyclobutyl | —NH—CH$_2$— | cyclobutyl | —(CH$_2$)$_2$—O—(CH$_2$)$_2$— |

US 8,877,794 B2
-continued
| | R¹ | —Y—A²—X¹— | >CR¹²ᵃR¹²ᵇ | R⁴ᵃ, R⁴ᵇ |
|---|---|---|---|---|
| A-459. | 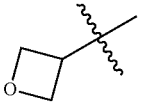 [SMILES: *C1COC1] | —NH—CH₂— | 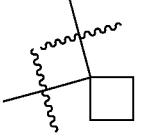 | —(CH₂)₂—O—(CH₂)₂— |
| A-460. | 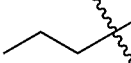 | —NH—CH₂— | 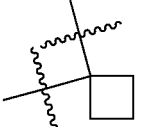 | —(CH₂)₂—O—(CH₂)₂— |
| A-461. | 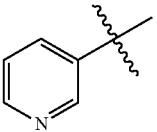 [SMILES: *c1cccnc1] | —NH—CH₂— | 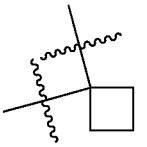 | —(CH₂)₂—O—(CH₂)₂— |
| A-462. | 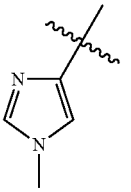 [SMILES: *c1cn(C)cn1] | —NH—CH₂— | 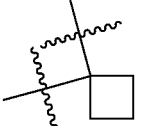 | —(CH₂)₂—O—(CH₂)₂— |
| A-463. | 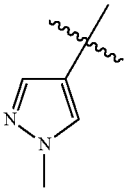 | —NH—CH₂— | 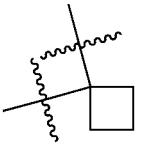 [SMILES: *C1(*)CCC1] | —(CH₂)₂—O—(CH₂)₂— |
| A-464. | 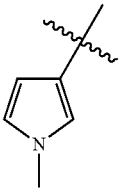 [SMILES: *c1ccn(C)c1] | —NH—CH₂— | 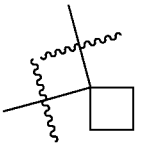 [SMILES: *C1(*)CCC1] | —(CH₂)₂—O—(CH₂)₂— |
| A-465. | 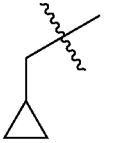 [SMILES: *CC1CC1] | 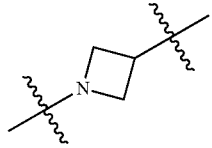 [SMILES: *C1CN(*)C1] | 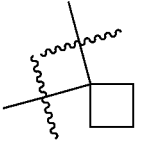 [SMILES: *C1(*)CCC1] | —(CH₂)₂—O—(CH₂)₂— |
| A-466. | 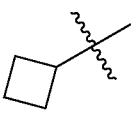 [SMILES: *C1CCC1] | 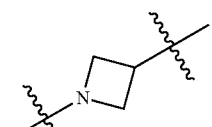 | 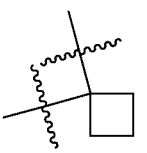 | —(CH₂)₂—O—(CH₂)₂— |
| A-467. | 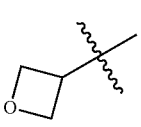 [SMILES: *C1COC1] | 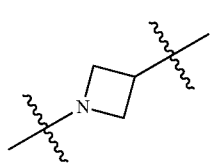 [SMILES: *C1CN(*)C1] | 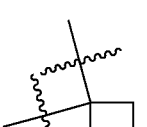 | —(CH₂)₂—O—(CH₂)₂— |

| | R¹ | —Y—A²—X¹— | >CR$^{12a}$R$^{12b}$ | R$^{4a}$, R$^{4b}$ |
|---|---|---|---|---|
| A-468. | propyl/butyl group | azetidine | cyclobutyl linker | —(CH$_2$)$_2$—O—(CH$_2$)$_2$— |
| A-469. | pyridin-3-yl | azetidine | cyclobutyl linker | —(CH$_2$)$_2$—O—(CH$_2$)$_2$— |
| A-470. | 1-methylimidazol-4-yl | azetidine | cyclobutyl linker | —(CH$_2$)$_2$—O—(CH$_2$)$_2$— |
| A-471. | 1-methylpyrazol-4-yl | azetidine | cyclobutyl linker | —(CH$_2$)$_2$—O—(CH$_2$)$_2$— |
| A-472. | 1-methylpyrrol-3-yl | azetidine | cyclobutyl linker | —(CH$_2$)$_2$—O—(CH$_2$)$_2$— |
| A-473. | cyclopropylmethyl | —(CH$_2$)$_2$— | cyclobutyl linker | —(CH$_2$)$_2$—O—(CH$_2$)$_2$— |
| A-474. | cyclobutyl | —(CH$_2$)$_2$— | cyclobutyl linker | —(CH$_2$)$_2$—O—(CH$_2$)$_2$— |
| A-475. | oxetan-3-yl | —(CH$_2$)$_2$— | cyclobutyl linker | —(CH$_2$)$_2$—O—(CH$_2$)$_2$— |
| A-476. | sec-butyl | —(CH$_2$)$_2$— | cyclobutyl linker | —(CH$_2$)$_2$—O—(CH$_2$)$_2$— |

-continued

| R¹ | —Y—A²—X¹— | >CR$^{12a}$R$^{12b}$ | R$^{4a}$, R$^{4b}$ |
|---|---|---|---|
| A-477. ![pyridine] | —(CH$_2$)$_2$— | | —(CH$_2$)$_2$—O—(CH$_2$)$_2$— |
| A-478. ![imidazole] | —(CH$_2$)$_2$— | | —(CH$_2$)$_2$—O—(CH$_2$)$_2$— |
| A-479. ![pyrazole] | —(CH$_2$)$_2$— | | —(CH$_2$)$_2$—O—(CH$_2$)$_2$— |
| A-480. ![pyrrole] | —(CH$_2$)$_2$— | | —(CH$_2$)$_2$—O—(CH$_2$)$_2$— |

Still further particular compounds of the present invention are the phenalkylamine derivatives disclosed in preparation examples in the form of their free bases and in the form of their physiologically tolerated salts thereof. These include for each preparation example the exemplified compound as well as the corresponding free base and any other physiologically tolerated salts of the free base (if the exemplified compound is a salt), or any physiologically tolerated salt of the free base (if the exemplified compound is a free base). These further include enantiomers, diastereomers, tautomers and any other isomeric forms of said compounds, be they explicitly or implicitly disclosed.

The compounds of the formula (I) can be prepared by analogy to methods which are well known in the art. Suitable methods for the preparation of compounds of formula (I) are outlined in the following schemes.

The process depicted in scheme 1 is useful for obtaining phenalkylamines, wherein X¹ is —O— or —S—, and Y¹ is a bond.

Scheme 1:

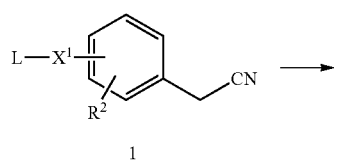

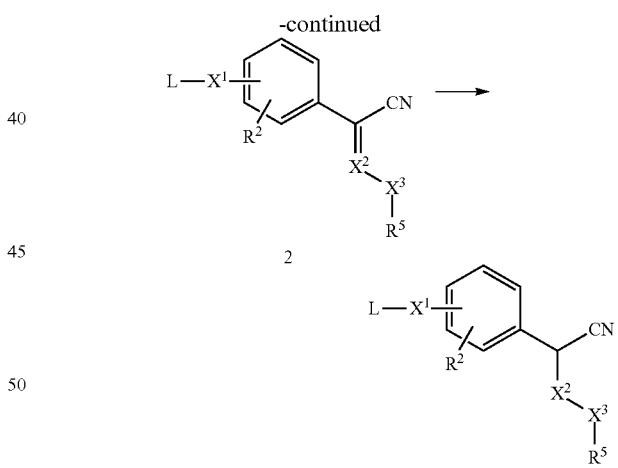

As shown in scheme 1, the compound of general formula 1 readily undergoes condensation with an aldehyde to give the compound of general formula 2. Subsequent hydrogenation (e.g. with NaBH$_4$) affords compound 3. Alternatively compounds of general formula 1 readily undergo alkylation in the presence of a strong base (e.g. LDA=lithium diisopropylamide) to give directly compounds of general formula 3. In this case the benzylic position can carry R³ as additional substituent.

The variables X², X³, R⁵ are as defined herein and L is a suitable protecting group (e.g. L =Me). Compounds 3 can be further converted to compounds of the general formula (I). Alternatively L is a group that represents, or can be converted into, the desired side chain R¹—W-A¹-Q-Y-A²-.

Scheme 2:
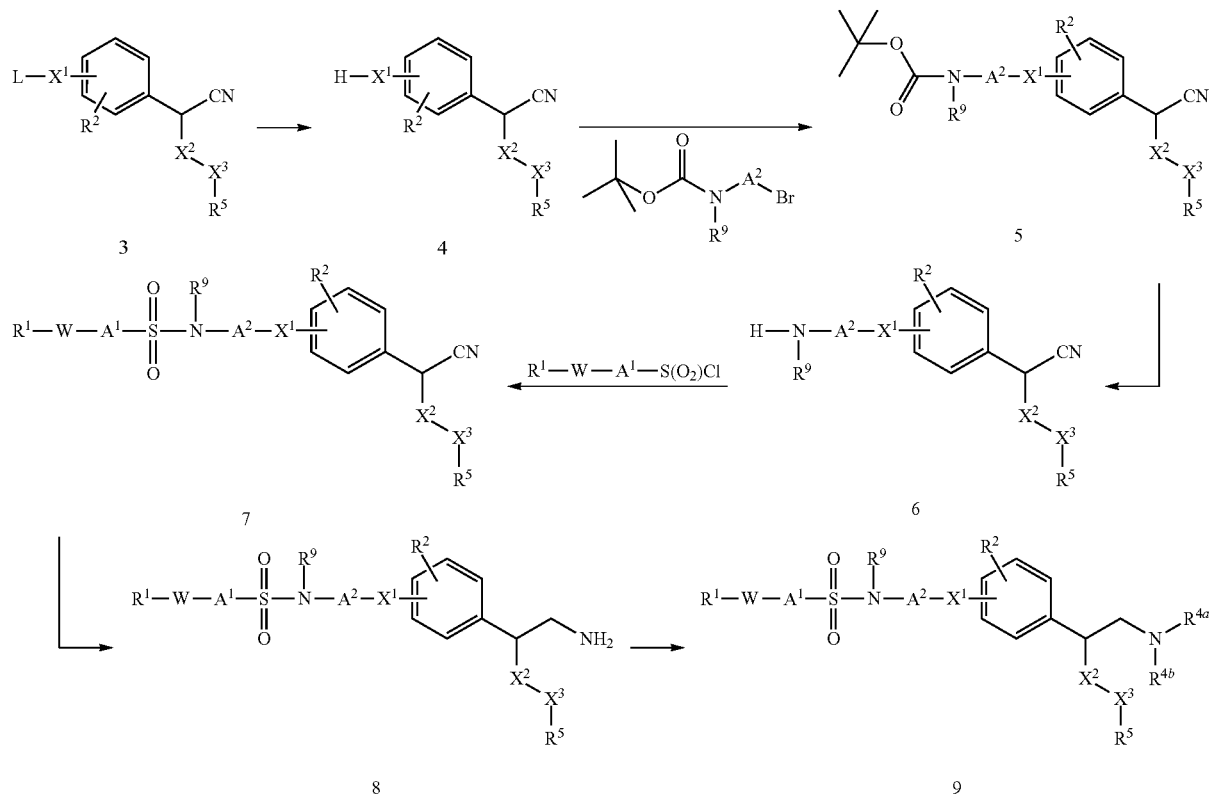
In scheme 2, the variables $R^1$, W, $A^1$, $R^2$, $R^{4a}$, $R^{4b}$, $R^5$, $R^9$, $X^2$, $X^3$ are as defined herein.
The process depicted in scheme 3 is useful for obtaining phenalkylamines, wherein $X^1$ is methylene, $A^2$ is a bond, Y is —$NR^9$—, and Q is —$S(O)_2$.
Scheme 3:
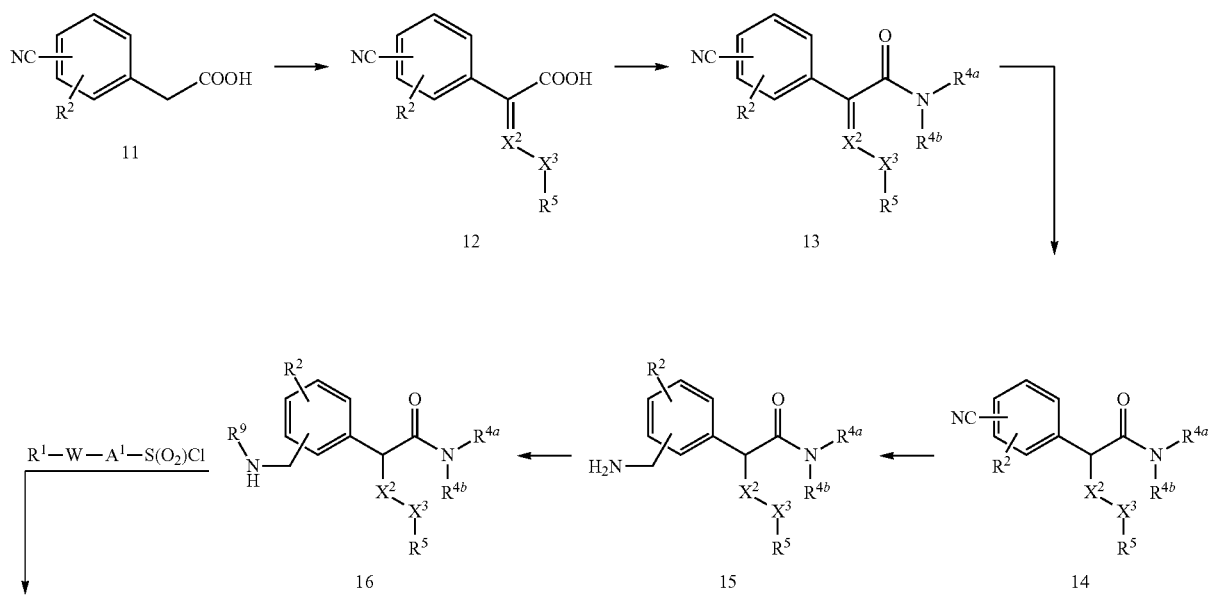

-continued

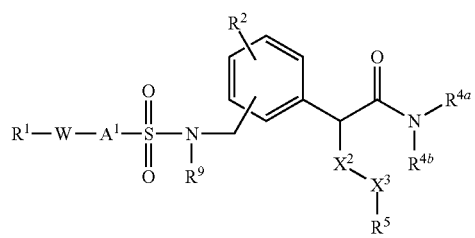

17

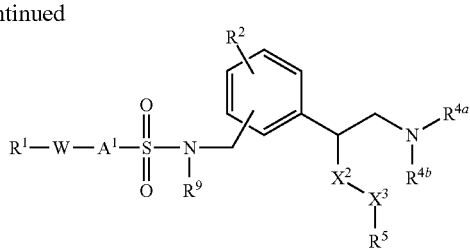

18

In scheme 3, the variables $R^1$, W, $A^1$, $R^2$, $R^{4a}$, $R^{4b}$, $R^5$, $R^9$, $X^2$, $X^3$ are as defined herein.

The process depicted in scheme 4 is useful for obtaining phenalkylamines, wherein $X^1$ is optionally substituted alkylene, $A^2$ is optionally substituted alkylene or a bond, Y is —$NR^9$— and Q is —$S(O)_2$.

Scheme 4:

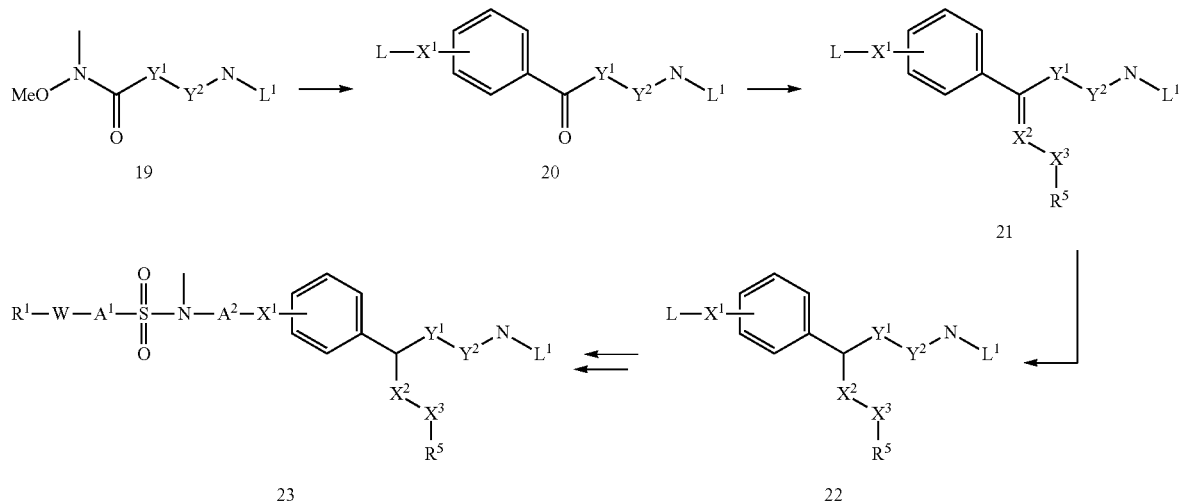

The Weinreb-amide of a suitable protected alpha or beta amino acid (19) undergoes transformation to compound 20 together with a metallo organic reagent (e.g. Grignard reagent). Synthesis of compound 21 could proceed by a Wittig reagent or by a metallo organic reagent (Grignard reagent). Subsequent hydrogenation leads to 22 which is further transformed to the final compound 23 as described in scheme 2 or 3.

In scheme 4, the variables $R^1$, W, $A^1$, $A^2$, $X^1$, $R^2$, $R^{4a}$, $R^{4b}$, $R^5$, $R^9$, $Y^1$, $Y^2$, $X^2$, $X^3$ are as defined herein, and L, $L^1$ are suitable protecting groups.

The process depicted in scheme 5 is useful for obtaining phenalkylamines, wherein $X^1$ is —$NR^{11}$—, $A^2$ is optionally substituted alkylene, Y is —$NR^9$—, and Q is —$S(O)_2$.

Scheme 5:

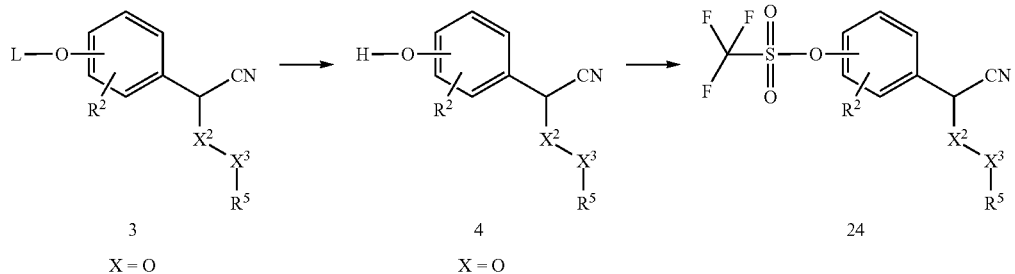

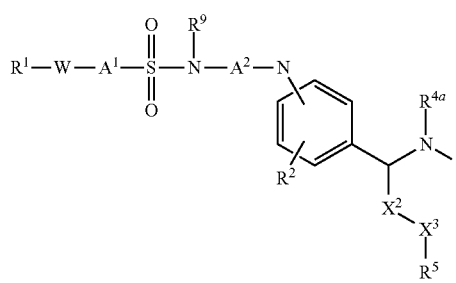

26

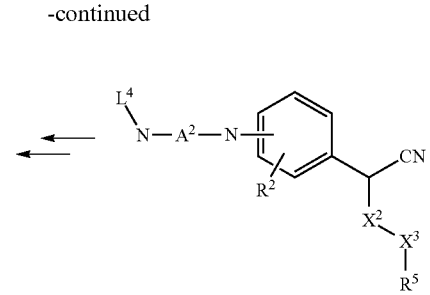

25

In scheme 5, the variables $R^1$, W, $A^1$, $R^2$, $R^{4a}$, $R^{4b}$, $R^5$, $R^9$, $X^2$, $X^3$, $A^2$ are as defined herein, and $L^4$ is a suitable protecting group.

The process depicted in scheme 6 is useful for obtaining phenalkylamines, wherein $R^3$, $R^{4a}$ together are $C_1$-$C_6$ alkylene. It is exemplified for $C_2$ alkylene. Ring closure from compound 28 to 29 might be spontaneous or need to be enforced (e.g. MeMgBr in case of C1 alkylene, see J. Med. Chem. 1968, 466).

Scheme 6

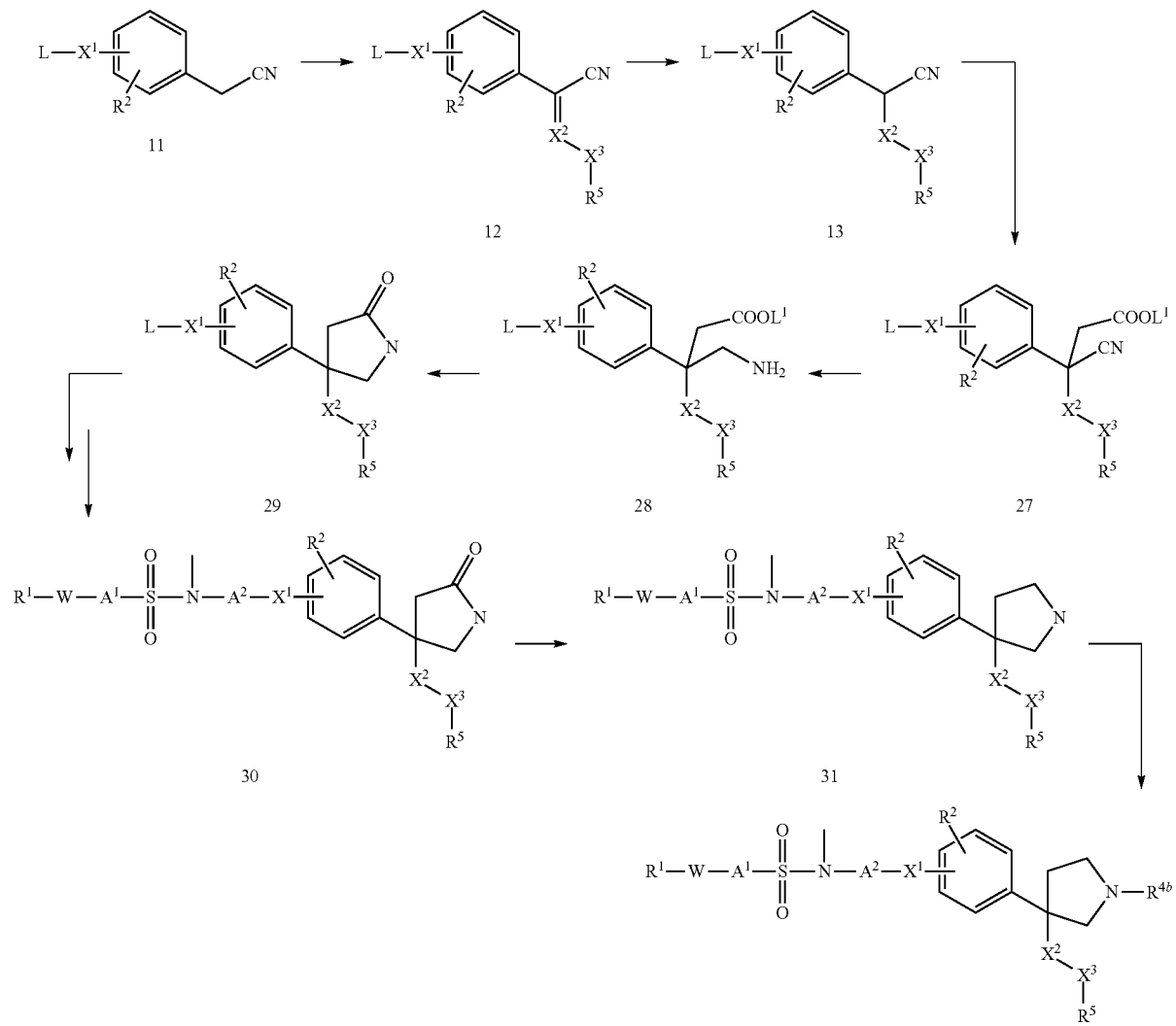

In scheme 6, the variables $R^1$, W, $A^1$, $X^1$, $R^2$, $R^{4a}$, $R^{4b}$, $R^5$, $R^9$, $X^2$, $X^3$, $A^2$ are as defined herein, and L, L' are suitable protecting groups e.g. L, $L^1$=Me.

The process depicted in scheme 7 is useful for obtaining phenalkylamines, wherein $Y^1$, $Y^2$ is a bond.

Suitable amino-protecting groups are well known in the art such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991.

Scheme 7

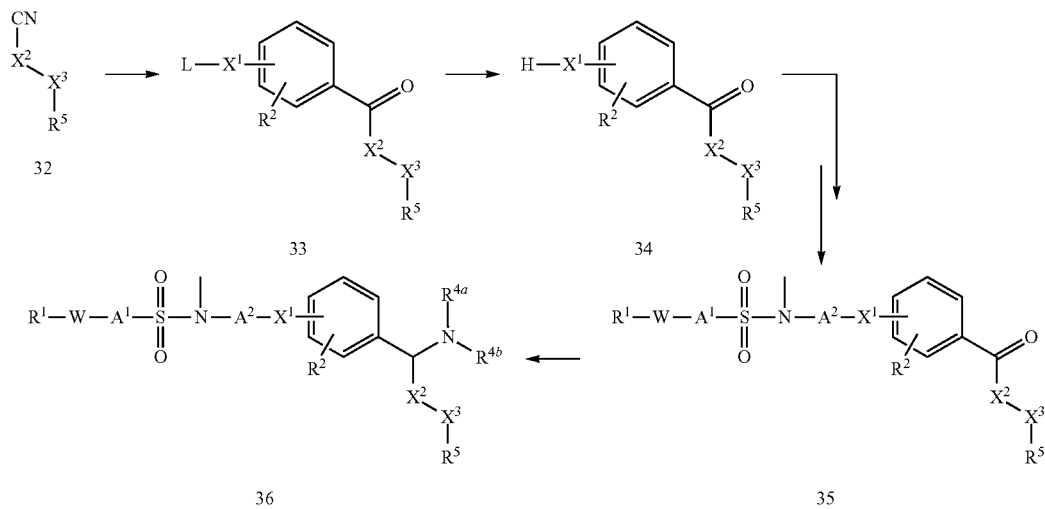

In scheme 7 the variables $R^1$, W, $A^1$, $X^1$, $R^2$, $R^{4a}$, $R^{4b}$, $R^5$, $R^9$, $X^2$, $X^3$, $A^2$ are as defined herein, and L is a suitable protecting group e.g. L=benzyl.

The process depicted in scheme 8 is useful for obtaining phenalkylamines, wherein $X^1$ is —O— or —S—, and Y is a bond.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by Scheme 8:

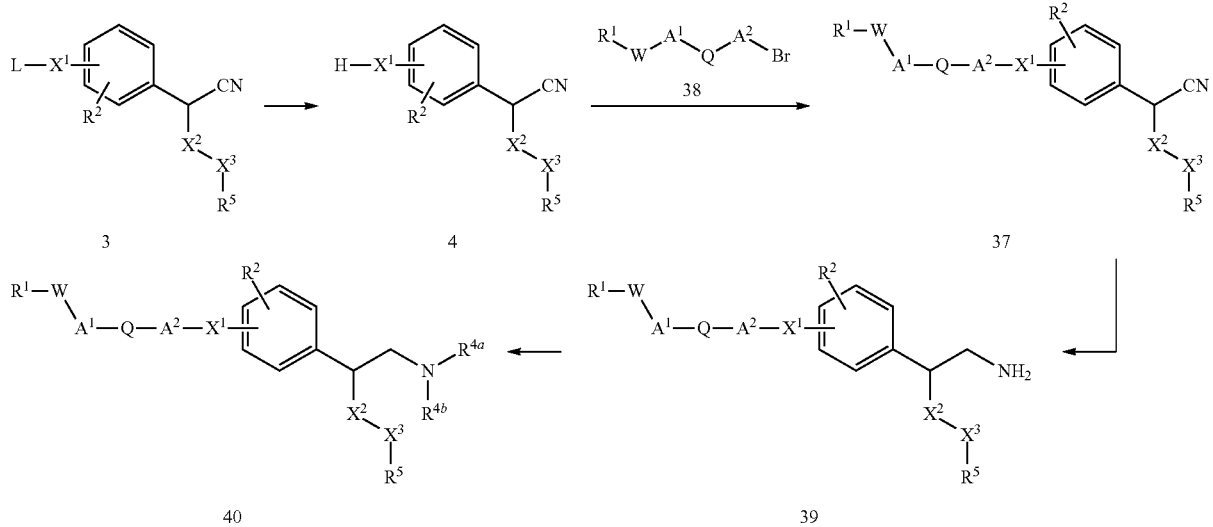

In scheme 8, the variables $R^1$, W, $A^1$, Q, $A^2$, $R^2$, $R^{4a}$, $R^{4b}$, $R^5$, $X^2$, $X^3$ are as defined herein, and L is a suitable protecting group e.g. L=benzyl. One example for compound 38 could be $CH_3$—$SO_2$—$CH_2$—$CH_2$—Br.

Further protocols for the synthesis of compounds in which Y is a bond and W is $NR^8$ are described in WO 2009/121872.

methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}<1$ µMol, more preferably at a level of $IC_{50}<0.5$ µMol, particularly preferably at a level of $IC_{50}<0.2$ µMol and most preferably at a level of $IC_{50}<0.1$ µMol.

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine trans-port may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neurophysiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive suboptimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Cantor-Verlag, 1996.

The compounds of formula (I) may also be suitable for combination with other therapeutic agents.

Thus, the present invention also provides:

i) a combination comprising a compound of formula (I) with one or more further therapeutic agents;
ii) a pharmaceutical composition comprising a combination product as defined in i) above and at least one carrier, diluent or excipient;
iii) the use of a combination as defined in i) above in the manufacture of a medicament for treating or preventing a disorder, disease or condition as defined herein;
iv) a combination as defined in i) above for use in treating or preventing a disorder, disease or condition as defined herein;
v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration,
vi) a combination as defined in i) above for use in therapy;
vii) a method of treatment or prevention of a disorder, disease or condition as defined herein comprising administering an effective amount of a combination as defined in i) above;
viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilised on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilising or antimanic agent, a pharmaceutical composition comprising compounds of formula (I) and at least one mood stabilising or antimanic agent, the use of a pharmaceutical composition comprising compounds of formula (I) and at least one mood stabilising or antimanic agent in the manufacture of a medicament for the treatment of a psychotic disorder, and a pharmaceutical composition comprising compounds of formula (I) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benziso-thiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE (D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRI N®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, anti-depressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1 B antagonists, 5HT1 D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLC-MS in a fast gradient on C18-material (electrospray-ionisation (ESI) mode).

PREPARATION EXAMPLES

Example 1

1-Methyl-1H-imidazole-4-sulfonic acid {2-[3-(2-amino-1-benzyl-ethyl)-4-fluorophenoxy]-ethyl}-amide hydrochloride

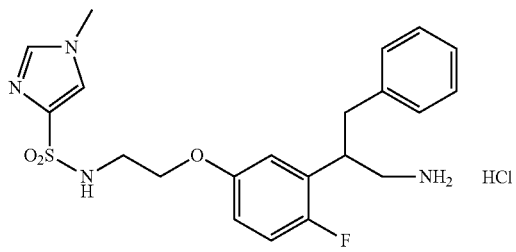 [SMILES: Cn1cnc(S(=O)(=O)NCCOc2ccc(F)c(C(CN)Cc3ccccc3)c2)c1 ; Cl]

1.1 2-(2-Fluoro-5-methoxy-phenyl)-3-phenyl-acrylonitrile

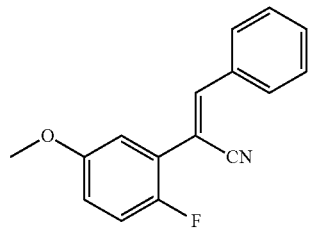 [SMILES: COc1ccc(F)c(/C(C#N)=C/c2ccccc2)c1]

To a solution of 5-methoxy-2-fluorobenzylcyanide (8 g, 48.4 mmol) in 200 ml ethanol was added sodium ethoxide 21% in ethanol (19.89 ml, 53.3 mmol) and benzaldehyde (4.92 ml, 48.4 mmol). The reaction mixture was stirred at room temperature over night and concentrated to ½ volume, filtered and washed with small amount of ether, and dried under high vacuum to obtain yellow crystals.

1.2 2-(2-Fluoro-5-methoxy-phenyl)-3-phenyl-propionitrile

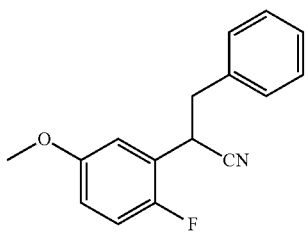 [SMILES: COc1ccc(F)c(C(C#N)Cc2ccccc2)c1]

To a suspension of 2-(2-fluoro-5-methoxy-phenyl)-3-phenyl-acrylonitrile (5.8 g, 22.90 mmol) in ethanol was added sodium borohydride (1.083 g, 28.6 mmol) and stirred at room temperature over night. The mixture was poured on ice-water and after addition of 5% citric acid extracted with ethyl acetate. The combined organic layers were washed with brine, dried over sodium sulfate, filtered and concentrated to obtain an orange oil m=5.68 g (97%).

1.3 2-(2-Fluoro-5-hydroxy-phenyl)-3-phenyl-propionitrile

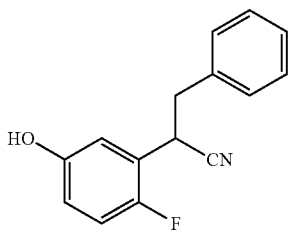 [SMILES: N#CC(Cc1ccccc1)c1cc(O)ccc1F]

To a stirred and cooled (0° C.) solution of 2-(2-fluoro-5-methoxy-phenyl)-3-phenyl-propionitrile (5.68 g, 22.25 mmol) in 150 ml dichloromethane under argon was added dropwise a 1M solution of boron tribromide in dichloromethane (66.7 ml, 66.7 mmol). The reaction was allowed to warm up to room temperature. The mixture was stirred over night, poured on ice water, diluted with dichloromethane. The organic layer was separated and the aqueous layer extracted twice with dichloromethane. The combined organic layers were washed subsequently with water, saturated sodium bicarbonate solution and brine, then dried over sodium sulphate and filtered. Evaporation of solvent afforded a pale brown solid.

1.4 {2-[3-(Benzyl-cyano-methyl)-4-fluoro-phenoxy]-ethyl}-carbamic acid tert-butyl ester

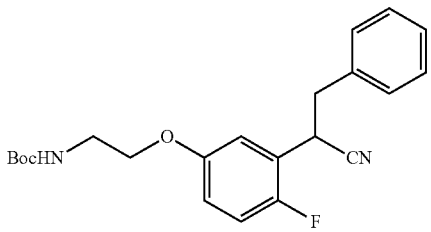 [SMILES: CC(C)(C)OC(=O)NCCOc1ccc(F)c(C(C#N)Cc2ccccc2)c1]

A suspension of 2-(2-fluoro-5-hydroxy-phenyl)-3-phenyl-propionitrile (4.39 g, 18.20 mmol) and cesium carbonate (11.86 g, 36.4 mmol) in acetonitrile was stirred at 80° C. under argon for 1 h, then cooled down to 50° C. and tert-butyl 2-bromoethylcarbamate (8.16 g, 36.4 mmol), dissolved in 10 ml acetonitrile was added. The resulting mixture was stirred at 80° C. for 2 h. The solvent was evaporated and concentrated to obtain the desired crude product as an orange oil.

1.5. 2-[5-(2-Amino-ethoxy)-2-fluoro-phenyl]-3-phenyl-propionitrile

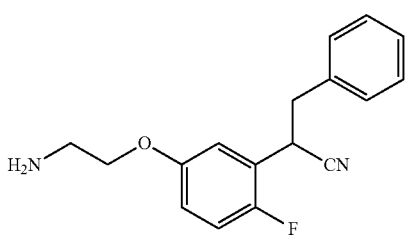 [SMILES: N#CC(Cc1ccccc1)c1cc(OCCN)ccc1F]

To {2-[3-(benzyl-cyano-methyl)-4-fluoro-phenoxy]-ethyl}-carbamic acid tert-butyl ester (7 g, 18.21 mmol) was added 25 ml of a 4 N hydrochloric acid solution in dioxane and stirred at room temperature over night. Solvents were evaporated, 2 N sodium hydroxide was added, which was extracted twice with dichloromethane. The organic layer was dried over sodium sulfate, filtered and concentrated to obtain the free amine as a brown oil.

1.6. 1-Methyl-1H-imidazole-4-sulfonic acid {2-[3-(benzyl-cyano-methyl)-4-fluorophenoxy]-ethyl}-amide

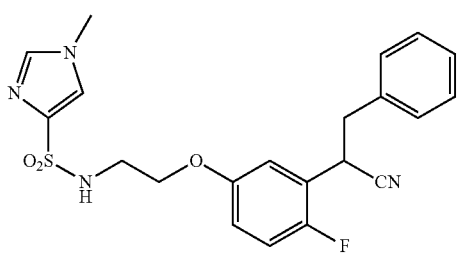 [SMILES: Cn1cnc(S(=O)(=O)NCCOc2ccc(F)c(C(C#N)Cc3ccccc3)c2)c1]

To a stirred solution of 2-[5-(2-amino-ethoxy)-2-fluoro-phenyl]-3-phenyl-propionitrile (536 mg, 1.885 mmol) in dry dichloromethane was added 4-dimethylaminopyridine (345 mg, 2.83 mmol) followed by 1-methyl-1H-imidazole-4-sulfonyl chloride (409 mg, 2.262 mmol). The mixture was stirred at RT under argon over night. Dichloromethane was added and the mixture was subsequently washed twice with 1N hydrochloric acid, water, sodium bicarbonate solution, brine and then dried over sodium sulfate, filtered and concentrated to obtain the desired product as a pale yellow solid.

1.7 1-Methyl-1H-imidazole-4-sulfonic acid {2-[3-(2-amino-1-benzyl-ethyl)-4-fluorophenoxy]-ethyl}-amide hydrochloride

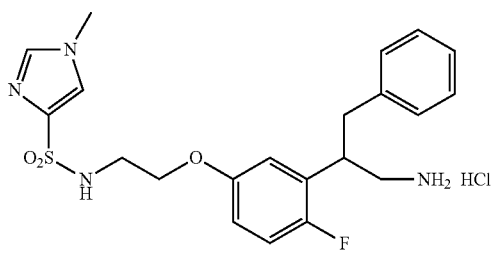 [SMILES: Cn1cnc(S(=O)(=O)NCCOc2ccc(F)c(C(CN)Cc3ccccc3)c2)c1 ; Cl]

A 1M solution of diisobutylaluminium hydride (3.53 ml, 3.53 mmol) in toluene was added dropwise to a solution of 1-methyl-1H-imidazole-4-sulfonic acid {2-[3-(benzyl-cyanomethyl)-4-fluoro-phenoxy]-ethyl}-amide (721 mg, 1.683 mmol) in 4 ml dichloromethane at 0° C. The reaction was stirred at this temperature for 30 min and then added to a suspension of sodium borohydride (2546 mg, 67.3 mmol) in 5 ml tetrahydrofuran/methanol (1:3) at 0° C., stirred for 1 h allowing to warm up to room temperature. 1 N sodium hydroxide solution was added and the mixture was extracted three times with dichloromethane. The combined organic layers were washed with water and brine, dried over sodium sulfate, filtered and evaporated to obtain the free amine as a white solid which was purified by flash chromatography on $SiO_2$ cartridge (10% methanol in dichloromethane) to obtain 285 mg (36%) product as a colourless solid.

ESI-MS [M+H$^+$]=433 Calculated for $C_{21}H_{25}FN_4O_3S$=432

30 mg were converted to the hydrochloride by adding 2 ml of a 1 N hydrochloric acid solution in ether. The reaction mixture was stirred at room temperature over night, filtered and washed with small amount of ether to obtain pale yellow crystals m=13.9 mg.

The following compounds were prepared in analogy to Example 1:

Example 2

1-Methyl-1H-pyrazole-4-sulfonic acid (2-{3-[2-amino-1-(3-chloro-benzyl)ethyl]-phenoxy}-ethyl)-amide, hydrochloride

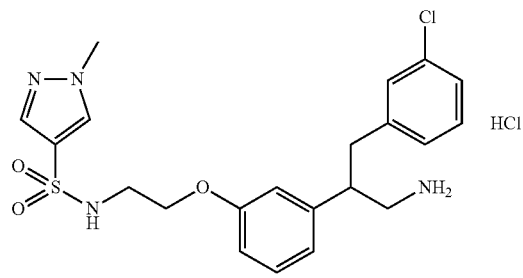 [SMILES: Cn1cc(S(=O)(=O)NCCOc2cccc(C(CN)Cc3cccc(Cl)c3)c2)cn1 ; Cl]

ESI-MS [M+H$^+$]=449 Calculated for $C_{21}H_{25}ClN_4O_3S$=448

Example 3

1-Methyl-1H-pyrazole-4-sulfonic acid {2-[5-(2-amino-1-benzyl-ethyl)-2-fluorophenoxy]-ethyl}-amide, hydrochloride

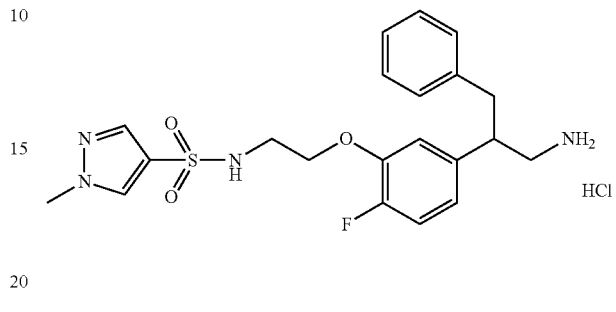

ESI-MS [M+H$^+$]=433 Calculated for $C_{21}H_{25}FN_4O_3S$=432

Example 4

1-Methyl-1H-imidazole-4-sulfonic acid {2-[5-(2-amino-1-benzyl-ethyl)-2-fluorophenoxy]-ethyl}-amide, hydrochloride

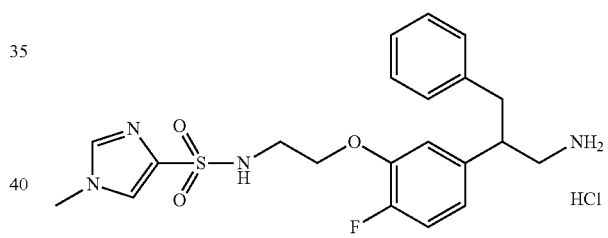

ESI-MS [M+H$^+$]=433 Calculated for $C_{21}H_{25}FN_4O_3S$=432

Example 5

1-Methyl-1H-imidazole-4-sulfonic acid {2-[3-(2-amino-1-benzyl-ethyl)phenoxy]-ethyl}-amide

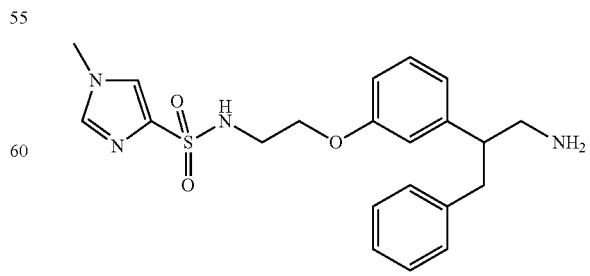

ESI-MS [M+H$^+$]=415 Calculated for $C_{21}H_{26}N_4O_3S$=414

Example 6

1-Methyl-1H-pyrazole-4-sulfonic acid {2-[3-(2-amino-1-benzyl-ethyl)-phenoxy]-ethyl}-amide, hydrochloride

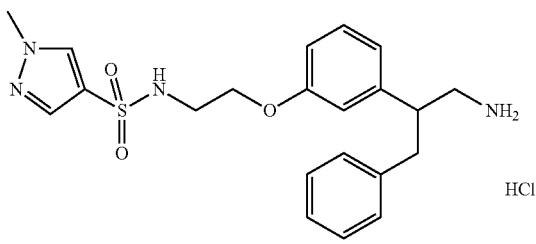 [SMILES: Cn1cc(S(=O)(=O)NCCOc2cccc(C(CN)Cc3ccccc3)c2)cn1 ; Cl]

ESI-MS [M+H$^+$]=415 Calculated for $C_{21}H_{26}N_4O_3S$=414

Example 7

1-Methyl-1H-pyrazole-4-sulfonic acid (2-{3-[2-amino-1-(3,5-difluoro-benzyl)ethyl]-phenoxy}-ethyl)-amide, hydrochloride

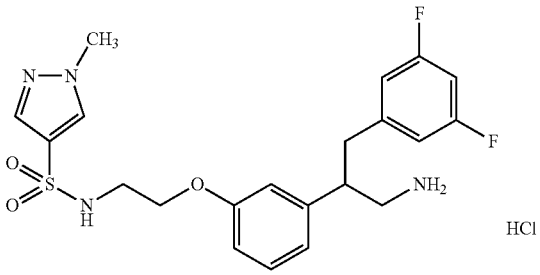 [SMILES: Cn1cc(S(=O)(=O)NCCOc2cccc(C(CN)Cc3cc(F)cc(F)c3)c2)cn1 ; Cl]

7.1 1-Methyl-1H-pyrazole-4-sulfonic acid [2-(3-cyanomethyl-phenoxy)-ethyl]-amide

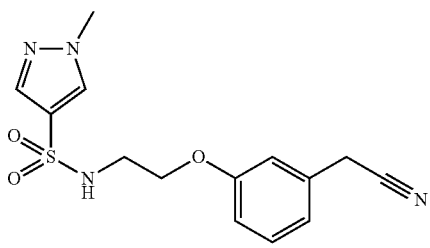 [SMILES: Cn1cc(S(=O)(=O)NCCOc2cccc(CC#N)c2)cn1]

1-Methyl-1H-pyrazole-4-sulfonic acid [2-(3-cyanomethyl-phenoxy)-ethyl]amide was prepared from 2-(3-methoxy-phenyl)-3-phenyl-propionitrile in analogy to example 1 by following steps 1.3-1.6.

7.2 1-Methyl-1H-pyrazole-4-sulfonic acid (2-{3-[2-amino-1-(3,5-difluoro-benzyl)-ethyl]-phenoxy}-ethyl)-amide, hydrochloride

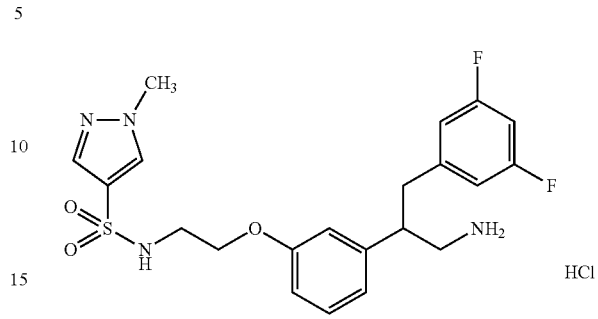

1-Methyl-1H-pyrazole-4-sulfonic acid (2-{3-[2-amino-1-(3,5-difluoro-benzyl)-ethyl]-phenoxy}-ethyl)-amide was prepared from 1-methyl-1H-pyrazole-4-sulfonic acid [2-(3-cyanomethyl-phenoxy)-ethyl]-amide in analogy to example 1 following the steps 1.1, 1.2 and 1.7.

ESI-MS [M+H$^+$]=451 Calculated for $C_{21}H_{24}F_2N_4O_3S$=450

The following compounds were prepared in analogy to Example 7:

Example 8

1-Methyl-1H-pyrazole-4-sulfonic acid (2-{3-[2-amino-1-(4-chloro-benzyl)ethyl]-phenoxy}-ethyl)-amide, hydrochloride

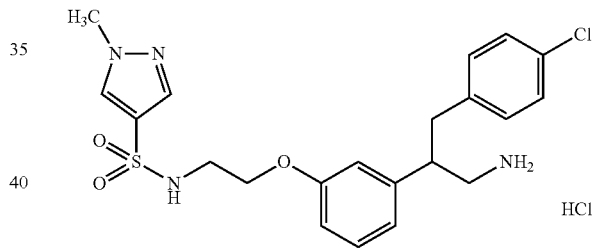

ESI-MS [M+H$^+$]=449 Calculated for $C_{21}H_{25}ClN_4O_3S$=448

Example 9

1-Methyl-1H-imidazole-4-sulfonic acid (2-{3-[2-amino-1-(3-chloro-benzyl)ethyl]-phenoxy}-ethyl)-amide, hydrochloride

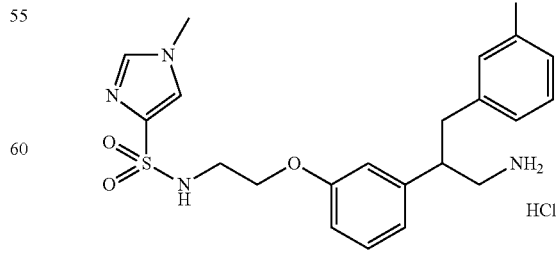

ESI-MS [M+H$^+$]=449 Calculated for $C_{21}H_{25}ClN_4O_3S$=448

Example 10

1-Methyl-1H-pyrazole-4-sulfonic acid (2-{3-[2-amino-1-(3-trifluoromethylbenzyl)-ethyl]-phenoxy}-ethyl)-amide, hydrochloride

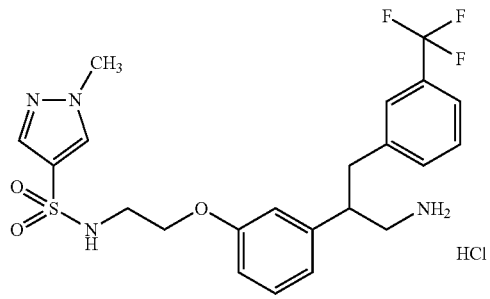 [SMILES: Cn1cc(S(=O)(=O)NCCOc2cccc(C(CN)Cc3cccc(C(F)(F)F)c3)c2)cn1 ; Cl]

ESI-MS [M+H⁺]=483 Calculated for $C_{22}H_{25}F_3N_4O_3S$=482

Example 11

1-Methyl-1H-imidazole-4-sulfonic acid (2-{3-[2-amino-1-(3,5-difluoro-benzyl)ethyl]-phenoxy}-ethyl)-amide, hydrochloride

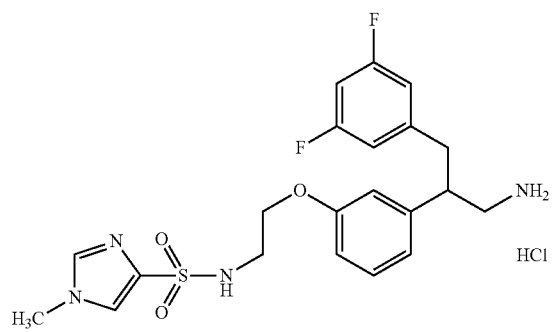 [SMILES: Cn1cnc(S(=O)(=O)NCCOc2cccc(C(CN)Cc3cc(F)cc(F)c3)c2)c1 ; Cl]

ESI-MS [M+H⁺]=451 Calculated for $C_{21}H_{24}F_2N_4O_3S$=450

Example 12

1-Methyl-1H-imidazole-4-sulfonic acid (2-{3-[2-amino-1-(3-trifluoromethylbenzyl)-ethyl]-phenoxy}-ethyl)-amide, hydrochloride

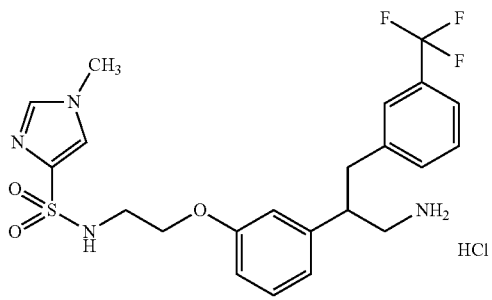 [SMILES: Cn1cnc(S(=O)(=O)NCCOc2cccc(C(CN)Cc3cccc(C(F)(F)F)c3)c2)c1 ; Cl]

ESI-MS [M+H⁺]=483 Calculated for $C_{22}H_{25}F_3N_4O_3S$=482

Example 13

2-[3-(Cyclopropylmethanesulfonylamino-methyl)-phenyl]-3-phenyl-propionamide

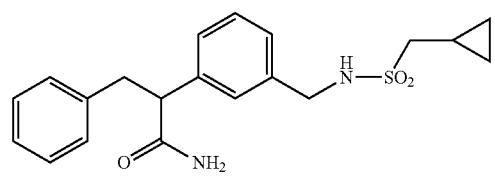 [SMILES: NC(=O)C(Cc1ccccc1)c1cccc(CNS(=O)(=O)CC2CC2)c1]

13.1: 2-(3-Cyano-phenyl)-3-phenyl-acrylic acid

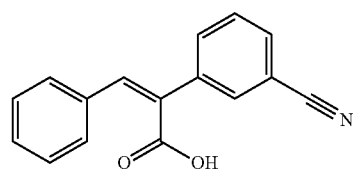 [SMILES: N#Cc1cccc(/C(=C/c2ccccc2)C(=O)O)c1]

(3-Cyano-phenyl)-acetic acid (3.0 g, 18.62 mmol) was dissolved in 2 ml acetic anhydride. 1.1 eq Benzaldehyde and 1.3 eq pyridine were added and heated to 150° C. for 1 h (red solution). The mixture was cooled down to room temperature and 4 ml HCl (37%) were added. The formed precipitate was dissolved with 350 ml CH₂Cl₂ and washed successively with water and 0.5 N NaOH. To the combined NaOH layers was added 1 N HCl (pH=2) and extracted with methylene chloride. The organic layer was dried, filtered and evaporated. Chromatography on 12 g SiO₂ using 5-10% methanol in methylene chloride afforded the desired product m=1.75 g (37%).

13.2 2-(3-Cyano-phenyl)-3-phenyl-acrylamide

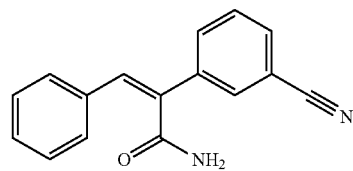 [SMILES: N#Cc1cccc(/C(=C/c2ccccc2)C(N)=O)c1]

2-(3-Cyano-phenyl)-3-phenyl-acrylic acid (386 mg, 1.54 mmol) was dissolved in 15 ml methylene chloride. DMAP (95 mg, 0.8 mmol) and HATU (765 mg, 2 mmol) were added and the resulting mixture stirred for 30 min. Then NH₃ solution (7.7 ml, 2 M in dioxane) was added and stirred until LCMS showed completion. The reaction was diluted with methylene chloride and washed subsequently with water, 1 N HCl, brine and NaHCO₃. The organic layer was dried, filtered and evaporated. Chromatography on 12 g SiO$_2$ using 35% heptane in ethylacetate afforded the desired product m=243.2 mg (63%).

13.3 2-(3-Cyano-phenyl)-3-phenyl-propionamide

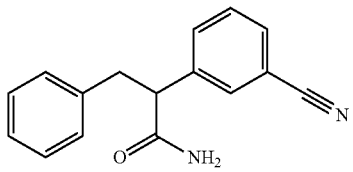 [SMILES: N#Cc1cccc(C(Cc2ccccc2)C(N)=O)c1]

2-(3-Cyano-phenyl)-3-phenyl-acrylamide (243 mg, 0.98 mmol) was dissolved in 20 ml methanol. 20 mg 10% Pd/C were added. Hydrogenation occurred over night. The mixture was filtered and the solvent evaporated to obtain the desired product m=218 mg (89%).

13.4 2-(3-Aminomethyl-phenyl)-3-phenyl-propionamide

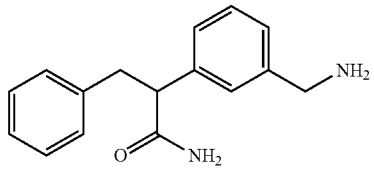 [SMILES: NCc1cccc(C(Cc2ccccc2)C(N)=O)c1]

2-(3-Cyano-phenyl)-3-phenyl-propionamide (218 mg, 0.87 mmol) was dissolved in 5 ml THF. NH$_3$/methanol solution (7 M) was added followed by ~100 mg Raney-Nickel (2400 mesh/water). Hydrogenation occurred over night after which the mixture was filtered and the solvent evaporated. The residue was dissolved in methylene chloride and washed with NaHCO$_3$ solution. The aqueous layer was further treated with NaOH (2 M) and extracted with methylene chloride. The organic layer was dried, filtered and the solvent evaporated to obtain the desired product m=62.6 mg (28.3%).

13.5 2-[3-(Cyclopropylmethanesulfonylamino-methyl)-phenyl]-3-phenyl-propionamide

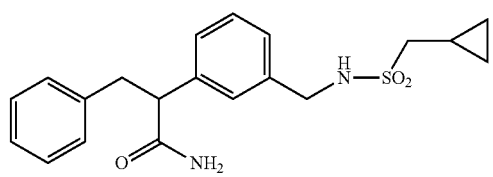

Compound was prepared from 2-(3-aminomethyl-phenyl)-3-phenyl-propionamide in analogy to example 1/step 1.6.

ESI-MS [M+H$^+$]=373 Calculated for C$_{20}$H$_{24}$N$_2$O$_3$S=372

Example 14

N-[3-(2-Amino-1-benzyl-ethyl)-benzyl]-C-cyclopropyl-methanesulfonamide

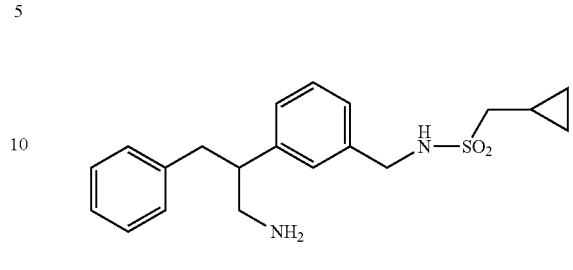

2-[3-(Cyclopropylmethanesulfonylamino-methyl)-phenyl]-3-phenyl-propionamide (72 mg, 0.193 mmol) dissolved in 10 ml THF was treated with 1 M BH$_3$*THF (1.9 ml, 1.9 mmol) and stirred for 2 h. Then 0.3 ml of a 20% HCl-solution and 0.85 ml methanol was added and stirred for 20 min. Solvent was evaporated and the residue treated with 1 N NaOH. Product was extracted with ethyl acetate, dried, filtered and the solvent evaporated. Formation of the HCl-salt (4 N HCl/dioxane) in diisopropyl ether/methylene chloride afforded 61 mg product (80%) as a white solid.

ESI-MS [M+H$^+$]=359 Calculated for C$_{20}$H$_{26}$N$_2$O$_2$S=358

The following compounds were prepared in analogy to Example 13:

Example 15

2-{3-[(1-Methyl-1H-pyrazole-4-sulfonylamino)-methyl]-phenyl}-3-phenyl-propionamide

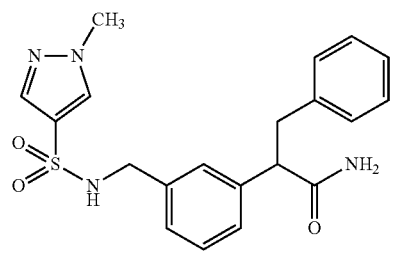 [SMILES: Cn1cc(S(=O)(=O)NCc2cccc(C(Cc3ccccc3)C(N)=O)c2)cn1]

ESI-MS [M+H$^+$]=399 Calculated for C$_{20}$H$_{22}$N$_4$O$_3$S=398

Example 16

2-{3-[(1-Methyl-1H-imidazole-4-sulfonylamino)-methyl]-phenyl}-3-phenyl-propionamide

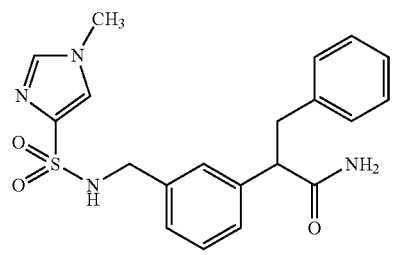 [SMILES: Cn1cnc(S(=O)(=O)NCc2cccc(C(Cc3ccccc3)C(N)=O)c2)c1]

ESI-MS [M+H$^+$]=399 Calculated for C$_{20}$H$_{22}$N$_4$O$_3$S=398

Example 17

1-Methyl-1H-imidazole-4-sulfonic acid 3-(1-benzyl-2-morpholin-4-yl-2-oxoethyl)-benzylamide

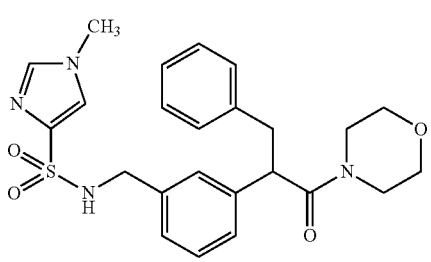 [SMILES: Cn1cnc(S(=O)(=O)NCc2cccc(C(Cc3ccccc3)C(=O)N3CCOCC3)c2)c1]

ESI-MS [M+H$^+$]=469 Calculated for $C_{24}H_{28}N_4O_4S$=468

The following compounds were prepared in analogy to Example 14:

Example 18

1-Methyl-1H-pyrazole-4-sulfonic acid 3-(2-amino-1-benzyl-ethyl)benzylamide, hydrochloride

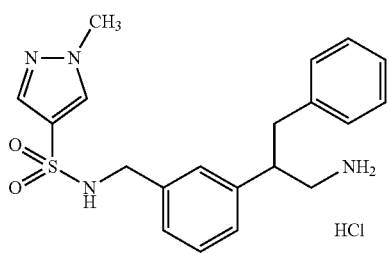 [SMILES: Cn1cc(S(=O)(=O)NCc2cccc(C(CN)Cc3ccccc3)c2)cn1 ; Cl]

ESI-MS [M+H$^+$]=385 Calculated for $C_{20}H_{24}N_4O_2S$=384

Example 19

1-Methyl-1H-imidazole-4-sulfonic acid 3-(2-amino-1-benzyl-ethyl)benzylamide, hydrochloride

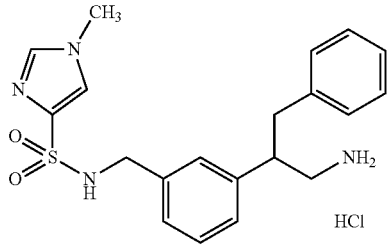 [SMILES: Cn1cnc(S(=O)(=O)NCc2cccc(C(CN)Cc3ccccc3)c2)c1 ; Cl]

ESI-MS [M+H$^+$]=385 Calculated for $C_{20}H_{24}N_4O_2S$=384

Example 20

1-Methyl-1H-imidazole-4-sulfonic acid 3-(1-benzyl-2-morpholin-4-yl-ethyl)benzylamide

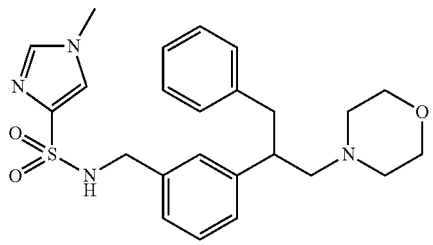 [SMILES: Cn1cnc(S(=O)(=O)NCc2cccc(C(Cc3ccccc3)CN3CCOCC3)c2)c1]

ESI-MS [M+H$^+$]=455 Calculated for $C_{24}H_{30}N_4O_3S$=454

Example 21

1-Methyl-1H-pyrazole-4-sulfonic acid 3-(1-benzyl-2-morpholin-4-yl-ethyl)benzylamide

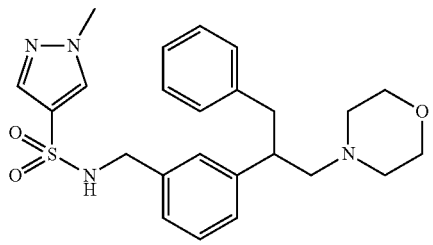 [SMILES: Cn1cc(S(=O)(=O)NCc2cccc(C(Cc3ccccc3)CN3CCOCC3)c2)cn1]

ESI-MS [M+H$^+$]=455 Calculated for $C_{24}H_{30}N_4O_3S$=454

Example 22

N-[3-(1-Benzyl-2-morpholin-4-yl-ethyl)-benzyl]-C-cyclopropyl-methanesulfonamide, hydrochloride

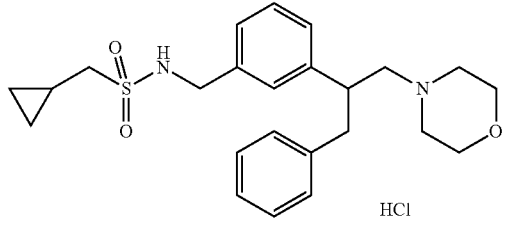 [SMILES: O=S(=O)(CC1CC1)NCc1cccc(C(Cc2ccccc2)CN2CCOCC2)c1 ; Cl]

ESI-MS [M+H$^+$]=429 Calculated for $C_{24}H_{32}N_2O_3S$=428

Example 23

1-Methyl-1H-imidazole-4-sulfonic acid {2-[3-(1-benzyl-2-dimethylaminoethyl)-4-fluoro-phenoxy]-ethyl}-amide

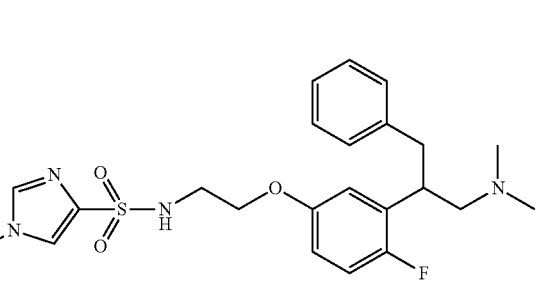

A mixture of 1-methyl-1H-imidazole-4-sulfonic acid {2-[3-(2-amino-1-benzyl-ethyl)-4-fluorophenoxy]-ethyl}-amide (example 1, 49.7 mg, 0.115 mmol) and formaldehyde (37% in water, 0.086 ml, 1.149 mmol) in methanol was stirred at room temperature for 10 min. Sodium cyanoborohydride (14.4 mg, 0.230 mmol) was added and the resulting mixture was stirred at room temperature for 2 h. Most of the solvent was evaporated and the slurry was diluted in ethyl acetate, washed with a mixture of sodium bicarbonate and 50% brine. The organic layers were dried, filtered and concentrated to obtain a clear solid which was purified on 4 g $SiO_2$ using 10% methanol in dichloromethane affording 26.7 mg (50%) of a clear oil.

ESI-MS [M+H$^+$]=461 Calculated for $C_{23}H_{29}FN_4O_3S$=460

The following compounds were prepared in analogy to Example 23:

Example 24

1-Methyl-1H-pyrazole-4-sulfonic acid {2-[3-(1-benzyl-2-dimethylamino-ethyl)-phenoxy]-ethyl}-amide

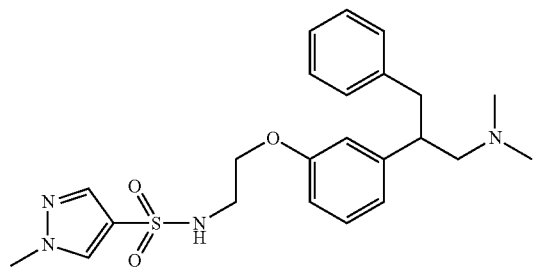

ESI-MS [M+H$^+$]=443 Calculated for $C_{23}H_{30}N_4O_3S$=442

Example 25

1-Methyl-1H-imidazole-4-sulfonic acid {2-[3-(1-benzyl-2-dimethylaminoethyl)-phenoxy]-ethyl}-amide

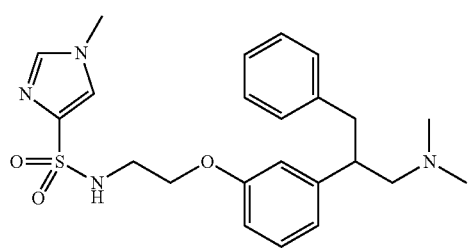 [SMILES: CN(C)CC(Cc1ccccc1)c1cccc(OCCNS(=O)(=O)c2cn(C)cn2)c1]

ESI-MS [M+H$^+$]=443 Calculated for $C_{23}H_{30}N_4O_3S$=442

Example 26

1-Methyl-1H-imidazole-4-sulfonic acid 3-(1-benzyl-2-dimethylamino-ethyl)benzylamide

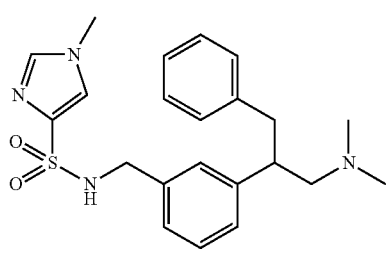 [SMILES: CN(C)CC(Cc1ccccc1)c1cccc(CNS(=O)(=O)c2cn(C)cn2)c1]

ESI-MS [M+H$^+$]=413 Calculated for $C_{22}H_{28}N_4O_2S$=412

Example 27

1-Methyl-1H-pyrazole-4-sulfonic acid 3-(1-benzyl-2-dimethylamino-ethyl)benzylamide

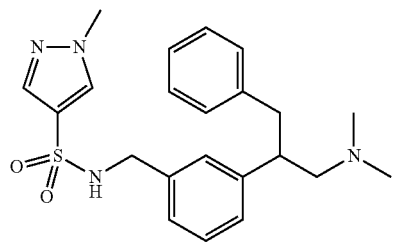 [SMILES: CN(C)CC(Cc1ccccc1)c1cccc(CNS(=O)(=O)c2cnn(C)c2)c1]

ESI-MS [M+H$^+$]=413 Calculated for $C_{22}H_{28}N_4O_2S$=412

Example 28

1-Methyl-1H-pyrazole-4-sulfonic acid (2-{3-[2-dimethylamino-1-(3-trifluoromethyl-benzyl)-ethyl]-phenoxy}-ethyl)-amide

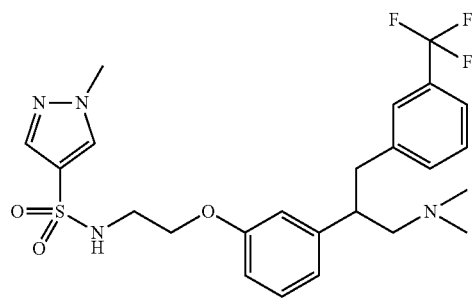 [SMILES: CN(C)CC(Cc1cccc(C(F)(F)F)c1)c1cccc(OCCNS(=O)(=O)c2cnn(C)c2)c1]

ESI-MS [M+H$^+$]=511 Calculated for $C_{24}H_{29}F_3N_4O_3S$=510

Example 29

1-Methyl-1H-imidazole-4-sulfonic acid (2-{3-[2-dimethylamino-1-(3-trifluoromethyl-benzyl)-ethyl]-phenoxy}-ethyl)-amide

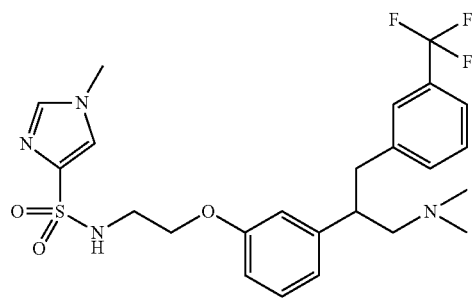 [SMILES: CN(C)CC(Cc1cccc(C(F)(F)F)c1)c1cccc(OCCNS(=O)(=O)c2cn(C)cn2)c1]

ESI-MS [M+H$^+$]=511 Calculated for $C_{24}H_{29}F_3N_4O_3S$=510

Example 30

1-Methyl-1H-pyrazole-4-sulfonic acid {2-[3-(1-benzyl-2-dimethylamino-ethyl)-4-chloro-phenoxy]-ethyl}-amide, hydrochloride

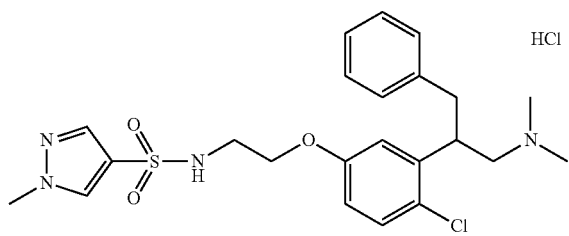

ESI-MS [M+H$^+$]=477 Calculated for C$_{23}$H$_{29}$ClN$_4$O$_3$S=476

Example 31

1-Methyl-1H-pyrazole-4-sulfonic acid {2-[5-(1-benzyl-2-dimethylamino-ethyl)-2-fluoro-phenoxy]-ethyl}-amide

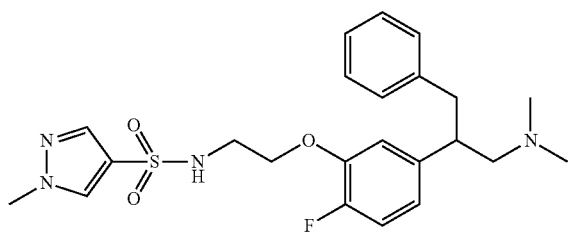

ESI-MS [M+H$^+$]=461 Calculated for C$_{21}$H$_{25}$FN$_4$O$_3$S=460

Example 32

1-Methyl-1H-imidazole-4-sulfonic acid {2-[5-(1-benzyl-2-dimethylaminoethyl)-2-fluoro-phenoxy]-ethyl}-amide

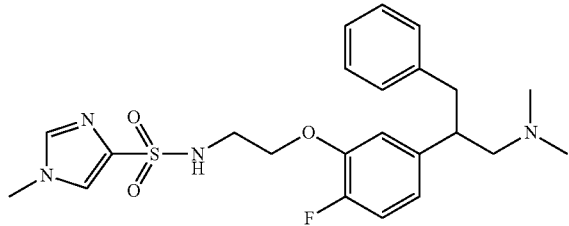

ESI-MS [M+H$^+$]=461 Calculated for C$_{21}$H$_{25}$FN$_4$O$_3$S=460

Example 33

1-Methyl-1H-pyrazole-4-sulfonic acid {2-[3-(1-benzyl-2-dimethylamino-ethyl)-4-fluoro-phenoxy]-ethyl}-amide

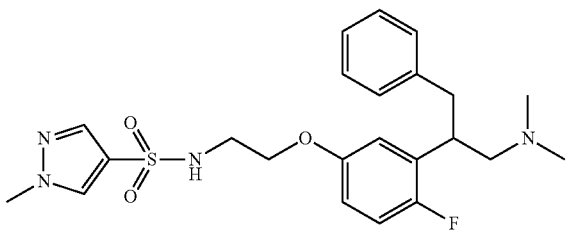

ESI-MS [M+H$^+$]=461 Calculated for C$_{21}$H$_{25}$FN$_4$O$_3$S=460

Example 34

1-Methyl-1H-pyrazole-4-sulfonic acid {2-[3-(1-benzyl-2-pyrrolidin-1-yl-ethyl)-phenoxy]-ethyl}-amide

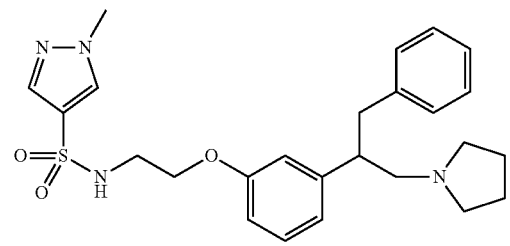 [SMILES: Cn1cc(S(=O)(=O)NCCOc2cccc(C(Cc3ccccc3)CN3CCCC3)c2)cn1]

34.1 3-(4-Chloro-phenyl)-2-(3-hydroxy-phenyl)-acrylonitrile

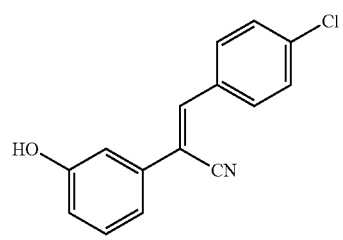 [SMILES: N#C/C(=C\c1ccc(Cl)cc1)c1cccc(O)c1]

Prepared in analogy to example 1 following steps 1.1 and 1.3.

34.2 3-(1-Amino-3-phenylpropan-2-yl)phenol

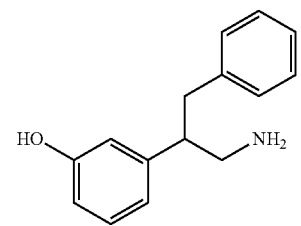 [SMILES: NCC(Cc1ccccc1)c1cccc(O)c1]

3-(3-Chlorophenyl)-2-(3-hydroxyphenyl)acrylonitrile (3.6 g, 14.08 mmol) was dissolved in 100 ml methanol, containing 0.02 eq Pd/C (0.3 g, 0.28 mmol) 10% on C. Hydrogenation was performed at room temperature over night. Reaction was filtered through celite and the solvent evaporated. The residue was suspended in ethyl acetate and the white precipitate was filtered and dried m=3.0 g (94%).

34.3 3-(1-Benzyl-2-pyrrolidin-1-yl-ethyl)-phenol

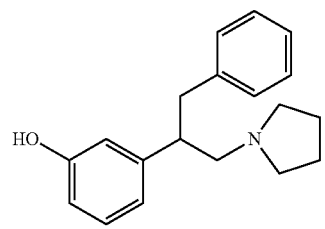 [SMILES: Oc1cccc(C(Cc2ccccc2)CN2CCCC2)c1]

To 3-(1-amino-3-phenylpropan-2-yl)phenol (0.6 g, 2.6 mmol) dissolved in 40 ml acetonitrile was added triethylamine (0.81 ml, 5.8 mmol) followed by 1,4-dibromobutane (0.37 ml, 3.2 mmol). The mixture was heated to reflux for 3 h then poured on ice-water and extracted twice with dichloromethane. The combined organic layers were washed with water and brine, dried over $Na_2SO_4$, filtered and the solvent evaporated to obtain a yellow oil. m=665 mg (90%)

34.4 1-Methyl-1H-pyrazole-4-sulfonic acid {2-[3-(1-benzyl-2-pyrrolidin-1-yl-ethyl)phenoxy]-ethyl}-amide

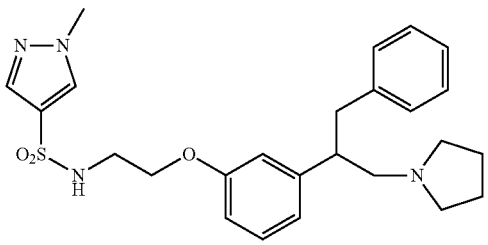 [SMILES: Cn1cc(S(=O)(=O)NCCOc2cccc(C(Cc3ccccc3)CN3CCCC3)c2)cn1]

Prepared in analogy to example 1 following steps 1.4-1.6.
ESI-MS [M+H$^+$]=469 Calculated for $C_{25}H_{32}N_4O_3S$=468

Example 35

1-Methyl-1H-imidazole-4-sulfonic acid {2-[3-(1-benzyl-2-pyrrolidin-1-yl-ethyl)phenoxy]-ethyl}-amide

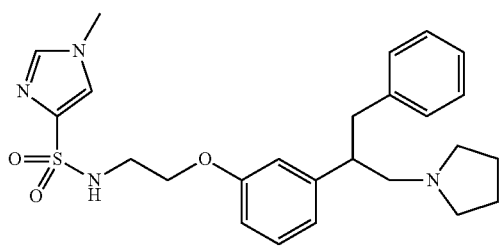 [SMILES: Cn1cnc(S(=O)(=O)NCCOc2cccc(C(Cc3ccccc3)CN3CCCC3)c2)c1]

Prepared from 1-methyl-1H-imidazole-4-sulfonic acid {2-[3-(2-amino-1-benzyl-ethyl)phenoxy]-ethyl}-amide (example 5) in analogy to example 34 step 3.
ESI-MS [M+H$^+$]=469 Calculated for $C_{25}H_{32}N_4O_3S$=468

Example 36

1-Methyl-1H-pyrazole-4-sulfonic acid {2-[3-(2-azetidin-1-yl-1-benzyl-ethyl)phenoxy]-ethyl}-amide

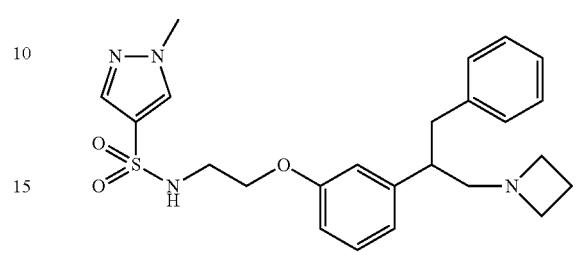

Prepared in analogy to example 35.
ESI-MS [M+H$^+$]=455 Calculated for $C_{24}H_{30}N_4O_3S$=454

Example 37

1-Methyl-1H-pyrazole-4-sulfonic acid 3-(2-azetidin-1-yl-1-benzyl-ethyl)benzylamide, hydrochloride

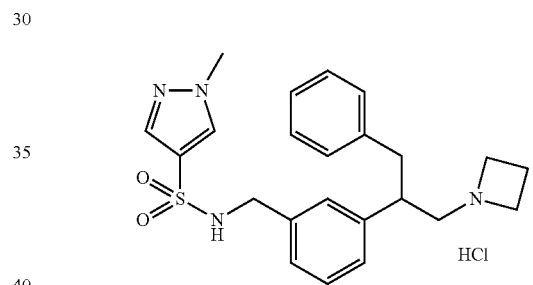

Prepared in analogy to example 13.
ESI-MS [M+H$^+$]=425 Calculated for $C_{23}H_{28}N_4O_2S$=424

Example 38

Propane-1-sulfonic acid [2-(3-{benzylamino-[1-(4-chloro-phenyl)-cyclobutyl]-methyl}-phenoxy)-ethyl]-amide

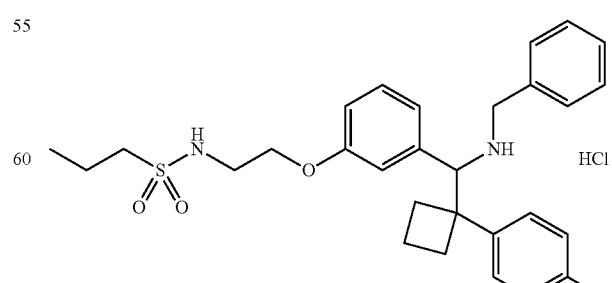

38.1 (3-Benzyloxy-phenyl)-[1-(4-chloro-phenyl)-cyclobutyl]-methanone

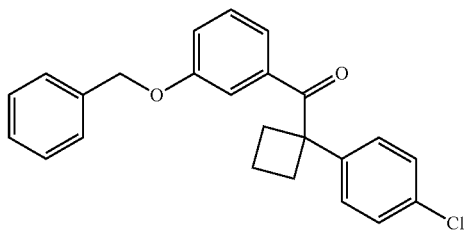 [SMILES: O=C(c1cccc(OCc2ccccc2)c1)C1(c2ccc(Cl)cc2)CCC1]

To a solution of 1-(4-chlorophenyl)cyclobutanecarbonitrile (2.5 g, 13 mmol) in tetrahydrofuran was added at −5° C. under nitrogen 4-(benzyloxy)phenyl)magnesium bromide (1 M, 39 ml, 39 mmol). The mixture was stirred over night at room temperature. A saturated solution of ammonium chloride and water was added. The organic layer was separated, and the aqueous layer extracted with diethyl ether. The combined organic layers were dried (sodium sulfate) and the solvent evaporated. Purification on $SiO_2$ afforded 3.3 g of desired product as colorless oil.

38.2 [1-(4-Chloro-phenyl)-cyclobutyl]-(3-hydroxy-phenyl)-methanone

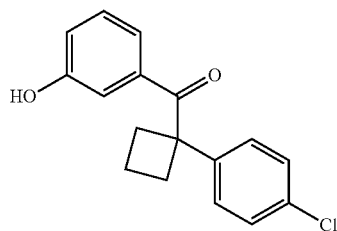 [SMILES: O=C(c1cccc(O)c1)C1(c2ccc(Cl)cc2)CCC1]

(3-Benzyloxy-phenyl)-[1-(4-chloro-phenyl)-cyclobutyl]-methanone (780 mg, 2 mmol) was dissolved in ethyl acetate, containing Pd/C (80 mg, 10% on C). Hydrogenation was performed at room temperature during 4 hours. Reaction was filtered through celite and the solvent evaporated. The product (548 mg) was used in the next step without further purification.

38.3 Propane-1-sulfonic acid (2-{3-[1-(4-chloro-phenyl)-cyclobutanecarbonyl]-phenoxy}-ethyl)-amide

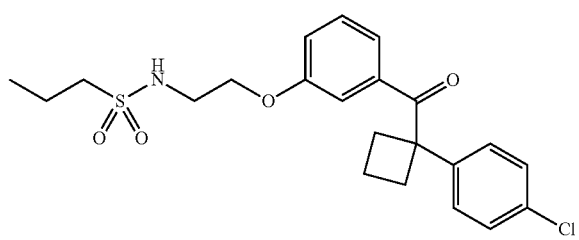 [SMILES: CCCS(=O)(=O)NCCOc1cccc(C(=O)C2(c3ccc(Cl)cc3)CCC2)c1]

Compound was prepared starting from 1-(4-chloro-phenyl)-cyclobutyl]-(3-hydroxy-phenyl)methanone in analogy to example 1 following the steps 1.4-1.6.

38.4 Propane-1-sulfonic acid [2-(3-{benzylamino-[1-(4-chloro-phenyl)-cyclobutyl]-methyl}-phenoxy)-ethyl]-amide

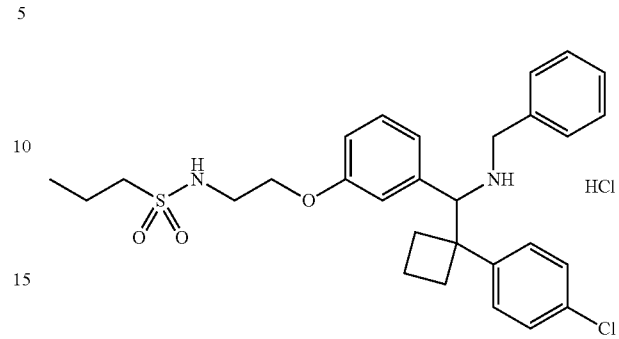

Titanium (IV) isopropoxide (235 mg, 0.83 mmol) was added under nitrogen at room temperature to a mixture of benzylamine (147 mg, 1.37 mmol) and propane-1-sulfonic acid (2-{3-[1-(4-chloro-phenyl)-cyclobutanecarbonyl]-phenoxy}-ethyl)-amide (120 mg, 0.27 mmol), followed by 1 ml of isopropanol. The mixture was stirred at 35° C. for 6 h, then over night at room temperature followed by addition of NaCNBH$_4$ (43 mg, 0.69 mmol) and heating to reflux for further 6 hours. The suspension was treated with water and diluted with ethylacetate and filtered. The organic layer was separated, washed with water, dried (sodium sulfate) and the solvent evaporated. Purification on $SiO_2$ afforded 14 mg of desired product which was further purified by transformation into the hydrochloride. (white solid, 2.7 mg)

ESI-MS [M+H$^+$]=527 Calculated for $C_{29}H_{35}ClN_2O_3S$=526

Example 39 tert-Butyl {2-[1-(4-chlorophenyl)cyclobutyl]-2-[3-({methyl[(1-methyl-1H-pyrazol-4-yl)sulfonyl]amino}methyl)phenyl]ethyl}carbamate

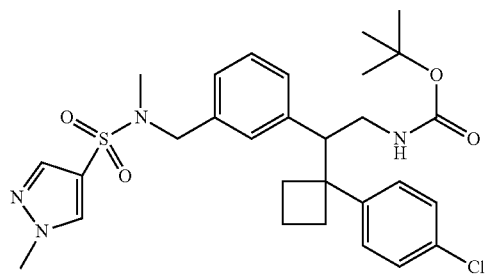 [SMILES: CN(Cc1cccc(C(CNC(=O)OC(C)(C)C)C2(c3ccc(Cl)cc3)CCC2)c1)S(=O)(=O)c1cnn(C)c1]

39.1 1-Chloro-4-{1-[(E)-2-nitroethenyl]cyclobutyl}benzene

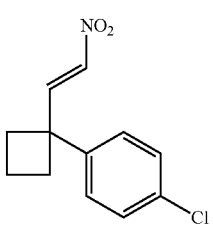 [SMILES: O=[N+]([O-])/C=C/C1(c2ccc(Cl)cc2)CCC1]

1-(4-Chlorophenyl)cyclobutanecarbaldehyde (4.14 g, 21.42 mmol), tert-butanol (10 ml, 106 mmol), potassium tert-butanolate (0.24 g, 2.142 mmol) and nitromethane (1.444 ml, 26.8 mmol) were dissolved in tetrahydrofuran (10 ml). The reaction mixture was stirred at room temperature overnight. The reaction mixture was diluted with ethyl acetate, washed with water and the organic layer was dried (magnesium sulfate) and concentrated in vacuo. The crude product (5.2 g, 1-(1-(4-chlorophenyl)cyclobutyl)-2-nitroethanol) was used without further purification for the next step.

1-(1-(4-Chlorophenyl)cyclobutyl)-2-nitroethanol (5.2 g, 20.34 mmol) was dissolved in dichloromethane (41 ml) and trifluoroacetic acid anhydride (2.87 ml, 20.34 mmol) was added. The reaction mixture was cooled to 0° C. and triethylamine (5.67 ml, 40.7 mmol) was added dropwise. The reaction was slowly warmed to room temperature and stirring Was continued for 2 h. The reaction mixture was diluted with dichloromethane and washed with aqueous hydrochloric acid (1 N). The organic layer was dried (magnesium sulfate) and concentrated in vacuo. The crude product was purified by flash chromatography (silica, dichloromethane, methanol). Yield: 3.99 g (16.79 mmol, 83%)

39.2 3-{1-[1-(4-Chlorophenyl)cyclobutyl]-2-nitroethyl}benzonitrile

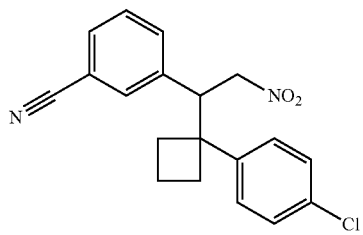 [SMILES: N#Cc1cccc(C(C[N+](=O)[O-])C2(c3ccc(Cl)cc3)CCC2)c1]

3-Iodobenzonitrile (3.76 g, 16.41 mmol) dissolved in tetrahydrofuran (1.5 ml) was cooled to −30° C. A solution of isopropylmagnesium chloride in tetrahydrofuran (2 M, 8.84 ml, 17.67 mmol) was added dropwise at −30° C. over 25 min. The reaction mixture was cooled to −78° C. A solution of (E)-1-chloro-4(1-(2-nitrovinyl)cyclobutyl)benzene (3.0 g, 12.62 mmol) in tetrahydrofuran (0.5 ml) was added dropwise. Aqueous work-up yielded the desired product which was used without further purification for the next step. Yield: 3.3 g (8.71 mmol, 69%, purity: 90% by HPLC)

39.3 3-{2-Amino-1-[1-(4-chlorophenyl)cyclobutyl]ethyl}benzonitrile

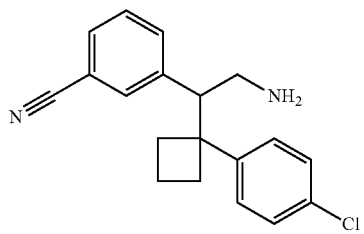

3-{1-[1-(4-Chlorophenyl)cyclobutyl]-2-nitroethyl}benzonitrile (3.0 g, 8.8 mmol) was dissolved in tetrahydrofuran (37 ml) and zinc dust (8.63 g, 132 mmol) was added followed by acetic acid (7.34 ml, 8.8 mmol). The reaction mixture was stirred at room temperature for 2 h. The reaction mixture was filtered through celite and diluted with ethyl acetate. The solution was washed with aqueous sodium bicarbonate (two times), dried (magnesium sulfate) and concentrated in vacuo. Yield: 2.41 g (7.75 mmol, 88%)

39.4 tert-Butyl {2-[1-(4-chlorophenyl)cyclobutyl]-2-(3-cyanophenyl)ethyl}carbamate

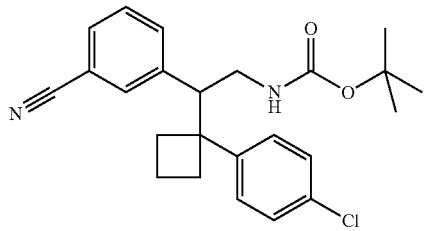 [SMILES: CC(C)(C)OC(=O)NCC(c1cccc(C#N)c1)C1(c2ccc(Cl)cc2)CCC1]

3-{2-Amino-1-[1-(4-chlorophenyl)cyclobutyl]ethyl}benzonitrile (2.0 g, 6.43 mmol) was dissolved in acetonitrile and di-tert-butyl dicarbonate (2.106 g, 9.65 mmol) and ethyldiisopropylamine (2.495 g, 19.3 mmol) was added. The reaction mixture was then heated to 60° C. for 5 h. The reaction mixture was cooled to room temperature, diluted with ethyl acetate and washed with aqueous hydrochloric acid (1 N). The organic phase was successively washed with aqueous hydrochloric acid (1 N), saturated sodium bicarbonate and brine. After drying (magnesium sulfate) the solution was concentrated in vacuo. The crude product was purified by flash chromatography (silica, dichloromethane, methanol). Yield: 2.5 g (6.08 mmol, 95%)

39.5 tert-Butyl {2-[1-(4-chlorophenyl)cyclobutyl]-2-(3-formylphenyl)ethyl}carbamate

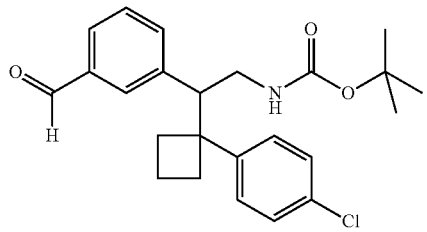 [SMILES: CC(C)(C)OC(=O)NCC(c1cccc(C=O)c1)C1(c2ccc(Cl)cc2)CCC1]

tert-Butyl {2-[1-(4-chlorophenyl)cyclobutyl]-2-(3-formylphenyl)ethyl}carbamate (0.5 g, 1.22 mmol) was dissolved in toluene (20 ml), cooled to −78° C. and a solution of diisobutyl aluminum hydride (1 M, 3.65 ml, 3.65 mmol) was added dropwise and stirring was continued at −78° C. for 2 h. The cold reaction mixture was carefully poured into aqueous hydrochloric acid (1 M). The aqueous layer was extracted with ethyl acetate (three times). The combined organic layers were washed successively with sodium bicarbonate and brine. The solution was dried (magnesium sulfate) and concentrated in vacuo. The crude product was purified by flash chromatography (silica, ethyl acetate, n-heptane). Yield: 0.384 g (0.928 mmol, 76%)

39.6 tert-Butyl (2-[1-(4-chlorophenyl)cyclobutyl]-2-{3-[(methylamino)methyl]phenyl}ethyl)carbamate

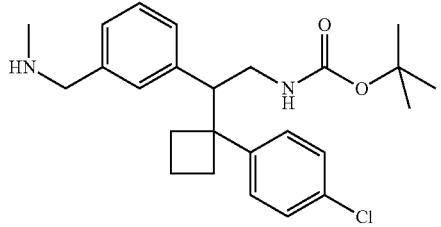 [SMILES: CNCc1cccc(C(CNC(=O)OC(C)(C)C)C2(c3ccc(Cl)cc3)CCC2)c1]

tert-Butyl {2-[1-(4-chlorophenyl)cyclobutyl]-2-(3-formylphenyl)ethyl}carbamate (0.19 g, 0.459 mmol) was dissolved in dichloromethane and methylamine (1.15 ml, 2.295 mmol) was added. The reaction mixture was stirred at room temperature for 1 h. Sodium triacetoxyborohydride (0.146 g, 0.689 mmol) was added. The reaction mixture was stirred at room temperature over night. The reaction mixture was diluted with sodium hydroxide (1 N) and extracted with ethyl acetate. The combined extracts were dried (magnesium sulfate), concentrated in vacuo and the crude product purified by flash chromatography (silica, dichloromethane, methanol). Yield: 0.11 g (0.256 mmol, 56%)

39.7 tert-Butyl {2-[1-(4-chlorophenyl)cyclobutyl]-2-[3-({methyl[(1-methyl-1H-pyrazol-4-yl)sulfonyl]amino}methyl)phenyl]ethyl}carbamate

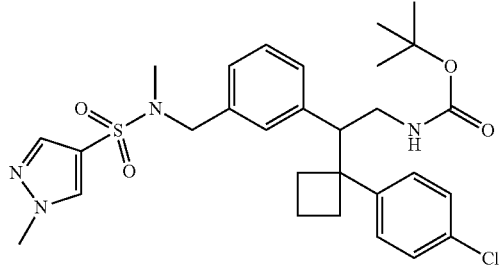 [SMILES: CN(Cc1cccc(C(CNC(=O)OC(C)(C)C)C2(c3ccc(Cl)cc3)CCC2)c1)S(=O)(=O)c1cnn(C)c1]

tert-Butyl (2-[1-(4-chlorophenyl)cyclobutyl]-2-{3-[(methylamino)methyl]phenyl}ethyl)carbamate (35 mg, 0.082 mmol) was dissolved in dichloromethane (0.8 mL). 4-Dimethylaminopyridine (10 mg, 0.082 mmol) and 1-methyl-1H-pyrazole-4-sulfonyl chloride (16 mg, 0.09 mmol) was added. The reaction mixture was stirred at room temperature over night. The reaction mixture was diluted with ethyl acetate (20 ml) and washed with aqueous hydrochloric acid (1 N, 5 ml, twice) and sodium bicarbonate. The organic layer was dried (magnesium sulfate) and concentrated in vacuo. The crude product was purified by preparative thin layer chromatography (silica, ethyl acetate, n-heptane). Yield: 36 mg (0.063 mmol, 77%)

ESI-MS [M-CO$_2$-isobutene+H$^+$]=473 Calculated for C$_{29}$H$_{37}$ClN$_4$O$_4$S=572

Example 40 tert-Butyl {2-[1-(4-chlorophenyl)cyclobutyl]-2-(3-{[methyl(propylsulfonyl)amino]methyl}phenyl)ethyl}carbamate

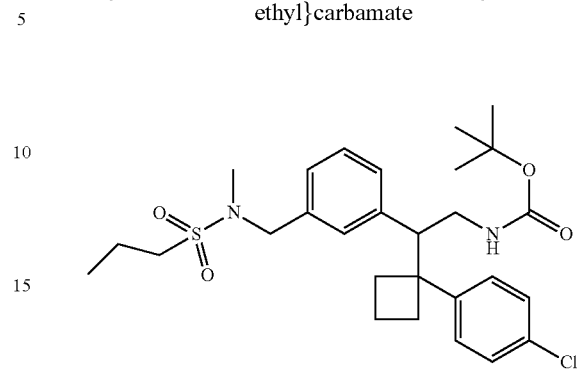

tert-Butyl {2-[1-(4-chlorophenyl)cyclobutyl]-2-(3-{[methyl(propylsulfonyl)amino]methyl}-phenyl)ethyl}carbamate was prepared analog to example 39.

ESI-MS [M-CO$_2$-isobutene+H$^+$]=435 Calculated for C$_{28}$H$_{39}$ClN$_2$O$_4$S=534

Example 41 tert-Butyl {2-[1-(4-chlorophenyl)cyclobutyl]-2-[3-({methyl[(1-methyl-1H-imidazol-4-yl)sulfonyl]amino}methyl)phenyl]ethyl}carbamate

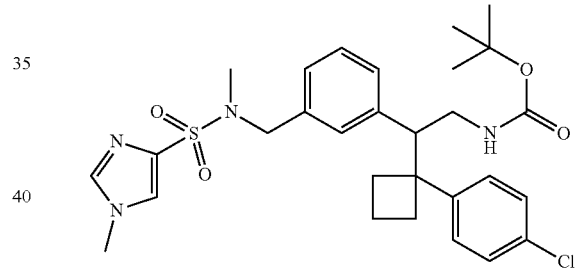

tert-Butyl {2-[1-(4-chlorophenyl)cyclobutyl]-2-[3-({methyl[(1-methyl-1H-imidazol-4-yl)sulfonyl]amino}methyl)phenyl]ethyl}carbamate was prepared analog to example 39.

ESI-MS [M+H$^+$]=573 Calculated for C$_{29}$H$_{37}$ClN$_4$O$_4$S=572

Example 42

N-(3-{2-Amino-1-[1-(4-chlorophenyl)cyclobutyl]ethyl}benzyl)-N-methylpropane-1-sulfonamide hydrochloride

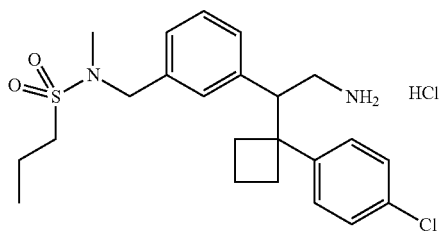 [SMILES: CCCS(=O)(=O)N(C)Cc1cccc(C(CN)C2(c3ccc(Cl)cc3)CCC2)c1 ; Cl]

tert-Butyl {2-[1-(4-chlorophenyl)cyclobutyl]-2-(3-{[methyl(propylsulfonyl)amino]methyl}phenyl)ethyl}carbamate (20.9 mg, 0.039 mmol) was treated with hydrochloric acid in isopropanol (5 M, 1 ml) at room temperature. The solvent was evaporated in vacuo. Water (1 ml) was added and the product was freeze-dried. Yield: 16 mg (0.034 mmol, 87%)

ESI-MS [M+H$^+$]=435 Calculated for C$_{23}$H$_{31}$ClN$_2$O$_2$S=434

Example 43

N-(3-{2-Amino-1-[1-(4-chlorophenyl)cyclobutyl]ethyl}benzyl)-3-fluoro-N-methylpropane-1-sulfonamide hydrochloride

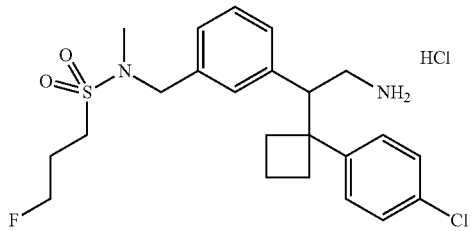 [SMILES: CN(Cc1cccc(C(CN)C2(c3ccc(Cl)cc3)CCC2)c1)S(=O)(=O)CCCF ; Cl]

N-(3-{2-Amino-1-[1-(4-chlorophenyl)cyclobutyl]ethyl}benzyl)-3-fluoro-N-methylpropane-1-sulfonamide hydrochloride was prepared analog to example 42.

ESI-MS [M+H$^+$]=453 Calculated for C$_{23}$H$_{30}$ClFN$_2$O$_2$S=452

Example 44

N-(3-{2-Amino-1-[1-(4-chlorophenyl)cyclobutyl]ethyl}benzyl)-N,1-dimethyl-1H-imidazole-4-sulfonamide hydrochloride

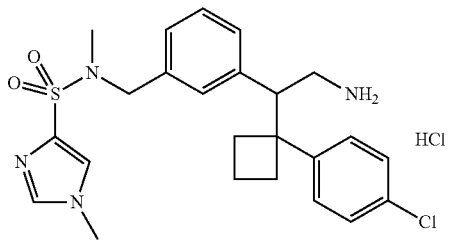 [SMILES: CN(Cc1cccc(C(CN)C2(c3ccc(Cl)cc3)CCC2)c1)S(=O)(=O)c1cn(C)cn1 ; Cl]

N-(3-{2-Amino-1-[1-(4-chlorophenyl)cyclobutyl]ethyl}benzyl)-N,1-dimethyl-1H-imidazole-4-sulfonamide hydrochloride was prepared in analogy to example 42.

$^1$H-NMR (d$^6$-DMSO): 1.63 (m, 1H), 1.84 (m, 1H), 2.0 (q, J=8.6 Hz, 1H), 2.29 (m, 2H), 2.42 (m, 1H), 2.5 (s, 3H), 2.82 (m, 1H), 3.17 (m, 1H), 3.43 (d, J=10.6 Hz, 1H), 3.73 (s, 3H), 4.02 (d, J=14.4 Hz, 1H), 4.10 (d, J=14.4 Hz, 1H), 6.78 (m, 4H), 7.24 (m, 4H), 7.8 (m, 4H), 7.9 (s, 1H).

Example 45

N-(3-{2-Amino-1-[1-(4-chlorophenyl)cyclobutyl]ethyl}benzyl)-N,1-dimethyl-1H-pyrazole-4-sulfonamide hydrochloride

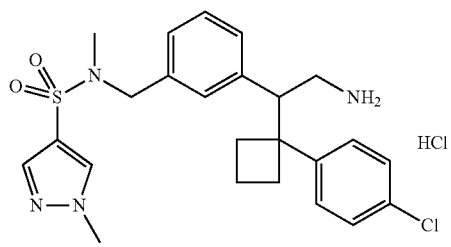 [SMILES: CN(Cc1cccc(C(CN)C2(c3ccc(Cl)cc3)CCC2)c1)S(=O)(=O)c1cnn(C)c1 ; Cl]

N-(3-{2-Amino-1-[1-(4-chlorophenyl)cyclobutyl]ethyl}benzyl)-N,1-dimethyl-1H-pyrazole-4-sulfonamide hydrochloride was prepared in analogy to example 42.

ESI-MS [M+H$^+$]=473 Calculated for C$_{24}$H$_{29}$ClN$_4$O$_2$S=472

Example 46

3-Benzyl-3-{3-[2-(1-methyl-1H-pyrazole-4-sulfonylamino)-ethoxy]-phenyl}-azetidine-1-carboxylic acid ethyl ester

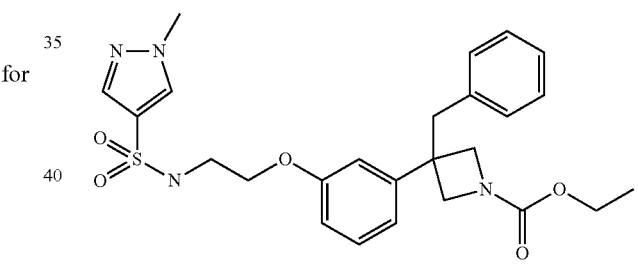

46.1 Ethyl 2-cyano-2-(3-methoxyphenyl)acetate

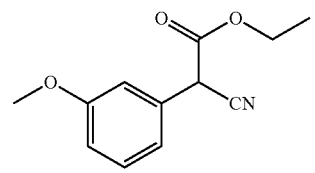 [SMILES: CCOC(=O)C(C#N)c1cccc(OC)c1]

A mixture of 3-iodoanisole (11.2 ml, 85 mmol), ethyl cyanoacetate (27.3 ml, 256 mmol), potassium carbonate (47.2 g, 342 mmol), copper(I) iodide (1.63 g, 8.55 mmol) and L-proline (1.97 g, 17.1 mmol) in dimethylsulfoxide (300 ml) was heated to 90° C. under argon for 11 h and then at room temperature over night. The solution was poured into 1N hydrochloric acid, extracted with ethyl acetate. The organic layer was washed with brine, dried over sodium bicarbonate, filtered and the solvent evaporated to obtain a brown oil. Purification on 12 g SiO$_2$ using 20% ethyl acetate in cyclohexane afforded a clear oil m=16.8 g (44.8%)

46.2 Ethyl 2-cyano-2-(3-methoxyphenyl)-3-phenylpropanoate

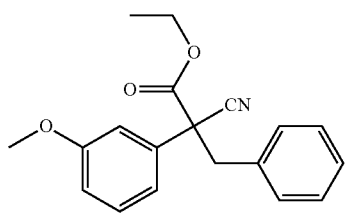 [SMILES: CCOC(=O)C(C#N)(Cc1ccccc1)c1cccc(OC)c1]

To a solution of diisopropylamine (7.80 ml, 54.7 mmol) in 100 ml dry tetrahydrofuran at −78° C. was added n-butyl lithium (34.2 ml, 54.7 mmol) and stirred for 1 h while the reaction mixture was allowed to warm up to −40° C. A solution of ethyl 2-cyano-2-(3-methoxyphenyl)acetate (10 g, 45.6 mmol) in 100 ml dry tetrahydrofuran was added and the mixture stirred for 30 min. Then (bromomethyl)benzene (8.13 ml, 68.4 mmol) was added and the reaction was stirred over night. The solvent was evaporated and the residue dissolved in ethyl acetate, which was washed with 10% citric acid, water and brine. The combined organic layers were dried over sodium bicarbonate, filtered and the solvent evaporated to obtain a yellow-orange oil. Purification on 120 g SiO$_2$ using 20% ethyl acetate in cyclohexene afforded a clear colourless oil m=9.4 g (66.6%).

46.3 Ethyl 3-amino-2-benzyl-2-(3-methoxyphenyl)propanoate

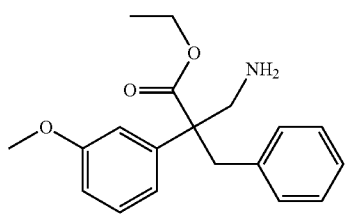 [SMILES: CCOC(=O)C(CN)(Cc1ccccc1)c1cccc(OC)c1]

To a solution of ethyl 2-cyano-2-(3-methoxyphenyl)-3-phenylpropanoate (9.1 g, 29.4 mmol) in ethanol (150 ml) was added Raney-Nickel (10.1 g, 58.8 mmol). Hydrogenation occurred at room temperature over night. The mixture was filtered and the solvent evaporated. Purification on 80 g SiO$_2$ using 5% methanol in dichloromethane afforded a colourless solid. Hydrochloride was formed by adding 1N hydrochloric acid in diethyl ether (white solid). m=4.0 g (43%)

46.4 3-Benzyl-3-(3-methoxyphenyl)azetidin-2-one

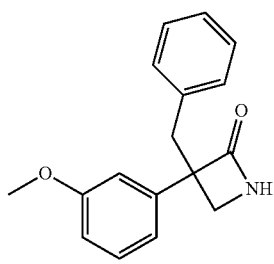 [SMILES: COc1cccc(C2(Cc3ccccc3)CNC2=O)c1]

Synthesis as described in J. Med. Chem, (11), 1968, 466-470

46.5 Synthesis of 3-benzyl-3-(3-methoxyphenyl)azetidine

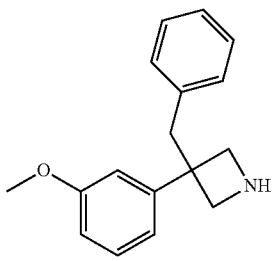 [SMILES: COc1cccc(C2(Cc3ccccc3)CNC2)c1]

A 1M lithium aluminium hydride solution in tetrahydrofuran (14 ml, 14 mmol) was added to a stirred solution of 3-benzyl-3-(3-methoxyphenyl)azetidin-2-one (1.7 g, 6.36 mmol) in tetrahydrofuran and heated to reflux for 4 h. The solution was cooled and quenched by careful addition of a 2M sodium hydroxide solution and then extracted with ether. The organic phase was dried over sodium bicarbonate and purified on 12 g SiO$_2$ using 20% methanol in dichloromethane (clear colourless oil). m=520 mg (32%)

46.6 3 3-Benzyl-3-(3-methoxy-phenyl)-azetidine-1-carboxylic acid ethyl ester

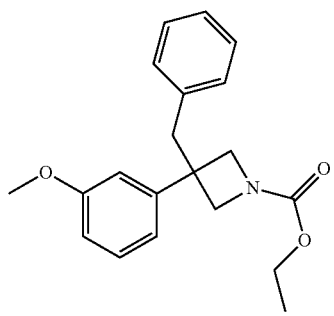 [SMILES: CCOC(=O)N1CC(Cc2ccccc2)(c2cccc(OC)c2)C1]

To a stirred and cooled solution of 3-benzyl-3-(3-methoxyphenyl)azetidine (0.45 g, 1.776 mmol) under argon in dichloromethane containing diisopropylamine (0.465 ml, 2.66 mmol) was added dropwise ethyl chloroformate (0.26 ml, 2.7 mmol). The reaction was stirred over night while it was allowed to warm up to room temperature. Hydrochloric acid (1N) was added and the mixture diluted with dichloromethane. The organic layer was separated and the aqueous layer extracted twice with dichloromethane. The combined organic layers were washed subsequently with water, sodium bicarbonate and brine, dried over sodium bicarbonate, filtered and the solvent evaporated to obtain desired product. m=546 mg (61%)

46.7 3-Benzyl-3-{3-[2-(1-methyl-1H-pyrazole-4-sulfonylamino)-ethoxy]-phenyl}-azetidine-1-carboxylic acid ethyl ester

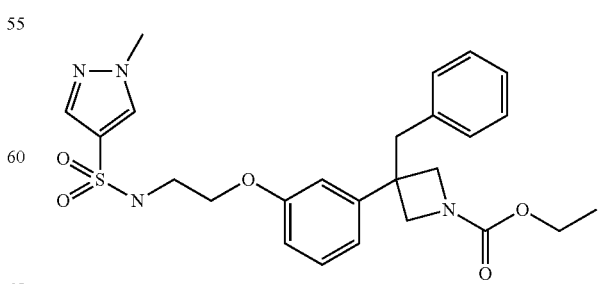

Prepared in analogy to example 1 following steps 1.3-1.6
ESI-MS [M+H$^+$]=499 Calculated for C$_{25}$H$_{30}$N$_4$O$_5$S=498

Example 47

3-Benzyl-3-{3-[2-(1-methyl-1H-imidazole-4-sulfonylamino)-ethoxy]-phenyl}-azetidine-1-carboxylic acid ethyl ester

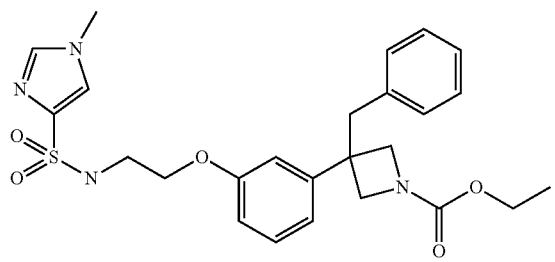 [SMILES: CCOC(=O)N1CC(Cc2ccccc2)(c2cccc(OCCNS(=O)(=O)c3cn(C)cn3)c2)C1]

Prepared in analogy to example 46.
ESI-MS [M+H$^+$]=499 Calculated for $C_{25}H_{30}N_4O_5S$=498

Example 48

3-Benzyl-3-[3-(2-cyclopropylmethanesulfonylamino-ethoxy)-phenyl]-azetidine-1-carboxylic acid ethyl ester

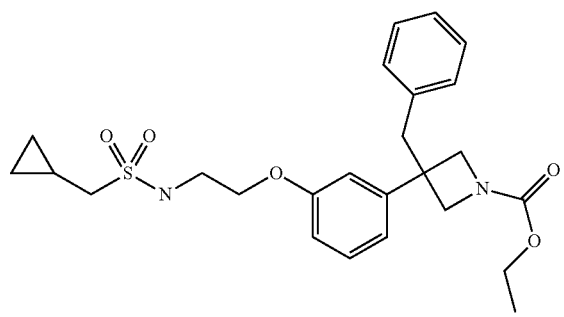 [SMILES: CCOC(=O)N1CC(Cc2ccccc2)(c2cccc(OCCNS(=O)(=O)CC3CC3)c2)C1]

Prepared in analogy to example 46.
ESI-MS [M+H$^+$]=473 Calculated for $C_{25}H_{32}N_2O_5S$=472

Example 49

N-{2-[3-(3-Benzyl-azetidin-3-yl)-phenoxy]-ethyl}-C-cyclopropyl-methane sulfonamide

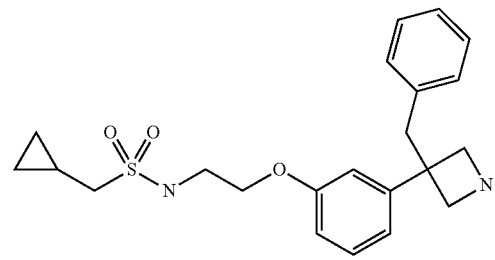 [SMILES: O=S(=O)(CC1CC1)NCCOc1cccc(C2(Cc3ccccc3)CNC2)c1]

To 3-benzyl-3-[3-(2-cyclopropylmethanesulfonylamino-ethoxy)-phenyl]-azetidine-1-carboxylic acid ethyl ester (50 mg, 0.11 mmol) was added 4 ml 2N NaOH/EtOH. The mixture was heated for 1 hour in a microwave. After cooling to room temperature 50% brine was added and the mixture extracted with dichloromethane. The combined organic layers were washed with brine, dried over sodium bicarbonate, filtered and the solvent evaporated. The residue was purified on 4 g SiO$_2$ using 10% methanol in dichloromethane affording the desired product as a clear oil. m=15.5 mg
ESI-MS [M+H$^+$]=401 Calculated for $C_{22}H_{28}N_2O_3S$=400

Example 50

1-Methyl-1H-pyrazole-4-sulfonic acid {2-[3-(3-benzyl-azetidin-3-yl)-phenoxy]-ethyl}-amide

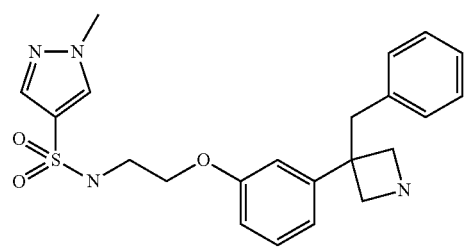 [SMILES: Cn1cc(S(=O)(=O)NCCOc2cccc(C3(Cc4ccccc4)CNC3)c2)cn1]

Prepared in analogy to example 49.
ESI-MS [M+H$^+$]=427 Calculated for $C_{22}H_{26}N_4O_3S$=426

Example 51

1-Methyl-1H-imidazole-4-sulfonic acid {2-[3-(3-benzyl-azetidin-3-yl)phenoxy]-ethyl}-amide

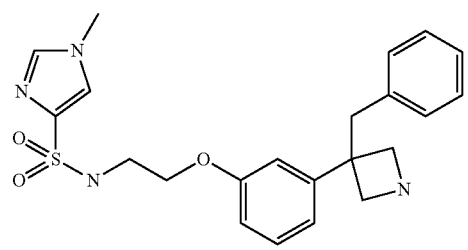 [SMILES: Cn1cnc(S(=O)(=O)NCCOc2cccc(C3(Cc4ccccc4)CNC3)c2)c1]

Prepared in analogy to example 49.
ESI-MS [M+H$^+$]=427 Calculated for $C_{22}H_{26}N_2O_3S$=426

Example 52

1-Methyl-1H-imidazole-4-sulfonic acid {2-[5-(3-benzyl-1-methyl-azetidin-3-yl)-2-fluoro-phenoxy]-ethyl}-amide

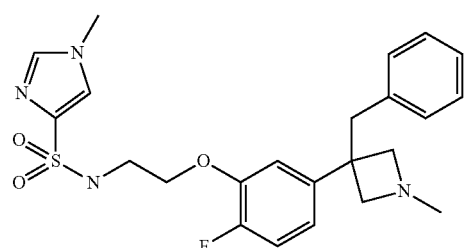

52.1 2-(4-Fluoro-3-methoxy-phenyl)-3-phenyl-acrylonitrile

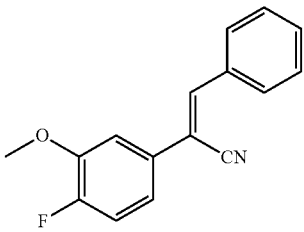 [SMILES: COc1cc(/C(C#N)=C/c2ccccc2)ccc1F]

To a solution of 4-fluoro-3-methoxyphenylacetonitrile (10.8 g, 65.4 mmol) in 200 ml EtOH was added a sodium ethoxide 21% solution in EtOH (26.9 ml, 71.9 mmol). Benzaldehyde was added (6.64 ml, 65.4 mmol) and stirred at room temperature over night. The white precipitate was filtered and washed with diethylether and dried to obtain 14.23 g of pale yellow crystals (86%).
ESI-MS [M+H$^+$]=254 Calculated for $C_{16}H_{12}FNO$=253

52.2 2-(4-Fluoro-3-methoxy-phenyl)-3-phenyl-propionitrile

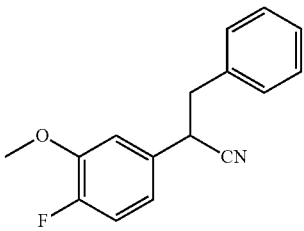 [SMILES: COc1cc(C(C#N)Cc2ccccc2)ccc1F]

To a suspension of (Z)-2-(4-fluoro-3-methoxyphenyl)-3-phenylacrylonitrile (14.23 g, 56.2 mmol) in EtOH was added sodium borohydride (2.66 g, 70.2 mmol) and stirred at room temperature over night. Poured into ice-water, added 5% citric acid and extracted three times with EtOAc. The combined organic layers were washed with brine, dried over MgSO$_4$, filtered and evaporated to obtain 15.9 g of an orange oil.
ESI-MS [M+H$^+$]=256 Calculated for $C_{16}H_{14}FNO$=255

52.3 Benzyl-cyano-(4-fluoro-3-methoxy-phenyl)-acetic acid ethyl ester

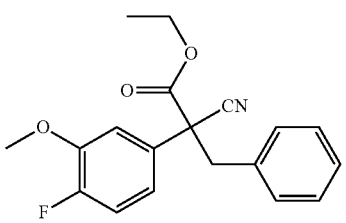 [SMILES: CCOC(=O)C(C#N)(Cc1ccccc1)c1ccc(F)c(OC)c1]

To a −78° C. cooled solution of diisopropylamine (5.11 ml, 35.8 mmol) in THF was added n-butyllithium (22.40 ml, 35.8 mmol) and stirred for 1 h while the reaction mixture was allowed to warm up <−40° C. 2-(4-Fluoro-3-methoxyphenyl)-3-phenylpropanenitrile (6.1 g, 23.89 mmol) dissolved in THF was added followed by ethyl chloroformiate (3.42 ml, 35.8 mmol). The reaction mixture was stirred over night and was allowed to heat up to room temperature. Evaporated solvents and redissolved in EtOAc, washed with 10% citric acid, water and brine and the combined organic layers were dried over MgSO$_4$, filtered and evaporated to obtain 7.2 g of a yellow oil, that was purified by flash chromatography on 330 g SiO$_2$ using 20% EtOAc in cyclohexene to obtain 18.26 g of the desired product as a pale yellow oil.
ESI-MS [M+H$^+$]=328 Calculated for $C_{19}H_{18}FNO_3$=327

52.4 3-Benzyl-3-{4-fluoro-3-[2-(1-methyl-1H-imidazole-4-sulfonylamino)-ethoxy]-phenyl}-azetidine-1-carboxylic acid ethyl ester

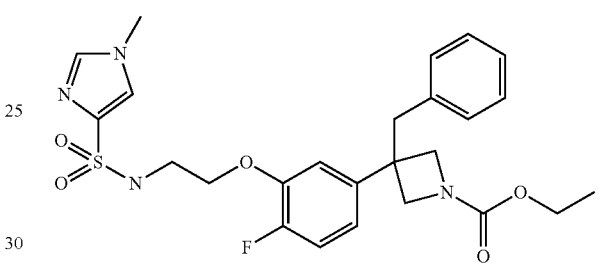

Prepared in analogy to example 46 following steps 46.4 to 46.7.

52.5 1-Methyl-1H-imidazole-4-sulfonic acid {2-[5-(3-benzyl-1-methyl-azetidin-3-yl)-2-fluoro-phenoxy]-ethyl}-amide

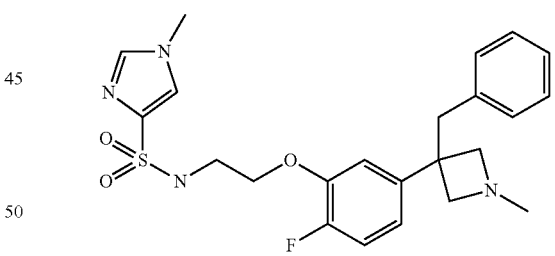

To ethyl 3-benzyl-3-(4-fluoro-3-(2-(1-methyl-1H-imidazole-4-sulfonamido)ethoxy)phenyl)azetidine-1-carboxylate (20.8 mg, 0.040 mmol) in tetrahydrofuran (1 ml) was added a 1M lithium aluminium hydride solution in tetrahydrofuran (0.121 ml, 0.121 mmol) and refluxed for 2 h. Cooled down to room temperature and 2N NaOH was slowly added and extracted twice with dichloromethane, washed with sodium bicarbonate and brine, dried over MgSO$_4$, filtered, evaporated and purified by flash silica gel chromatography on 4 g SiO$_2$-cartridge using 10% MeOH in dichloromethane affording 8.9 mg of the titled compound as a white solid.
ESI-MS [M+H$^+$]=459 Calculated for $C_{23}H_{27}FN_4O_3S$=458

Example 53

1-Methyl-1H-imidazole-4-sulfonic acid {2-[5-(3-benzyl-1-methyl-azetidin-3-yl)-2-fluoro-phenoxy]-ethyl}-methyl-amide

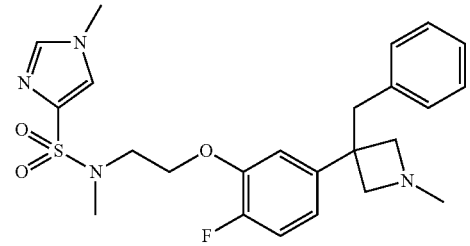 [SMILES: CN1CC(Cc2ccccc2)(c2ccc(F)c(OCCNS(=O)(=O)c3cn(C)cn3)c2)C1]

53.1 3-Benzyl-3-(4-fluoro-3-{2-[methyl-(1-methyl-1H-imidazole-4-sulfonyl)-amino]-ethoxy}-phenyl)-azetidine-1-carboxylic acid ethyl ester

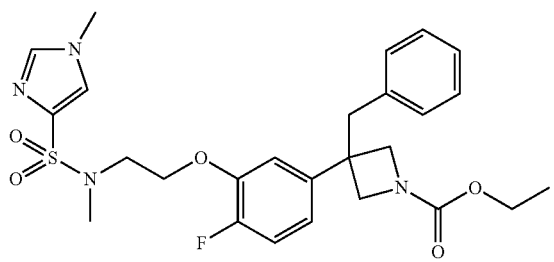 [SMILES: CCOC(=O)N1CC(Cc2ccccc2)(c2ccc(F)c(OCCN(C)S(=O)(=O)c3cn(C)cn3)c2)C1]

A solution of ethyl 3-benzyl-3-(3-(2-(1-methyl-1H-imidazole-4-sulfonamido)ethoxy)phenyl) azetidine-1-carboxylate (39.5 mg, 0.079 mmol) containing caesium carbonate (51.6 mg, 0.158 mmol) and methyl iodide (9.91 µl. 0.158 mmol) was put in the microwave at 100° C. for 2 h. Evaporated solvents, added water and extracted twice with dichloromethane and the organic layers were filtered, dried over MgSO$_4$, evaporated and purified by flash silica gel chromatography on 4 g SiO$_2$-cartridge using 10% in dichloromethane to afford 26.8 g of a clear colourless oil.

ESI-MS [M+H$^+$]=513 Calculated for C$_{26}$H$_{32}$N$_4$O$_5$S=512

53.2 1-Methyl-1H-imidazole-4-sulfonic acid {2-[5-(3-benzyl-1-methyl-azetidin-3-yl)-2-fluoro-phenoxy]-ethyl}-methyl-amide Prepared in analogy to Example 52 step 5
ESI-MS [M+H$^+$]=523 Calculated for C$_{24}$H$_{25}$F$_3$N$_4$O$_4$S=522

Example 54

1-Methyl-1H-imidazole-4-sulfonic acid (2-{3-[3-benzyl-1-(2,2,2-trifluoro-ethyl)-azetidin-3-yl]-phenoxy}-ethyl)-amide

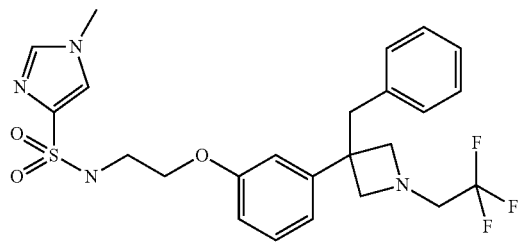 [SMILES: Cn1cnc(S(=O)(=O)NCCOc2cccc(C3(Cc4ccccc4)CN(CC(F)(F)F)C3)c2)c1]

54.1 1-Methyl-1H-imidazole-4-sulfonic acid (2-{3-[3-benzyl-1-(2,2,2-trifluoro-acetyl)azetidin-3-yl]-phenoxy}-ethyl)-amide

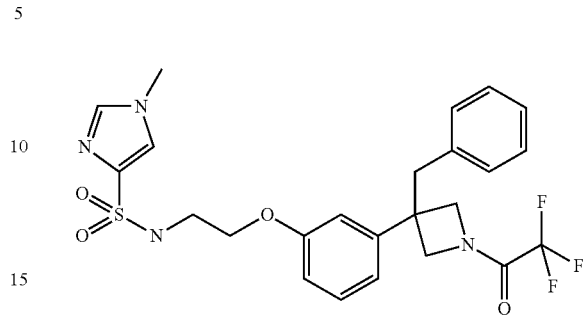

To a stirred solution of N-(2-(3-(3-benzylazetidin-3-yl)phenoxy)ethyl)-1-methyl-1H-imidazole-4-sulfonamide (55.6 mg, 0.130 mmol) in dry tetrahydrofuran (1 ml) containing diisopropylamine (0.057 ml, 0.326 mmol) under argon was added trifluoroacetic anhydride (0.036 ml, 0.261 mmol) and stirred at room temperature for 2 h. Poured into ice water, removed tetrahydrofuran under reduced pressure and re-dissolved in EtOAc. Washed with 10% citric acid, sodium bicarbonate and brine, dried over MgSO$_4$, filtered and evaporated to obtain 75.3 mg of the desired crude product as pale yellow oil.

ESI-MS [M+H$^+$]=523 Calculated for C$_{24}$H$_{25}$F$_3$N$_4$O$_4$S=522

54.2 1-Methyl-1H-imidazole-4-sulfonic acid (2-{3-[3-benzyl-1-(2,2,2-trifluoro-ethyl)azetidin-3-yl]-phenoxy}-ethyl)-amide

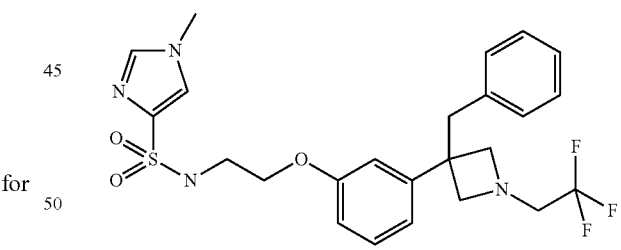

To a solution of N-(2-(3-(3-benzyl-1-(2,2,2-trifluoroacetyl)azetidin-3-yl)phenoxy)ethyl)-1-methyl-1H-imidazole-4-sulfonamide (60.7 mg, 0.116 mmol) in dry tetrahydrofuran (2 ml) was added a 2M solution of borane dimethyl sulfide complex (0.290 ml, 0.581 mmol) and stirred at 60° C. for 3 h. Quenched by the dropwise addition of water and refluxed for an other 2 h, the solution was saponified with NaOH (2N) and extracted three times with dichloromethane, dried over MgSO$_4$, filtered, evaporated and purified by flash silica gel chromatography on 4 g SiO$_2$-cartridge using 5% MeOH in dichloromethane to afford 18.4 mg of a white solid.

ESI-MS [M+H$^+$]=509 Calculated for C$_{24}$H$_{27}$F$_3$N$_4$O$_3$S=508

Example 55

1-Methyl-1H-imidazole-4-sulfonic acid (2-{3-[3-benzyl-1-(2,2-difluoro-ethyl)azetidin-3-yl]-phenoxy}-ethyl)-amide

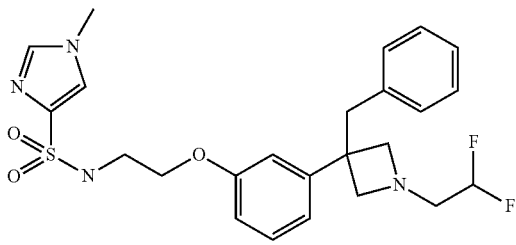

Prepared in analogy to Example 54.
ESI-MS [M+H$^+$]=491 Calculated for C$_{24}$H$_{28}$F$_2$N$_4$O$_3$S=490

Example 56

1-Methyl-1H-imidazole-4-sulfonic acid {2-[3-(3-benzyl-5-oxo-pyrrolidin-3-yl)-phenoxy]-ethyl}-amide

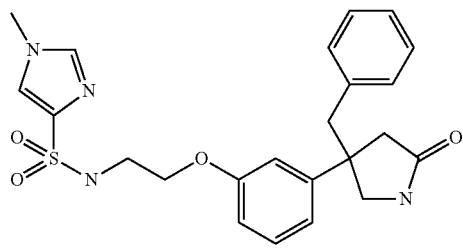 [SMILES: Cn1cnc(S(=O)(=O)NCCOc2cccc(C3(Cc4ccccc4)CNC(=O)C3)c2)c1]

56.1
3-Benzyl-3-cyano-3-(3-methoxy-phenyl)-propionic acid methyl ester

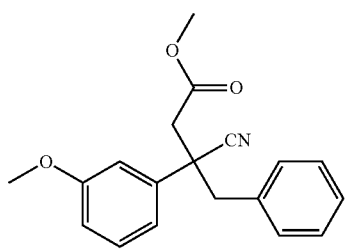 [SMILES: COC(=O)CC(C#N)(Cc1ccccc1)c1cccc(OC)c1]

To a solution of diisopropylamine (0.7 ml, 5.1 mmol) in 20 ml dry tetrahydrofuran at −78° C. was added n-butyl lithium (1.6 M in hexan, 3.2 ml, 5.1 mmol) and stirred for 1 h. A solution of 2-(3-methoxy-phenyl)-3-phenyl-propionitrile (1.0 g, 4.2 mmol) in 5 ml dry tetrahydrofuran was added to the mixture, stirred for 30 min, followed by addition of methyl 2-bromoacetate (0.6 ml, 6.3 mmol). The mixture was stirred over night at room temperature, diluted with 50 ml 1M HCl and the resulting mixture extracted with dichloromethane. The organic layer was washed with water and brine, dried over sodium bicarbonate, filtered and the solvent evaporated to obtain a yellow oil (1.3 g). Purification on 12 g SiO$_2$ using dichloromethane afforded a clear colourless oil.
m=0.51 g

56.2
4-Benzyl-4-(3-methoxy-phenyl)-pyrrolidin-2-one

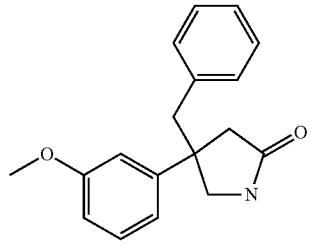 [SMILES: COc1cccc(C2(Cc3ccccc3)CNC(=O)C2)c1]

To a solution of 3-benzyl-3-cyano-3-(3-methoxy-phenyl)-propionic acid methyl ester (200 mg, 0.6 mmol) in THF (20 ml) was added Raney-Nickel (3×300 mg at 0/5/10 h). Hydrogenation occurred at 50° C. over 13 h. Methanol (15 ml) and dichloromethane (15 ml) was added, stirred for 15 min, then the mixture was filtered and the solvent evaporated. The oil was dissolved in dichloromethane, washed with HCl (1M) and brine. The organic layer was dried, filtered and the solvent evaporated. The residue was suspended in pentane, stirred over night, filtered and dried to obtain 153 mg of product.

56.3 1-Methyl-1H-imidazole-4-sulfonic acid {2-[3-(3-benzyl-5-oxo-pyrrolidin-3-yl)phenoxy]-ethyl}-amide

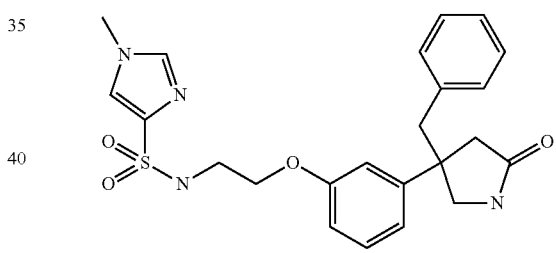

Prepared from 4-benzyl-4-(3-methoxy-phenyl)-pyrrolidin-2-one in analogy to example 1 following steps 1.3 to 1.6
ESI-MS [M+H$^+$]=455 Calculated for C$_{23}$H$_{26}$N$_4$O$_4$S=454

Example 57

N-{2-[3-(3-Benzyl-5-oxo-pyrrolidin-3-yl)-phenoxy]-ethyl}-C-cyclopropyl-methanesulfonamide

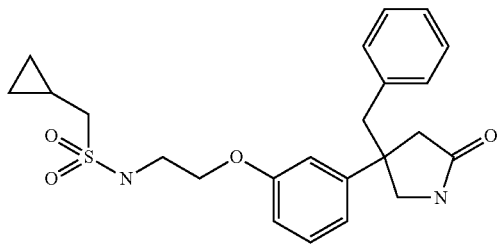 [SMILES: O=C1CC(Cc2ccccc2)(c2cccc(OCCNS(=O)(=O)CC3CC3)c2)CN1]

Prepared in analogy to example 56.
ESI-MS [M+H$^+$]=429 Calculated for C$_{23}$H$_{28}$N$_2$O$_4$S=428

Example 58

1-Methyl-1H-pyrazole-4-sulfonic acid {2-[3-(3-benzyl-5-oxo-pyrrolidin-3-yl)phenoxy]-ethyl}-amide

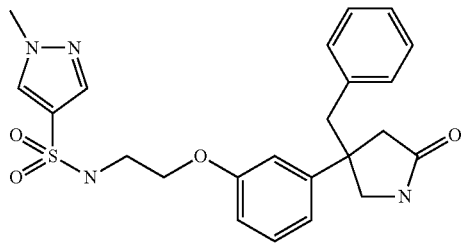 [SMILES: Cn1cc(S(=O)(=O)NCCOc2cccc(C3(Cc4ccccc4)CNC(=O)C3)c2)cn1]

Prepared in analogy to example 56.
ESI-MS [M+H$^+$]=455 Calculated for $C_{23}H_{26}N_4O_4S$=454

Example 59

N-{2-[3-(3-Benzyl-pyrrolidin-3-yl)-phenoxy]-ethyl}-C-cyclopropyl-methanesulfonamide

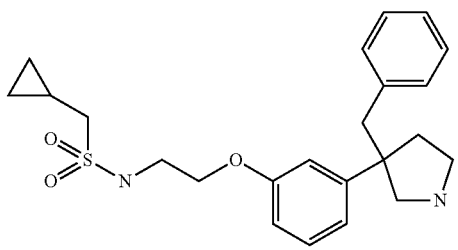 [SMILES: O=S(=O)(CC1CC1)NCCOc1cccc(C2(Cc3ccccc3)CCNC2)c1]

N-{2-[3-(3-Benzyl-5-oxo-pyrrolidin-3-yl)-phenoxy]-ethyl}-C-cyclopropyl-methanesulfonamide (78 mg; 0.2 mmol) dissolved in 10 ml THF was treated with 1M BH$_3$*THF (2 ml, 2 mmol) and stirred for 2 h under reflux. Then 0.4 ml of a 20% HCl-solution and 1.5 ml methanol were added and stirred for 1 h at 50° C. Solvent was evaporated and the residue treated with 1N NaOH. Product was extracted with ethyl acetate, the organic layer dried over Na$_2$SO$_4$, filtered and the solvent evaporated. The crude product was purified on 4.7 g amine functionalized silica (RediSep® Rf Gold) with dichloromethane and MeOH. HCl-salt was prepared (1 HCl/dioxane) in diisopropyl ether affording 33 mg product as a white solid.
ESI-MS [M+H$^+$]=415 Calculated for $C_{23}H_{30}N_2O_3S$=414

Example 60

1-Methyl-1H-pyrazole-4-sulfonic acid {2-[3-(3-benzyl-pyrrolidin-3-yl)phenoxy]-ethyl}-amide

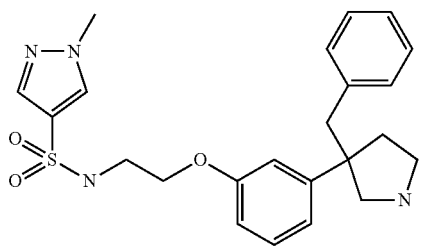 [SMILES: Cn1cc(S(=O)(=O)NCCOc2cccc(C3(Cc4ccccc4)CCNC3)c2)cn1]

Prepared in analogy to example 59.
ESI-MS [M+H$^+$]=441 Calculated for $C_{23}H_{28}N_4O_3S$=440

Example 61

1-Methyl-1H-imidazole-4-sulfonic acid {2-[3-(3-benzyl-pyrrolidin-3-yl)phenoxy]-ethyl}-amide

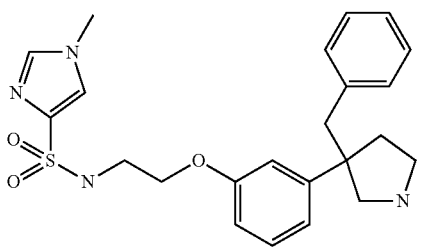 [SMILES: Cn1cnc(S(=O)(=O)NCCOc2cccc(C3(Cc4ccccc4)CCNC3)c2)c1]

Prepared in analogy to example 59
ESI-MS [M+H$^+$]=441 Calculated for $C_{23}H_{28}N_4O_3S$=440

Example 62

1-Methyl-1H-imidazole-4-sulfonic acid {2-[3-(3-benzyl-1-methyl-piperidin-3-yl)-phenoxy]-ethyl}-amide

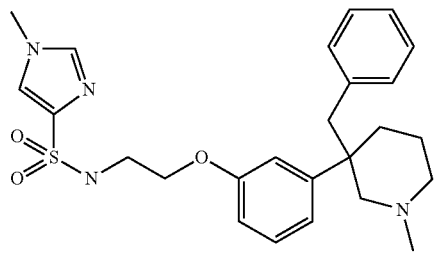 [SMILES: CN1CCCC(Cc2ccccc2)(c2cccc(OCCNS(=O)(=O)c3cn(C)cn3)c2)C1]

62.1
3-Benzyl-3-cyano-3-(3-methoxy-phenyl)-propionic acid methyl ester

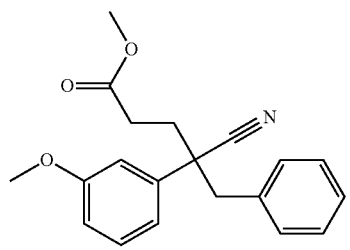 [SMILES: COC(=O)CCC(C#N)(Cc1ccccc1)c1cccc(OC)c1]

Benzyl trimethylammonium hydroxide (40% in MeOH, 100 µl, 0.22 mmol) was added to a stirred mixture of 2-(3-methoxyphenyl)-3-phenylpropanenitrile (1 g, 4.2 mmol) and ethyl acrylate (0.51 g, 5.1 mmol). After the initial exothermic reaction had subsided the mixture was refluxed for 4 h, cooled to room temperature and extracted three times with DCM. The combined organic layers were washed with water, dried, filtered and evaporated to obtain a pale yellow oil m(CR)=1.06 g that was purified by flash chromatography on 12 g SiO$_2$ using 20% EtOAc in cyclohexane affording 594 mg of product.

62.2
5-Benzyl-5-(3-methoxy-phenyl)-piperidin-2-one

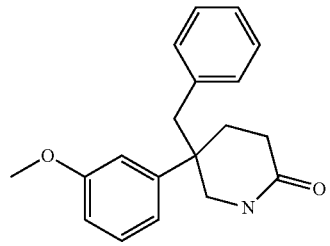 [SMILES: COc1cccc(C2(Cc3ccccc3)CCC(=O)NC2)c1]

Prepared in analogy to 56.2 using NaBH$_4$ in the presence of CoCl$_2$ instead of Raney-Nickel (see Schwarz J. et al. J. Med. Chem., 2005, 48, 3026).

62.3 1-Methyl-1H-imidazole-4-sulfonic acid {2-[3-(3-benzyl-1-methyl-piperidin-3-yl)-phenoxy]-ethyl}-amide

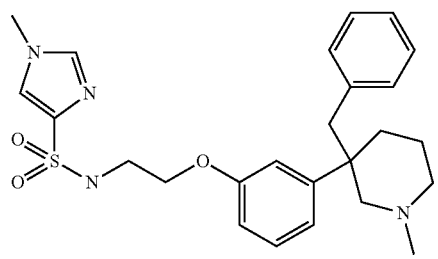 [SMILES: CN1CCCC(Cc2ccccc2)(c2cccc(OCCNS(=O)(=O)c3cn(C)cn3)c2)C1]

Prepared from 5-benzyl-5-(3-methoxy-phenyl)-piperidin-2-one in analogy to example 46.6, 46.7 and 52.2.
ESI-MS [M+H$^+$]=469 Calculated for C$_{25}$H$_{32}$N$_4$O$_3$S=468

Example 63

1-Methyl-1H-pyrazole-4-sulfonic acid {2-[3-(3-benzyl-1-methyl-piperidin-3-yl)phenoxy]-ethyl}-amide

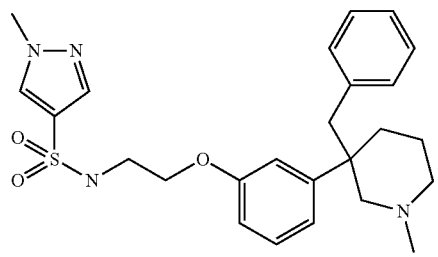 [SMILES: CN1CCCC(Cc2ccccc2)(c2cccc(OCCNS(=O)(=O)c3cnn(C)c3)c2)C1]

Prepared in analogy to example 62.
ESI-MS [M+H$^+$]=469 Calculated for C$_{25}$H$_{32}$N$_4$O$_3$S=468

Example 64

N-{2-[3-(3-Benzyl-1-methyl-piperidin-3-yl)-phenoxy]-ethyl}-C-cyclopropyl-methanesulfonamide

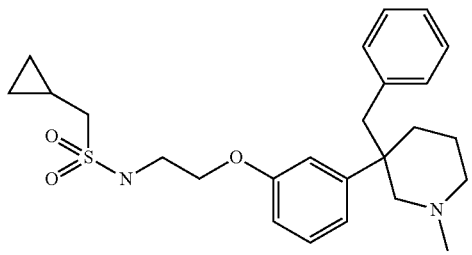 [SMILES: CN1CCCC(Cc2ccccc2)(c2cccc(OCCNS(=O)(=O)CC3CC3)c2)C1]

Prepared in analogy to example 62.
ESI-MS [M+H$^+$]=443 Calculated for C$_{25}$H$_{34}$N$_2$O$_3$S=442

Example 65

1-Methyl-1H-imidazole-4-sulfonic acid 3-(3-benzyl-5-oxo-pyrrolidin-3-yl)benzylamide

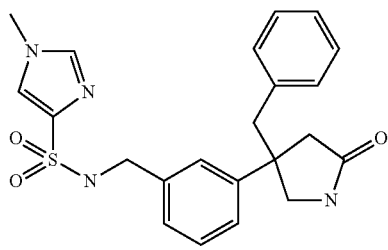 [SMILES: Cn1cnc(S(=O)(=O)NCc2cccc(C3(Cc4ccccc4)CNC(=O)C3)c2)c1]

65.1
3-Benzyl-3-cyano-3-(3-cyano-phenyl)-propionic acid methyl ester

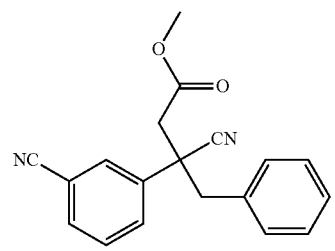 [SMILES: COC(=O)CC(C#N)(Cc1ccccc1)c1cccc(C#N)c1]

Prepared in analogy to 3-benzyl-3-cyano-3-(3-methoxy-phenyl)-propionic acid methyl ester (example 56.1).

65.2
4-(3-Aminomethyl-phenyl)-4-benzyl-pyrrolidin-2-one

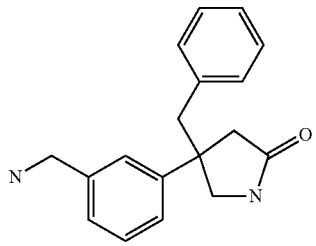 [SMILES: NCc1cccc(C2(Cc3ccccc3)CNC(=O)C2)c1]

Prepared in analogy to 4-benzyl-4-(3-methoxy-phenyl)-pyrrolidin-2-one starting from 3-benzyl-3-cyano-3-(3-cyano-phenyl)-propionic acid methyl ester (example 56.2)

65.3 1-Methyl-1H-imidazole-4-sulfonic acid 3-(3-benzyl-5-oxo-pyrrolidin-3-yl)benzylamide

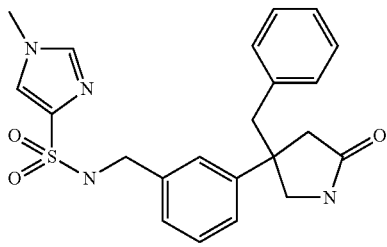 [SMILES: Cn1cnc(S(=O)(=O)NCc2cccc(C3(Cc4ccccc4)CNC(=O)C3)c2)c1]

Prepared in analogy to example 1, step 6.
ESI-MS [M+H$^+$]=425 Calculated for $C_{22}H_{24}N_4O_3S$=424

Example 66

1-Methyl-1H-pyrazole-4-sulfonic acid 3-(3-benzyl-5-oxo-pyrrolidin-3-yl)benzylamide

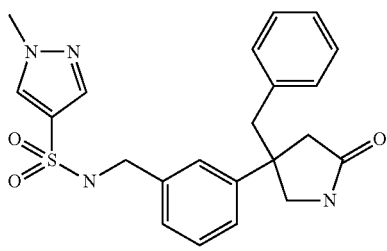 [SMILES: Cn1cc(S(=O)(=O)NCc2cccc(C3(Cc4ccccc4)CNC(=O)C3)c2)cn1]

Prepared in analogy to example 65.
ESI-MS [M+H$^+$]=425 Calculated for $C_{22}H_{24}N_4O_3S$=424

Example 67

1-Methyl-1H-pyrazole-4-sulfonic acid 3-(3-benzyl-pyrrolidin-3-yl)benzylamide

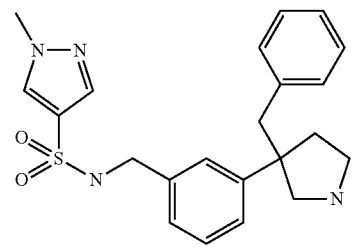 [SMILES: Cn1cc(S(=O)(=O)NCc2cccc(C3(Cc4ccccc4)CCNC3)c2)cn1]

Prepared in analogy to example 59.
ESI-MS [M+H$^+$]=411 Calculated for $C_{22}H_{26}N_4O_2S$=410

Example 68

N-[3-(3-Benzyl-pyrrolidin-3-yl)-benzyl]-C-cyclopropyl-methanesulfonamide

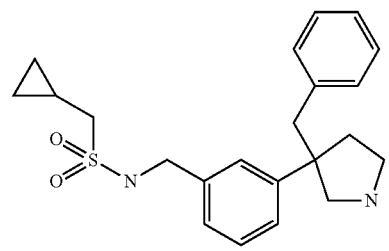 [SMILES: O=S(=O)(CC1CC1)NCc1cccc(C2(Cc3ccccc3)CCNC2)c1]

Prepared in analogy to examples 66 and 59.
ESI-MS [M+H$^+$]=385 Calculated for $C_{22}H_{28}N_2O_2S$=384

Example 69

1-Methyl-1H-pyrazole-4-sulfonic acid 3-(3-benzyl-1-methyl-pyrrolidin-3-yl)-benzylamide

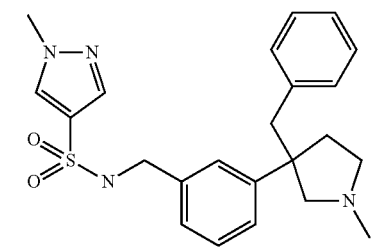

To a solution of 1-methyl-1H-pyrazole-4-sulfonic acid 3-(3-benzyl-pyrrolidin-3-yl)benzylamide (example 67, 108 mg, 0.26 mmol) and formaldehyde (37% in water, 0.2 ml, 2.6 mmol) in methanol (10 ml) was added palladium on charcoal (10%, 10 mg). Hydrogenation was performed at room temperature over night. The mixture was filtered and the solvent evaporated. The residue was diluted with dichloromethane, extracted with water, dried over $Na_2CO_3$. The solvent was evaporated to give 41 mg of product. Re-extraction of the aqueous layer afforded further 38 mg of product as a clear oil.
ESI-MS [M+H$^+$]=425 Calculated for $C_{23}H_{28}N_4O_2S$=424

Example 70

1-Methyl-1H-imidazole-4-sulfonic acid {2-[3-(3-benzyl-1-methyl-pyrrolidin-3-yl)-phenoxy]-ethyl}-amide

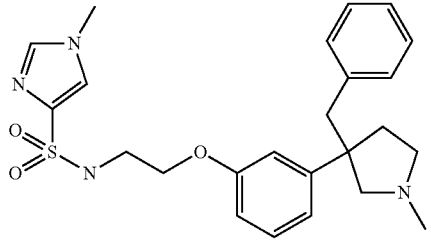 [SMILES: CN1CCC(Cc2ccccc2)(c2cccc(OCCNS(=O)(=O)c3cn(C)cn3)c2)C1]

Prepared in analogy to example 69 starting from 1-methyl-1H-imidazole-4-sulfonic acid {2-[3-(3-benzyl-pyrrolidin-3-yl)-phenoxy]-ethyl}-amide (example 61).
ESI-MS [M+H$^+$]=455 Calculated for $C_{24}H_{30}N_4O_3S$=454

Example 71

1-Methyl-1H-imidazole-4-sulfonic acid (2-{3-[3-benzyl-1-(2,2-difluoro-acetyl)pyrrolidin-3-yl]-phenoxy}-ethyl)-amide

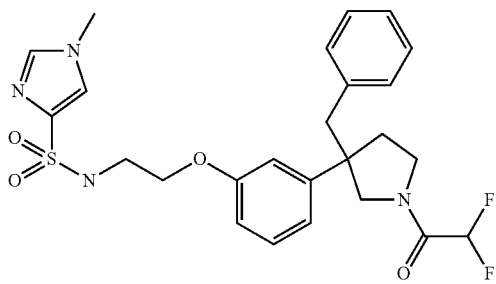 [SMILES: Cn1cnc(S(=O)(=O)NCCOc2cccc(C3(Cc4ccccc4)CCN(C(=O)C(F)F)C3)c2)c1]

Prepared in analogy to example 54.1 starting from 1-methyl-1H-imidazole-4-sulfonic acid {2-[3-(3-benzyl-pyrrolidin-3-yl)-phenoxy]-ethyl}-amide (example 61).
ESI-MS [M+H$^+$]=519 Calculated for $C_{25}H_{28}F_2N_4O_4S$=518

Example 72

1-Methyl-1H-imidazole-4-sulfonic acid (2-{3-[3-benzyl-1-(2-fluoro-ethyl)azetidin-3-yl]-phenoxy}-ethyl)-amide

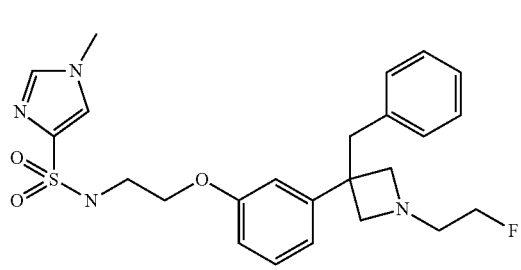 [SMILES: Cn1cnc(S(=O)(=O)NCCOc2cccc(C3(Cc4ccccc4)CN(CCF)C3)c2)c1]

72.1 1-Methyl-1H-imidazole-4-sulfonic acid (2-{3-[3-benzyl-1-(2-fluoro-acetyl)-azetidin-3-yl]-phenoxy}-ethyl)-amide

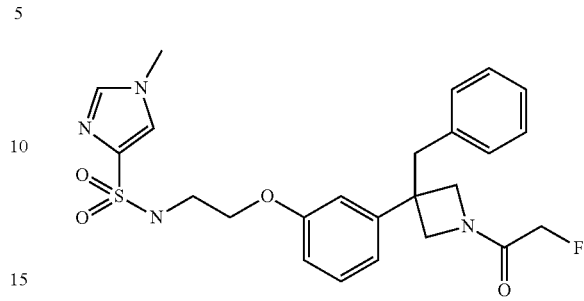

To a stirred solution of N-(2-(3-(3-benzylazetidin-3-yl)phenoxy)ethyl)-1-methyl-1H-imidazole-4-sulfonamide (81 mg, 0.190 mmol) in dry dichloromethane (1.5 ml) containing diisopropylamine (0.066 ml, 0.380 mmol) under argon was added fluoroacetyl chloride (0.022 ml, 0.285 mmol) and stirred at room temperature for 1 h. Washed with 1N HCl, sodium bicarbonate and brine, dried over MgSO$_4$, filtered, evaporated and the crude material was purified by flash silica gel chromatography on 4 g SiO$_2$-cartridge using 5% MeOH in dichloromethane affording 68.7 mg of a white solid.
ESI-MS [M+H$^+$]=487 Calculated for $C_{24}H_{27}FN_4O_4S$=486

72.2 1-Methyl-1H-imidazole-4-sulfonic acid (2-{3-[3-benzyl-1-(2-fluoro-ethyl)-azetidin-3-yl]-phenoxy}-ethyl)-amide

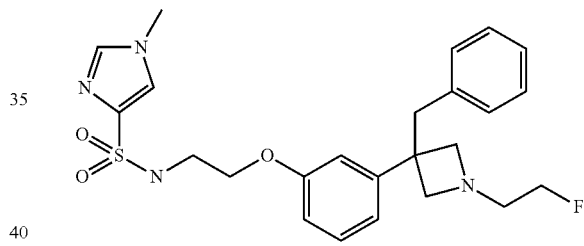

Prepared in analogy to example 54.2 starting from 1-methyl-1H-imidazole-4-sulfonic acid (2-{3-[3-benzyl-1-(2-fluoro-acetyl)-azetidin-3-yl]-phenoxy}-ethyl)-amide (example 61).
ESI-MS [M+H$^+$]=473 Calculated for $C_{24}H_{29}FN_4O_3S$=472

Example 73

1-Methyl-1H-imidazole-4-sulfonic acid (2-{3-[3-benzyl-1-(2-methoxy-ethyl)azetidin-3-yl]-phenoxy}-ethyl)-amide

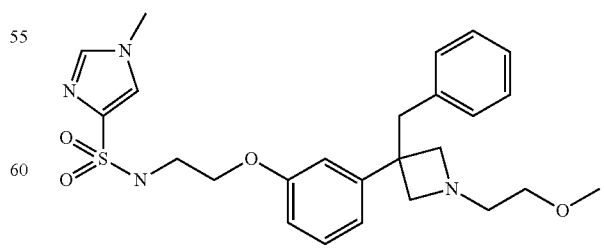

Prepared in analogy to example 72 using lithium aluminium hydride solution in tetrahydrofuran (1M) instead of borane dimethyl sulphide as reducing agent.
ESI-MS [M+H$^+$]=485 Calculated for $C_{25}H_{32}N_4O_4S$=484

Example 74

1-Methyl-1H-imidazole-4-sulfonic acid {2-[3-(3-benzyl-1-methyl-pyrrolidin-3-yl)-phenoxy]-ethyl}-methyl-amide

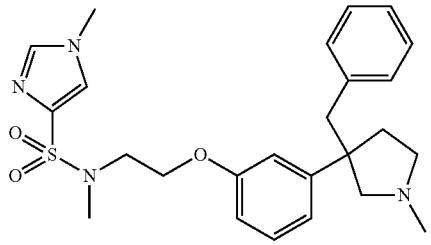 [SMILES: CN1CCC(Cc2ccccc2)(c2cccc(OCCN(C)S(=O)(=O)c3cn(C)cn3)c2)C1]

Prepared in analogy to example 53.
ESI-MS [M+H$^+$]=469 Calculated for $C_{25}H_{32}N_4O_3S$=468

Example 75

1-Methyl-1H-imidazole-4-sulfonic acid (2-{3-[3-benzyl-1-(2-fluoro-ethyl)pyrrolidin-3-yl]-phenoxy}-ethyl)-amide

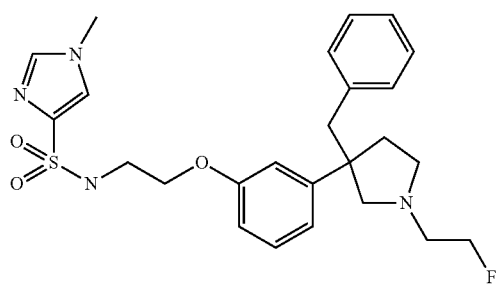 [SMILES: Cn1cnc(S(=O)(=O)NCCOc2cccc(C3(Cc4ccccc4)CCN(CCF)C3)c2)c1]

Prepared in analogy to example 72.
ESI-MS [M+H$^+$]=487 Calculated for $C_{25}H_{31}FN_4O_3S$=486

Example 76

1-Methyl-1H-imidazole-4-sulfonic acid (2-{3-[3-benzyl-1-(2,2-dimethylpropyl)-pyrrolidin-3-yl]-phenoxy}-ethyl)-amide

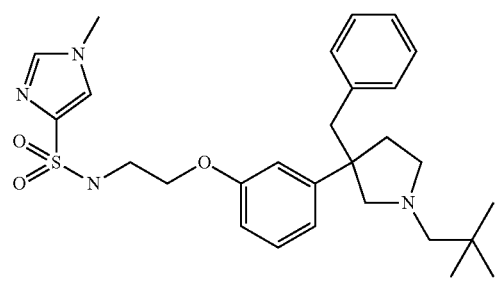 [SMILES: Cn1cnc(S(=O)(=O)NCCOc2cccc(C3(Cc4ccccc4)CCN(CC(C)(C)C)C3)c2)c1]

Prepared in analogy to example 73.
ESI-MS [M+H$^+$]=511 Calculated for $C_{28}H_{38}N_4O_3S$=510

Example 77

1-Methyl-1H-imidazole-4-sulfonic acid {2-[3-(3-benzyl-1-isopropyl-pyrrolidin-3-yl)-phenoxy]-ethyl}-amide

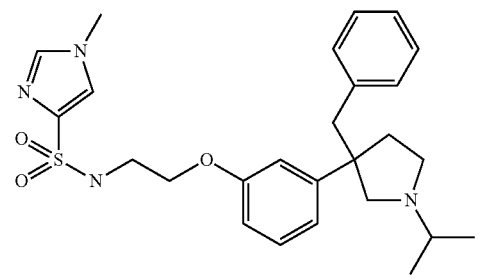 [SMILES: CC(C)N1CCC(Cc2ccccc2)(c2cccc(OCCNS(=O)(=O)c3cn(C)cn3)c2)C1]

To a solution of 1-methyl-1H-imidazole-4-sulfonic acid {2-[3-(3-benzyl-pyrrolidin-3-yl)phenoxy]-ethyl}-amide (example 61, 59 mg, 0.13 mmol) in dichloromethane under nitrogen was added acetone (8 mg, 0.14 mmol), two drops acetic acid, 2 mg $Na_2SO_4$, sodium triacetoxyborohydride. The mixture was stirred over night at room temperature. Saturated $NaHCO_3$-solution was added and the mixture was extracted with dichloromethane. The organic layer was washed with water, dried over $Na_2SO_4$ and the solvent evaporated affording 54 mg of colorless oil. Purification on 4 g Si % with dichloromethane+5% MeOH to 10% MeOH afforded 4 mg of product.
ESI-MS [M+H$^+$]=483 Calculated for $C_{26}H_{34}N_4O_3S$=482

Example 78

1-Methyl-1H-imidazole-4-sulfonic acid {2-[3-(3-benzyl-1-methyl-azetidin-3-yl)phenoxy]-ethyl}-amide

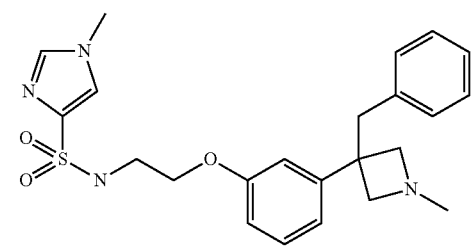 [SMILES: CN1CC(Cc2ccccc2)(c2cccc(OCCNS(=O)(=O)c3cn(C)cn3)c2)C1]

Prepared in analogy to Example 52.5
ESI-MS [M+H$^+$]=441 Calculated for $C_{23}H_{28}N_4O_3S$=440

Biological Testing

1. [$^3$H]-Glycine uptake into recombinant CHO cells expressing human GlyT1: Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 μl HBSS (Gibco BRL, #14025-050) with 5 mM L-Alanine (Merck #1007). 80 μl HBSS buffer were added, followed by 10 μl inhibitor or vehicle (10% DMSO) and 10 μl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 μM Org24598. $IC_{50}$ calculations were made by four-parametric logistic nonlinear regression analysis (GraphPad Prism) using determinations within the range of linear increase of [$^3$H]-glycine incorporation between 60 and 120 min.

2. Radioligand binding assays using recombinant CHO cell membranes expressing human GlyT1:

Radioligand binding to human GlyT1c transporter-expressing membranes was determined as described in Mezler et al., Molecular Pharmacology 74:1705-1715, 2008.

The following results were obtained with the compounds disclosed in the examples:

TABLE 1

| Example | radioligand binding $K_{iapp}$ [μM] |
|---|---|
| 1 | ≤1 |
| 2 | ≤1 |
| 3 | ≤0.1 |
| 4 | ≤0.1 |
| 5 | ≤0.1 |
| 6 | ≤0.1 |
| 7 | ≤1 |
| 8 | ≤1 |
| 9 | ≤1 |
| 10 | ≤0.1 |
| 11 | ≤1 |
| 12 | ≤0.1 |
| 13 | ≤100 |
| 14 | ≤10 |
| 15 | ≤10 |
| 16 | ≤10 |
| 17 | ≤10 |
| 18 | ≤0.1 |
| 19 | ≤1 |
| 20 | ≤10 |
| 21 | ≤1 |
| 22 | ≤10 |
| 23 | ≤0.1 |
| 24 | ≤0.1 |
| 25 | ≤1 |
| 26 | ≤1 |
| 27 | ≤1 |
| 28 | ≤0.1 |
| 29 | ≤0.1 |
| 30 | ≤0.1 |
| 31 | ≤0.1 |
| 32 | ≤0.1 |
| 33 | ≤0.1 |
| 34 | ≤1 |
| 35 | ≤1 |
| 36 | ≤1 |
| 37 | ≤1 |
| 39 | ≤10 |
| 40 | ≤10 |
| 41 | ≤10 |
| 42 | ≤10 |
| 43 | ≤10 |
| 44 | ≤10 |
| 45 | ≤10 |
| 46 | ≤10 |
| 47 | ≤1 |
| 48 | ≤1 |
| 49 | ≤1 |
| 50 | ≤0.1 |
| 51 | ≤0.1 |
| 52 | ≤0.1 |
| 53 | ≤1 |
| 54 | ≤1 |
| 55 | ≤1 |
| 56 | ≤1 |
| 57 | ≤10 |

TABLE 1-continued

| Example | radioligand binding $K_{iapp}$ [μM] |
|---|---|
| 58 | ≤1 |
| 59 | ≤0.1 |
| 60 | ≤0.1 |
| 61 | ≤0.1 |
| 62 | ≤0.1 |
| 63 | ≤0.1 |
| 64 | ≤10 |
| 65 | — |
| 66 | ≤10 |
| 67 | ≤0.1 |
| 68 | ≤1 |
| 69 | ≤1 |
| 70 | ≤0.1 |
| 71 | ≤1 |
| 72 | ≤0.1 |
| 73 | ≤0.1 |
| 74 | ≤1 |
| 75 | ≤0.1 |
| 76 | ≤0.1 |
| 77 | ≤1 |
| 78 | ≤0.1 |

We claim:

1. Phenalkylamine derivatives of the formula (I)

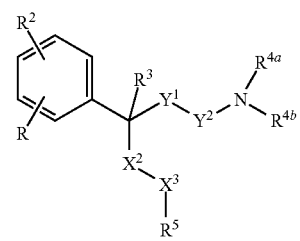

wherein
R is $R^1$—W-$A^1$-Q-Y-$A^2$-$X^1$—;
$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, tri($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$- alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl;

W is —$NR^8$— or a bond;

$A^1$ is optionally substituted $C_1$-$C_4$-alkylene or a bond;

Q is —$S(O)_2$—;

Y is —$NR^9$—;

$A^2$ is optionally substituted $C_1$-$C_4$-alkylene, $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_2$-$C_4$-alkenylene, optionally substituted $C_2$-$C_4$-alkynylene, optionally substituted $C_6$-$C_{12}$-arylene, optionally substituted $C_6$-$C_{12}$-heteroarylene or a bond;

$X^1$ is —O—, —$NR^{11}$—, —S—, optionally substituted $C_1$-$C_4$-alkylene, optionally substituted $C_2$-$C_4$-alkenylene, or optionally substituted $C_2$-$C_4$-alkynylene;

$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms to which they are bound form a 5- or 6 membered ring;

$R^3$ is hydrogen or $C_1$-$C_6$-alkyl;

$X^2$ is —O—, —$NR^6$—, —S—, >$CR^{12a}R^{12b}$ or a bond;

$X^3$ is —O—, —$NR^7$—, —S—, >$CR^{13a}R^{13b}$ or a bond;

$R^5$ is optionally substituted $C_6$-$C_{12}$-aryl, optionally substituted $C_3$-$C_{12}$-cycloalkyl or optionally substituted $C_3$-$C_{12}$-heterocyclyl;

$Y^1$ is >$CR^{14a}R^{14b}$ or a bond;

$Y^2$ is >$CR^{15a}R^{15b}$ or a bond;

$R^{4a}$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, $C_6$-$C_{12}$-aryl-$C_1$-$C_4$-alkyl, $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino, —NO or $C_3$-$C_{12}$-heterocyclyl; or $R^{4a}$, $R^3$ together are optionally substituted $C_1$-$C_6$-alkylene; or $R^{4a}$, $R^{14a}$ together are optionally substituted $C_1$-$C_6$-alkylene;

$R^{4b}$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_3$-$C_{12}$-cycloalkyl, $CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino, —NO or $C_3$-$C_{12}$-heterocyclyl; or $R^{4a}$, $R^{4b}$ together are optionally substituted $C_1$-$C_6$-alkylene, wherein one —$CH_2$— of $C_1$-$C_6$-alkylene may be replaced by an oxygen atom or —$NR^{16}$; or $R^6$ is hydrogen or $C_1$-$C_6$-alkyl;

$R^7$ is hydrogen or $C_1$-$C_6$-alkyl;

$R^8$ is hydrogen or $C_1$-$C_6$-alkyl;

$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl or $C_3$-$C_{12}$-heterocyclyl; or $R^9$, $R^1$ together are $C_1$-$C_4$-alkylene; or $R^9$ is $C_1$-$C_4$-alkylene that is bound to a carbon atom in $A^2$ and $A^2$ is $C_1$-$C_4$-alkylene or to a carbon atom in $X^1$ and $X^1$ is $C_1$-$C_4$-alkylene;

$R^{10}$ is hydrogen, $C_1$-$C_6$-alkyl or $C_1$-$C_6$-alkylsulfonyl;

$R^{11}$ is hydrogen or $C_1$-$C_6$-alkyl, or $R^9$, $R^{11}$ together are $C_1$-$C_4$-alkylene, $R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{12b}$ is hydrogen or $C_1$-$C_6$-alkyl, or $R^{12a}$, $R^{12b}$ together are carbonyl or optionally substituted $C_1$-$C_4$-alkylene, wherein one —$CH_2$— of $C_1$-$C_4$-alkylene may be replaced by an oxygen atom or —$NR^{17}$—;

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{13b}$ is hydrogen or $C_1$-$C_6$-alkyl, or $R^{13a}$, $R^{13b}$ together are carbonyl or optionally substituted $C_1$-$C_4$-alkylene, wherein one —$CH_2$— of $C_1$-$C_4$-alkylene may be replaced by an oxygen atom or —$NR^{18}$—;

$R^{14a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{14b}$ is hydrogen or $C_1$-$C_6$-alkyl, or $R^{14a}$, $R^{14b}$, together are carbonyl or optionally substituted $C_1$-$C_4$-alkylene, wherein one or two —$CH_2$— of $C_1$-$C_4$-alkylene may be replaced by an oxygen atom or —$NR^{19}$—;

$R^{15a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{15b}$ is hydrogen or $C_1$-$C_6$-alkyl, or $R^{15a}$, $R^{15b}$ together are carbony or optionally substituted $C_1$-$C_4$-alkylene, wherein one or two —$CH_2$— of $C_1$-$C_4$-alkylene may be replaced by an oxygen atom or —$NR^{19}$—;

$R^{16}$ is hydrogen or $C_1$-$C_6$-alkyl;

$R^{17}$ is hydrogen or $C_1$-$C_6$-alkyl;

$R^{18}$ is hydrogen or $C_1$-$C_6$-alkyl, and $R^{19}$ is hydrogen or $C_1$-$C_6$-alkyl, or a physiologically tolerated salt thereof.

2. The compound of claim 1, wherein —Y-$A^2$-$X^1$— comprises at least 2, 3 or 4 atoms in the main chain.

3. The compound of claim 1, wherein $R^1$ is $C_1$-$C_6$-alkyl, $C_3$-$C_{12}$-cycloalkyl-$C_1$-$C_4$-alkyl, halogenated $C_1$-$C_6$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl, $C_2$-$C_6$-alkenyl, optionally substituted $C_6$-$C_{12}$-aryl, hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl.

4. The compound of claim 1, wherein $A^1$ is a bond, or $A^1$ is $C_1$-$C_4$-alkylene and W is —$NR^8$—.

5. The compound of claim 1, wherein $A^2$ is $C_1$-$C_4$-alkylene, or $A^2$ is $C_6$-$C_{12}$-arylene selected from the group consisting of phen-1,4-ylene and phen-1,3-ylene, or $C_6$-$C_{12}$-heteroarylene selected from the group consisting of pyrid-2,5-ylene and pyrid-2,4-ylene.

6. The compound of claim 1, wherein $X^1$ is —O— or —$NR^{11}$, or $X^1$ is optionally substituted $C_1$-$C_4$-alkylene and $A^2$ is a bond, or $X^1$ is optionally substituted $C_2$-$C_4$-alkynylene and $A^2$ is a bond.

7. The compound of claim 1, wherein $R^1$—W-$A^1$-Q-Y-$A^2$-$X^1$— is $R^1$—$S(O)_2$—NH-$A^2$-$X^1$—.

8. The compound of claim 1, having one of the formulae

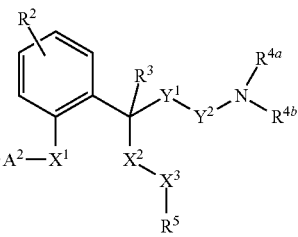

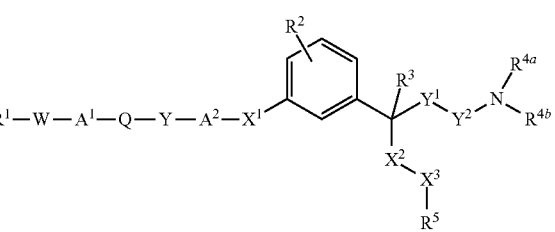

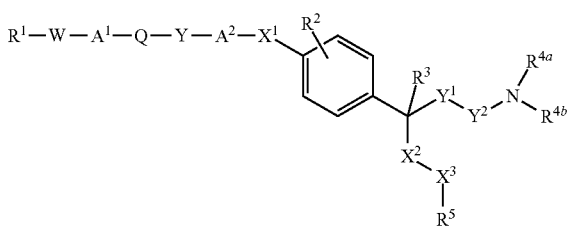

wherein $R^1$, W, $A^1$, Q, Y, $A^2$, $X^1$, $R^2$, $R^3$, $X^2$, $X^3$, $R^5$, $Y^1$, $Y^2$, $R^{4a}$, $R^{4b}$ are as defined in claim 1.

9. The compound of claim 1, wherein $X^2$ is $CR^{12a}R^{12b}$ and $X^3$ is a bond.

10. The compound of claim 1, wherein $R^{12a}$ is hydrogen or $C_1$-$C_6$-alkyl and $R^{12b}$ is hydrogen or $C_1$-$C_6$-alkyl, or $R^{12a}$, $R^{12b}$ together are optionally substituted $C_1$-$C_4$-alkylene.

11. The compound of claim 1, having the formula

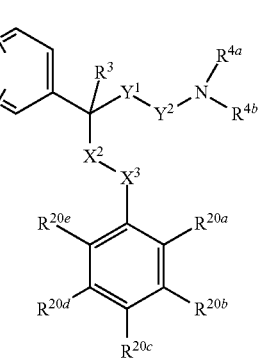

wherein $R^{20a}$, $R^{20b}$, $R^{20c}$, $R^{20d}$, $R^{20e}$ independently are hydrogen, halogen, optionally substituted $C_1$-$C_6$-alkyl, halogenated $C_1$-$C_6$-alkyl, CN, hydroxy, $C_1$-$C_6$-alkoxy, amino, $C_1$-$C_6$-alkylamino, di-$C_1$-$C_6$-alkylamino or $C_3$-$C_{12}$-heterocyclyl.

12. The compound of claim 1, wherein $Y^1$ is a bond and $Y^2$ is >$CR^{15a}R^{15b}$, or $Y^1$ is a bond and $Y^2$ is a bond.

13. The compound of claim 1, wherein $R^{4a}$ is hydrogen, $C_1$-$C_6$-alkyl, $C_3$-$C_{12}$-cycloalkyl-$C_1$-$C_4$-alkyl, halogenated $C_1$-$C_4$-alkyl, amino-$C_1$-$C_4$-alkyl, $CH_2CN$, $C_6$-$C_{12}$-aryl-$C_1$-$C_4$-alkyl, $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, —C(=NH)NH_2, —C(=NH)NHCN, $C_1$-$C_6$-alkylsulfonyl, amino, —NO or $C_3$-$C_{12}$-heterocyclyl, or $R^{4a}$, $R^3$ together are optionally substituted $C_1$-$C_4$-alkylene, or $R^{4a}$, $R^{14a}$ together are optionally substituted $C_1$-$C_4$-alkylene.

14. The compound of claim 1, wherein $R^{4b}$ is hydrogen or $C_1$-$C_6$-alkyl.

15. The compound of claim 1, wherein $R^{4a}$, $R^{4b}$ together are optionally substituted $C_1$-$C_6$-alkylene, wherein one —$CH_2$— of $C_1$-$C_4$-alkylene may be replaced by an oxygen atom.

16. The compound of claim 1, wherein
R is $R^1$—W-$A^1$-Q-Y-$A^2$-$X^1$—;
$R^1$ is $C_1$-$C_6$-alkyl, $C_3$-$C_{12}$-cycloalkyl-$C_1$-$C_4$-alkyl, halogenated $C_1$-$C_6$-alkyl, or optionally substituted $C_3$-$C_{12}$-heterocyclyl;
W is a bond;
$A^1$ is a bond;
Q is —$S(O)_2$—;
Y is —$NR^9$—;
$A^2$ is $C_1$-$C_4$-alkylene or a bond;
$X^1$ is —O— or optionally substituted $C_1$-$C_4$-alkylene;
$R^2$ is hydrogen or halogen;
$R^3$ is hydrogen;
$Y^1$ is a bond;
$Y^2$ is >$CR^{15a}R^{15b}$ or a bond;
$R^{4a}$ is hydrogen, $C_1$-$C_6$-alkyl, $C_6$-$C_{12}$-aryl-$C_1$-$C_4$-alkyl, or $C_1$-$C_4$-alkoxycarbonyl; or
$R^{4a}$, $R^3$ together are optionally substituted $C_1$-$C_6$-alkylene,
$R^{4b}$ is hydrogen, $C_1$-$C_6$-alkyl, halogenated $C_1$-$C_4$-alkyl, $C_1$-$C_6$-alkoxy-$C_1$-$C_4$-alkyl, (halogenated $C_1$-$C_4$-alkyl) carbonyl or $C_1$-$C_4$-alkoxycarbonyl; or
$R^{4a}$, $R^{4b}$ together are optionally substituted $C_1$-$C_6$-alkylene, wherein one —$CH_2$— of $C_1$-$C_6$-alkylene may be replaced by an oxygen atom;

X² is CR¹²ᵃR¹²ᵇ;
X³ is a bond;
R⁵ is optionally substituted phenyl;
R⁹ is hydrogen or $C_1$-$C_6$-alkyl;
R¹²ᵃ is hydrogen; and
R¹²ᵇ is hydrogen; or
R¹²ᵃ, R¹²ᵇ
together are optionally substituted $C_1$-$C_4$-alkylene;
R¹⁵ᵃ is hydrogen; and
R¹⁵ᵇ is hydrogen; or
R¹⁵ᵃ, R¹⁵ᵇ
together are carbonyl.

17. in the compound of claim 1, which is:
1-Methyl-1H-imidazole-4-sulfonic acid {2-[3-(2-amino-1-benzyl-ethyl)-4-fluoro-phenoxy]-ethyl}-amide;
1-Methyl-1H-pyrazole-4-sulfonic acid (2-{3-[2-amino-1-(3-chloro-benzyl)-ethyl]-phenoxy}-ethyl)-amide;
1-Methyl-1H-pyrazole-4-sulfonic acid {2-[5-(2-amino-1-benzyl-ethyl)-2-fluoro-phenoxy]-ethyl}-amide;
1-Methyl-1H-imidazole-4-sulfonic acid {2-[5-(2-amino-1-benzyl-ethyl)-2-fluoro-phenoxy]-ethyl}-amide;
1-Methyl-1H-imidazole-4-sulfonic acid {2-[3-(2-amino-1-benzyl-ethyl)-phenoxy]-ethyl}-amide;
1-Methyl-1H-pyrazole-4-sulfonic acid {2-[3-(2-amino-1-benzyl-ethyl)-phenoxy]-ethyl}-amide;
1-Methyl-1H-pyrazole-4-sulfonic acid (2-{3-[2-amino-1-(3,5-difluoro-benzyl)-ethyl]-phenoxy}-ethyl)-amide;
1-Methyl-1H-pyrazole-4-sulfonic acid (2-{3-[2-amino-1-(4-chloro-benzyl)-ethyl]-phenoxy}-ethyl)-amide;
1-Methyl-1H-imidazole-4-sulfonic acid (2-{3-[2-amino-1-(3-chloro-benzyl)-ethyl]-phenoxy}-ethyl)-amide;
1-Methyl-1H-pyrazole-4-sulfonic acid (2-{3-[2-amino-1-(3-trifluoromethyl-benzyl)-ethyl]-phenoxy}-ethyl)-amide;
1-Methyl-1H-imidazole-4-sulfonic acid (2-{3-[2-amino-1-(3,5-difluoro-benzyl)-ethyl]-phenoxy}-ethyl)-amide;
1-Methyl-1H-imidazole-4-sulfonic acid (2-{3-[2-amino-1-(3-trifluoromethyl-benzyl)-ethyl]-phenoxy}-ethyl)-amide;
2-[3-(Cyclopropylmethanesulfonylamino-methyl)-phenyl]-3-phenyl-propionamide;
N-[3-(2-Amino-1-benzyl-ethyl)-benzyl]-C-cyclopropyl-methanesulfonamide;
2-{3-[(1-Methyl-1H-pyrazole-4-sulfonylamino)-methyl]-phenyl}-3-phenyl-propionamide;
2-{3-[(1-Methyl-1H-imidazole-4-sulfonylamino)-methyl]-phenyl}-3-phenyl-propionamide;
1-Methyl-1H-imidazole-4-sulfonic acid 3-(1-benzyl-2-morpholin-4-yl-2-oxo-ethyl)benzylamide;
1-Methyl-1H-pyrazole-4-sulfonic acid 3-(2-amino-1-benzyl-ethyl)-benzylamide;
1-Methyl-1H-imidazole-4-sulfonic acid 3-(2-amino-1-benzyl-ethyl)-benzylamide;
1-Methyl-1H-imidazole-4-sulfonic acid 3-(1-benzyl-2-morpholin-4-yl-ethyl)-benzylamide;
1-Methyl-1H-pyrazole-4-sulfonic acid 3-(1-benzyl-2-morpholin-4-yl-ethyl)-benzylamide;
N-[3-(1-Benzyl-2-morpholin-4-yl-ethyl)-benzyl]-C-cyclopropyl-methanesulfonamide;
1-Methyl-1H-imidazole-4-sulfonic acid {2-[3-(1-benzyl-2-dimethylamino-ethyl)-4-fluorophenoxy]-ethyl}-amide;
1-Methyl-1H-pyrazole-4-sulfonic acid {2-[3-(1-benzyl-2-dimethylamino-ethyl)-phenoxy]-ethyl}-amide;
1-Methyl-1H-imidazole-4-sulfonic acid {2-[3-(1-benzyl-2-dimethylamino-ethyl)-phenoxy]-ethyl}-amide;
1-Methyl-1H-imidazole-4-sulfonic acid 3-(1-benzyl-2-dimethylamino-ethyl)-benzylamide;
1-Methyl-1H-pyrazole-4-sulfonic acid 3-(1-benzyl-2-dimethylamino-ethyl)-benzylamide;
1-Methyl-1H-pyrazole-4-sulfonic acid (2-{3-[2-dimethylamino-1-(3-trifluoromethyl-benzyl)ethyl]-phenoxy}-ethyl)-amide;
1-Methyl-1H-imidazole-4-sulfonic acid (2-{3-[2-dimethylamino-1-(3-trifluoromethylbenzyl)-ethyl]-phenoxy}-ethyl)-amide;
1-Methyl-1H-pyrazole-4-sulfonic acid {2-[3-(1-benzyl-2-dimethylamino-ethyl)-4-chlorophenoxy]-ethyl}-amide;
1-Methyl-1H-pyrazole-4-sulfonic acid {2-[5-(1-benzyl-2-dimethylamino-ethyl)-2-fluorophenoxy]-ethyl}-amide;
1-Methyl-1H-imidazole-4-sulfonic acid {2-[5-(1-benzyl-2-dimethylamino-ethyl)-2-fluorophenoxy]-ethyl}-amide;
1-Methyl-1H-pyrazole-4-sulfonic acid {2-[3-(1-benzyl-2-dimethylamino-ethyl)-4-fluorophenoxy]-ethyl}-amide;
1-Methyl-1H-pyrazole-4-sulfonic acid {2-[3-(1-benzyl-2-pyrrolidin-1-yl-ethyl)-phenoxy]-ethyl}-amide;
1-Methyl-1H-imidazole-4-sulfonic acid {2-[3-(1-benzyl-2-pyrrolidin-1-yl-ethyl)-phenoxy]-ethyl}-amide;
1-Methyl-1H-pyrazole-4-sulfonic acid {2-[3-(2-azetidin-1-yl-1-benzyl-ethyl)-phenoxy]-ethyl}-amide;
1-Methyl-1H-pyrazole-4-sulfonic acid 3-(2-azetidin-1-yl-1-benzyl-ethyl)-benzylamide;
Propane-1-sulfonic acid [2-(3-{benzylamino-[1-(4-chloro-phenyl)-cyclobutyl]-methyl}-phenoxy)-ethyl]-amide;
tert-Butyl {2-[1-(4-chlorophenyl)cyclobutyl]-2-[3-({methyl[(1-methyl-1H-pyrazol-4-yl)sulfonyl]amino}methyl)phenyl]ethyl}carbamate;
tert-Butyl {2-[1-(4-chlorophenyl)cyclobutyl]-2-[3-{[methyl(propylsulfonyl)amino]methyl}phenyl)ethyl}carbamate;
tert-Butyl {2-[1-(4-chlorophenyl)cyclobutyl]-2-[3-({methyl[(1-methyl-1H-imidazol-4-yl)sulfonyl]amino}methyl)phenyl]ethyl}carbamate;
N-(3-{2-amino-1-[1-(4-chlorophenyl)cyclobutyl]ethyl}benzyl)-N-methylpropane-1-sulfonamide;
N-(3-{2-amino-1-[1-(4-chlorophenyl)cyclobutyl]ethyl}benzyl)-3-fluoro-N-methylpropane-1-sulfonamide;
N-(3-{2-amino-1-[1-(4-chlorophenyl)cyclobutyl]ethyl}benzyl)-N,1-dimethyl-1H-imidazole-4-sulfonamide;
N-(3-{2-amino-1-[1-(4-chlorophenyl)cyclobutyl]ethyl}benzyl)-N,1-dimethyl-1H-pyrazole-4-sulfonamide;
1-Methyl-1H-pyrazole-4-sulfonic acid {2-[3-(3-benzyl-azetidin-3-yl)-phenoxy]-ethyl}-amide;
3-Benzyl-3-{3-[2-(1-methyl-1H-imidazole-4-sulfonylamino)-ethoxy]-phenyl}-azetidine-1-carboxylic acid ethyl ester;
3-Benzyl-3-[3-(2-cyclopropylmethanesulfonylaminoethoxy)-phenyl]-azetidine-1-carboxylic acid ethyl ester;
N-{2-[3-(3-Benzyl-azetidin-3-yl)-phenoxy]-ethyl}-C-cyclopropyl-methane sulfonamide;
1-Methyl-1H-pyrazole-4-sulfonic acid {2-[3-(3-benzyl-azetidin-3-yl)-phenoxy]-ethyl}-amide;
1-Methyl-1H-imidazole-4-sulfonic acid {2-[3-(3-benzyl-azetidin-3-yl)-phenoxy]-ethyl}-amide;

1-Methyl-1H-imidazole-4-sulfonic acid {2-[5-(3-benzyl-1-methyl-azetidin-3-yl)-2-fluorophenoxy]-ethyl}-amide;
1-Methyl-1H-imidazole-4-sulfonic acid {2-[5-(3-benzyl-1-methyl-azetidin-3-yl)-2-fluorophenoxy]-ethyl}-methyl-amide;
1-Methyl-1H-imidazole-4-sulfonic acid (2-{3-[3-benzyl-1-(2,2,2-trifluoro-ethyl)-azetidin-3-yl]-phenoxy}-ethyl)-amide;
1-Methyl-1H-imidazole-4-sulfonic acid (2-{3-[3-benzyl-1-(2,2-difluoro-ethyl)-azetidin-3-yl]-phenoxy}-ethyl)-amide;
1-Methyl-1H-imidazole-4-sulfonic acid {2-[3-(3-benzyl-5-oxo-pyrrolidin-3-yl)-phenoxy]-ethyl}-amide;
N-{2-[3-(3-Benzyl-5-oxo-pyrrolidin-3-yl)-phenoxy]-ethyl}-C-cyclopropyl-methanesulfonamide;
1-Methyl-1H-pyrazole-4-sulfonic acid {2-[3-(3-benzyl-5-oxo-pyrrolidin-3-yl)-phenoxy]-ethyl}-amide;
N-{2-[3-(3-Benzyl-pyrrolidin-3-yl)-phenoxy]-ethyl}-C-cyclopropyl-methanesulfonamide;
1-Methyl-1H-pyrazole-4-sulfonic acid {2-[3-(3-benzyl-pyrrolidin-3-yl)-phenoxy]-ethyl}-amide;
1-Methyl-1H-imidazole-4-sulfonic acid {2-[3-(3-benzyl-pyrrolidin-3-yl)-phenoxy]-ethyl}-amide;
1-Methyl-1H-imidazole-4-sulfonic acid {2-[3-(3-benzyl-1-methyl-piperidin-3-yl)-phenoxy]-ethyl}-amide;
1-Methyl-1H-pyrazole-4-sulfonic acid {2-[3-(3-benzyl-1-methyl-piperidin-3-yl)-phenoxy]-ethyl}-amide;
N-{2-[3-(3-Benzyl-1-methyl-piperidin-3-yl)-phenoxy]-ethyl}-C-cyclopropyl-methanesulfonamide;
1-Methyl-1H-imidazole-4-sulfonic acid 3-(3-benzyl-5-oxo-pyrrolidin-3-yl)-benzylamide;
1-Methyl-1H-pyrazole-4-sulfonic acid 3-(3-benzyl-5-oxo-pyrrolidin-3-yl)-benzylamide;
1-Methyl-1H-pyrazole-4-sulfonic acid 3-(3-benzyl-pyrrolidin-3-yl)-benzylamide;
N-[3-(3-Benzyl-pyrrolidin-3-yl)-benzyl]-C-cyclopropyl-methanesulfonamide;
1-Methyl-1H-pyrazole-4-sulfonic acid 3-(3-benzyl-1-methyl-pyrrolidin-3-yl)-benzylamide;
1-Methyl-1H-imidazole-4-sulfonic acid {2-[3-(3-benzyl-1-methyl-pyrrolidin-3-yl)-phenoxy]-ethyl}-amide;
1-Methyl-1H-imidazole-4-sulfonic acid (2-{3-[3-benzyl-1-(2,2-difluoro-acetyl)-pyrrolidin-3-yl]-phenoxy}-ethyl)-amide;
1-Methyl-1H-imidazole-4-sulfonic acid (2-{3-[3-benzyl-1-(2-fluoro-ethyl)-azetidin-3-yl]-phenoxy}-ethyl)-amide;
1-Methyl-1H-imidazole-4-sulfonic acid (2-{3-[3-benzyl-1-(2-methoxy-ethyl)-azetidin-3-yl]-phenoxy}-ethyl)-amide;
1-Methyl-1H-imidazole-4-sulfonic acid {2-[3-(3-benzyl-1-methyl-pyrrolidin-3-yl)-phenoxy]-ethyl}-methyl-amide;
1-Methyl-1H-imidazole-4-sulfonic acid (2-{3-[3-benzyl-1-(2-fluoro-ethyl)-pyrrolidin-3-yl]-phenoxy}-ethyl)-amide;
1-Methyl-1H-imidazole-4-sulfonic acid (2-{3-[3-benzyl-1-(2,2-dimethyl-propyl)-pyrrolidin-3-yl]-phenoxy}-ethyl)-amide; or
1-Methyl-1H-imidazole-4-sulfonic acid {2-[3-(3-benzyl-1-isopropyl-pyrrolidin-3-yl)phenoxy]-ethyl}-amide;

or a physiologically tolerated salt thereof.

18. A pharmaceutical composition comprising a carrier and a compound of claim 1.

* * * * *